(12) United States Patent
McNutt

(10) Patent No.: US 12,728,257 B2
(45) Date of Patent: Sep. 8, 2026

(54) THERAPEUTIC ELECTRICAL MUSCLE STIMULATION APPARATUS AND METHOD OF IMPROVING MEDICAL PROCEDURE OUTCOMES

(71) Applicant: LF Bolt Corp., Costa Mesa, CA (US)

(72) Inventor: Colleen McNutt, Costa Mesa, CA (US)

(73) Assignee: LF Bolt Corp., Costa Mesa, CA (US)

( * ) Notice: Subject to any disclaimer, the term of this patent is extended or adjusted under 35 U.S.C. 154(b) by 97 days.

(21) Appl. No.: 18/479,787

(22) Filed: Oct. 2, 2023

(65) Prior Publication Data

US 2024/0293663 A1 Sep. 5, 2024

Related U.S. Application Data

(60) Provisional application No. 63/412,356, filed on Sep. 30, 2022, provisional application No. 63/412,361, filed on Sep. 30, 2022.

(51) Int. Cl.
*A61N 1/04* (2006.01)
*A61N 1/36* (2006.01)

(52) U.S. Cl.
CPC ......... *A61N 1/0452* (2013.01); *A61N 1/0484* (2013.01); *A61N 1/3603* (2017.08)

(58) Field of Classification Search
CPC ... A61N 1/0452; A61N 1/3603; A61N 1/0484
USPC .......................................................... 607/48
See application file for complete search history.

(56) References Cited

U.S. PATENT DOCUMENTS

| | | | |
|---|---|---|---|
| 7,551,967 | B1 | 6/2009 | Karicherla et al. |
| 2005/0004436 | A1 | 1/2005 | Nissila et al. |
| 2005/0015118 | A1 | 1/2005 | Davis et al. |
| 2007/0179534 | A1 | 8/2007 | Firlik et al. |
| 2008/0319514 | A1 | 12/2008 | Shi et al. |
| 2016/0058335 | A1 | 3/2016 | Ashby |
| 2016/0114160 | A1 | 4/2016 | Scott |
| 2016/0213320 | A1 | 7/2016 | Shabah |
| 2017/0056644 | A1 | 3/2017 | Chahine et al. |
| 2017/0164832 | A1 | 6/2017 | Kalb et al. |
| 2017/0224985 | A1 | 8/2017 | Debur et al. |

(Continued)

FOREIGN PATENT DOCUMENTS

| | | | |
|---|---|---|---|
| CN | 112426624 | A | 3/2021 |
| EP | 2801389 | A1 | 11/2014 |

(Continued)

OTHER PUBLICATIONS

Mcnutt; U.S. Appl. No. 18/730,299 entitled "Electrical muscle stimulation apparatus and methods," filed Jul. 18, 2024.

(Continued)

*Primary Examiner* — Nadia A Mahmood
(74) *Attorney, Agent, or Firm* — Shay Glenn LLP

(57) ABSTRACT

Described herein are therapeutic electrical muscle stimulation (EMS) apparatuses for improving outcomes and reducing recovery time associated with a medical procedure. Also described are methods and apparatuses (including light-therapy suits, user interfaces, feedback systems and control systems, etc.), which may include hardware, software and/or firmware, for light therapy (LT) systems for the diagnosis, prevention, treatment, and detection of diseases and conditions, including symptoms associated therewith.

19 Claims, 11 Drawing Sheets

(56) References Cited

U.S. PATENT DOCUMENTS

| | | | | |
|---|---|---|---|---|
| 2018/0036531 | A1 | 2/2018 | Schwarz et al. | |
| 2018/0140901 | A1 | 5/2018 | Wiebe et al. | |
| 2019/0247650 | A1 | 8/2019 | Tran | |
| 2020/0188653 | A1* | 6/2020 | Dernebo .............. | A61N 1/0476 |
| 2020/0197689 | A1 | 6/2020 | Dernebo et al. | |
| 2020/0405188 | A1 | 12/2020 | Sharma et al. | |
| 2020/0405218 | A1 | 12/2020 | Avila et al. | |
| 2020/0406119 | A1 | 12/2020 | Woltermann | |
| 2021/0016087 | A1 | 1/2021 | Shahriari et al. | |
| 2022/0143393 | A1 | 5/2022 | Charlesworth | |
| 2025/0325800 | A1 | 10/2025 | McNutt | |

FOREIGN PATENT DOCUMENTS

| | | | |
|---|---|---|---|
| KR | 20130062858 | A | 6/2013 |
| KR | 101775506 | B1 | 9/2017 |
| WO | WO2007/138598 | A2 | 12/2007 |
| WO | WO2008/062395 | A1 | 5/2008 |
| WO | WO2022/061250 | A2 | 3/2022 |
| WO | WO2023/230637 | A2 | 11/2023 |
| WO | WO2023/250502 | A2 | 12/2023 |
| WO | WO2024/006755 | A2 | 1/2024 |

OTHER PUBLICATIONS

Mcnutt; U.S. Appl. No. 18/481,225 entitled "Therapeutic electrical muscle stimulation apparatus and method of treatment," filed Oct. 4, 2023.

Feng; Sensor Suits for Human Motion Detection; Report No. UCI-CEE-03-F03; California Univ. Irvine; 2006; 19 pages; retrieved from the internet (https://apps.dtic.mil/sti/pdfs/ADA444285.pdf).

Liegnell et al.; Validity of ultrasonography-derived predictions for estimating skeletal muscle vol. a systematic literature review; BMC medical imaging; 21(1); 106; 11 pages; Jul. 5, 2021.

Nakanishi et al.; Monitoring of muscle mass in critically ill patients: comparison of ultrasound and two bioelectrical impedance analysis devices; Journal of intensive care; 7(1); 61; 8 pages; Dec. 16, 2019.

Mcnutt; U.S. Appl. No. 18/878,640 entitled "Therapeutic electrical muscle stimulation apparatus and method of treatment," filed Dec. 23, 2024.

Mcnutt; U.S. Appl. No. 18/879,747 entitled "Optical sensing to detect muscle density in a wearable electrical muscle stimulation apparatus," filed Dec. 27, 2024.

* cited by examiner 101
103
109
117
105
107
115
113
121
119

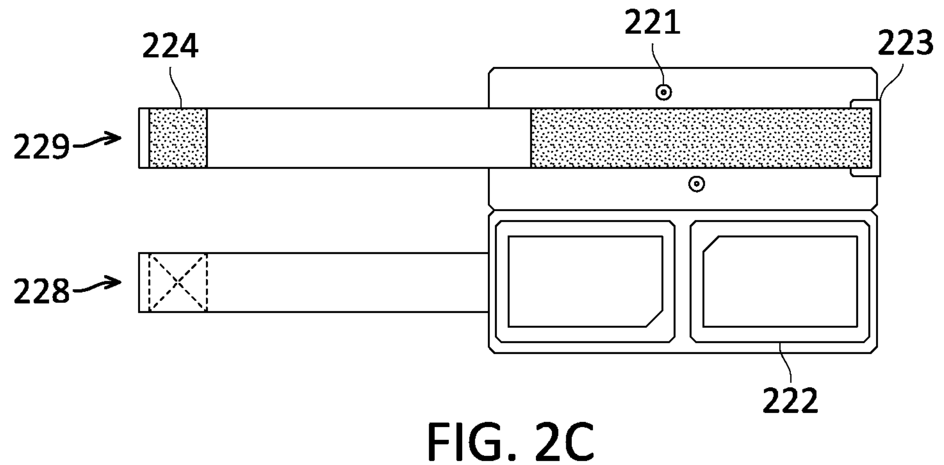
FIG. 2C
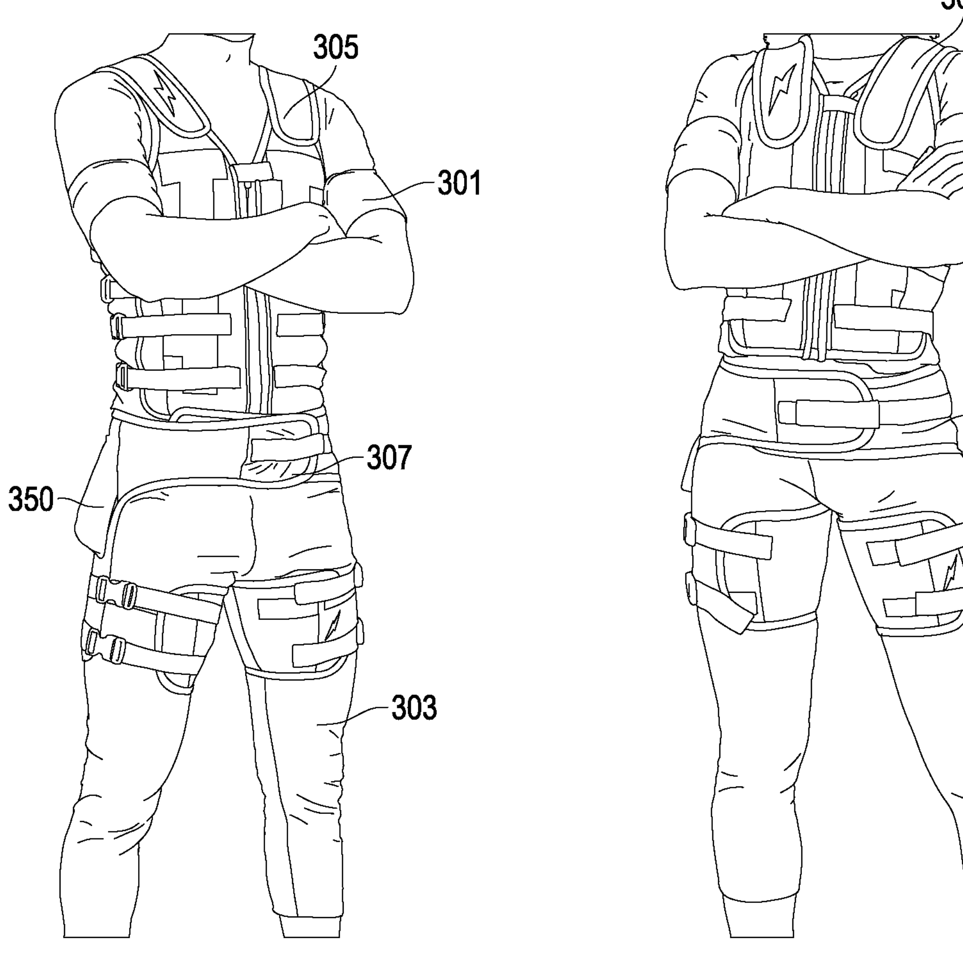
FIG. 3A
FIG. 3B

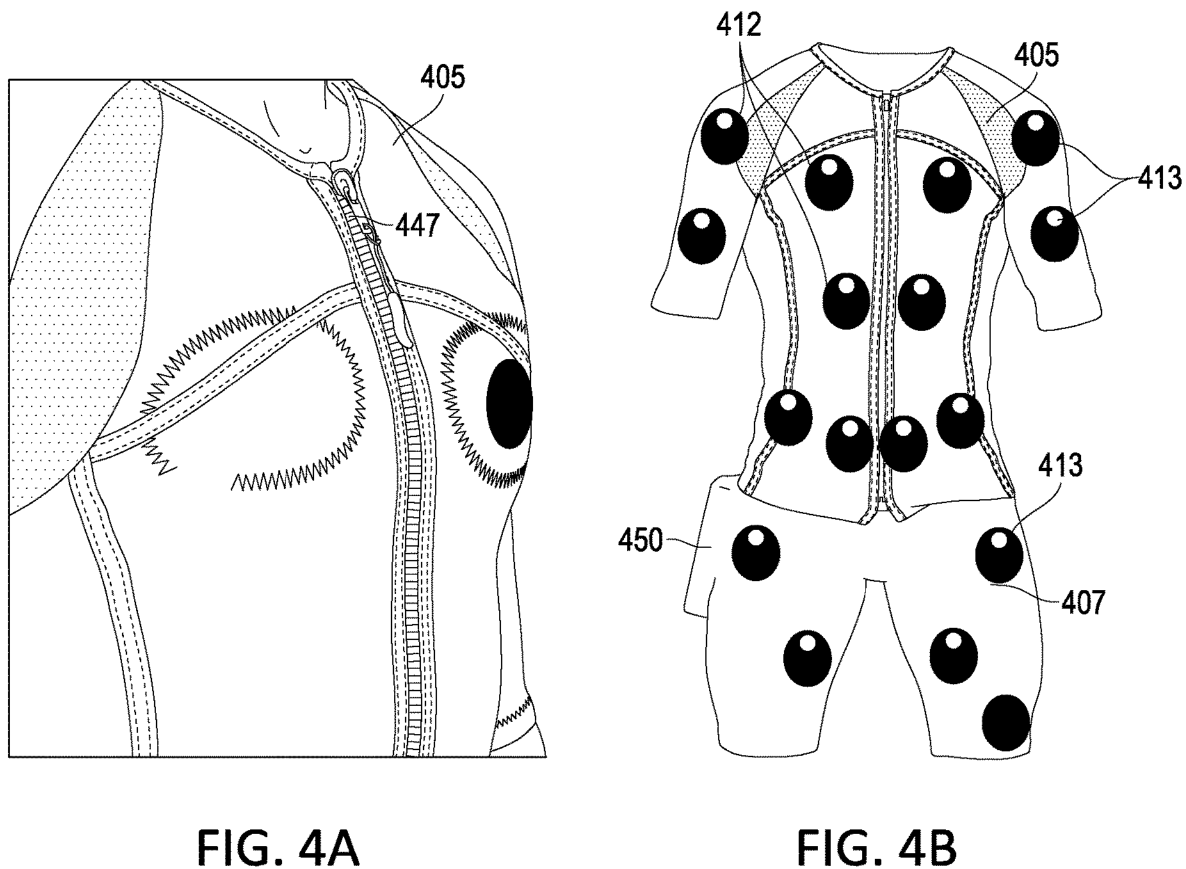
FIG. 4A
FIG. 4B
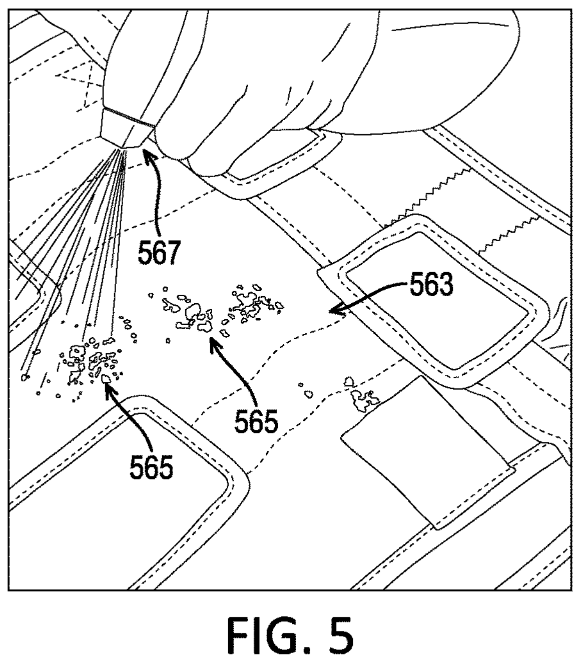
FIG. 5

THERAPEUTIC ELECTRICAL MUSCLE STIMULATION APPARATUS AND METHOD OF IMPROVING MEDICAL PROCEDURE OUTCOMES

CLAIM OF PRIORITY

This application claims the benefit of U.S. Provisional Patent Application No. 63/412,361, filed Sep. 30, 2022, titled "THERAPEUTIC ELECTRICAL MUSCLE STIMULATION APPARATUS AND METHOD OF IMPROVING MEDICAL PROCEDURE OUTCOMES," and U.S. Provisional Patent Application No. 63/412,356, filed Sep. 30, 2022, and titled "LIGHT THERAPY APPARATUS AND METHOD OF TREATMENT," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Invasive medical procedures are associated with long recovery times that are both physically and financially to the patient and the healthcare system at large. Physical insult to tissue during surgery can require weeks, months or more of intensive rehabilitative therapy to restore tone, circulation, and function of associated muscle groups. Patients are generally treated by extended hospitalization and repeat travel to rehabilitation facilities, in addition to the at-home activity as directed by a healthcare provider.

Sufficient preparation for a surgery is crucial to increase success and associated outcomes. Similarly, post-operative recover time can be dramatically reduced if patients adhere to strict therapy schedules, follow-up appointments, and continue rehab activities at-home. However, sub-optimal patient compliance is often a major factor requiring procedural compromises and extended recovery periods.

There are limited options available for rehabilitation support outside of a hospital setting and patients are often left to manage their recovery based on limited instruction and brief examples of physical therapy techniques they are expected to continue outside of the treatment facility. Beyond a voluntary lack of compliance, patients with pre-existing physical limitations are at a sever disadvantage for an expeditious recover.

Electrical muscle stimulation (EMS) may be a treatment option for some patients, but the associated hardware is restrictive with limited functionality or adaptability to user-specific needs. For example, adhesive electrodes require detailed understanding of anatomy and physiology associated with a surgery to provide any potential benefit. Current EMS systems prohibit physical activity during use fail to provide effective or sufficient stimulation to improve outcomes and reduce recovery time associated with surgery.

Even where current EMS may allow for adjustment of electrical intensity, there is still a failure to provide a patient-specific stimulation protocol that can be tailored to both the patient and a pending or recent invasive medical procedure.

Being able to increase patient compliance with an intuitive EMS system requiring minimal manual input and calibration prior to a surgery can dramatically reduce recovery time and improve overall procedural success. It is desirable to provide a system and method for optimizing tissue composition such as muscle tone, circulation and reduced inflammation prior to and/or after a surgery to improve the overall outcome of the procedure.

Continuously monitoring a patient for a sign or indication of a disease-related event can provide improved therapy. Beyond treatment, the methods and apparatuses described herein may address preventative, diagnostic and predictive shortcomings related to neurological disorders.

Light therapy involves the transmission of radiation energy from a light source to therapeutically, cosmetically, and/or otherwise modulate biological processes. Photobiomodulation is an example of non-ionizing light therapy including deployment of a light source to contact an exterior surface of a user. Current light therapy devices often include a pad that can be positioned over an affected and held in place or strapped to the user for the duration of treatment. Effective treatment with these devices can require extended treatment duration during several treatment sessions.

Where the light therapy is administered by a healthcare provider, a patient can be required to make several trips to a treatment facility and can introduce a substantial margin of error in the repeatability of treatment including placement of the light source during subsequent treatment. In some cases, patients may receive a tattoo for proper alignment of the light sources in subsequent treatments.

In addition to clear deficiencies in reproducibility of current light therapy systems, these devices generally provide radiation energy from the light source with a static wavelength and are incapable of optimizing the light energy attributes tailored to a particular patient. It would be most advantageous to provide a tailored treatment regime based on specific needs for a patient and/or optimizing the therapeutic potential based on a desired outcome from the therapy.

For these reasons, it would be desirable to provide improved devices, systems, and methods of light therapy. It would be particularly desirable to provide optimized treatment regimes, energy characteristics, and systems for easily reproducible application to a user. At least some of these objectives will be met by the various embodiments that follow.

SUMMARY OF THE DISCLOSURE

Described herein are apparatuses (including EMS suits, user interfaces, and control systems, etc.), which may include hardware, software and/or firmware, for electrical muscle stimulation (EMS) systems that may provide improved outcomes associated with an invasive medical procedure (e.g., surgery) including reducing a recovery time, decrease incidence of complications, and decrease scarring.

In general, a method for reducing recovery time after a medical procedure may include steps of positioning an electrical muscle stimulation (EMS) garment on a patient, the EMS garment can have one or more electrodes locatable in operable communication with one or more target muscle groups associated with a medical procedure. Then, establishing a stimulation protocol based on the medical procedure and supplying stimulation to the one or more target muscle groups via EMS power from the one or more electrodes.

In some examples, the EMS garment can comprise a torso portion, lower portion, head portion, or a combination thereof. In some examples, the one or more one or more electrodes can be disposed on an inner surface of the EMS suit apparatus, wherein the positioning can comprise wearing, by the patient, the EMS suit apparatus.

In some examples, stimulation can be supplied to the one or more target muscle groups for a treatment period prior to a surgical procedure.

In some examples, the medical procedure can be surgery, and the one or more target muscle groups selectively receive the supplied stimulation based on the surgery.

In some examples, the method further can comprise receiving patient biometric data from one or more sensors in operable communication with the EMS garment. In some examples, the method further can comprise updating the stimulation protocol based on the biometric data from one or more sensors, wherein the EMS power, duration, pattern, location, or a combination thereof can be updated based on the biometric data.

In some examples, the stimulation can be supplied to the one or more target muscle groups after the medical procedure. In some examples, the stimulation protocol can be configured to increase muscle tone of the one or more target muscle groups. In some examples, the stimulation protocol can be configured to increase blood flow to the one or more target muscle groups. In some examples, the stimulation protocol can be configured to decrease a recovery time between the medical procedure and sufficiently restored muscular function.

In some examples, the restored muscular function comprises a quantitative analysis of a range of motion, maximum voluntary contraction, muscle tone, or a combination thereof. In some examples, the stimulation protocol can comprise an increasing maximum suppliable EMS power based on the medical procedure or the duration between the medical procedure and first application of EMS. In some examples, the EMS power can be based on the medical procedure, a user provided input, a power level provided by clinician, or a combination thereof. In some examples, the EMS power can be adjustable based on biometric data acquired by one or more sensors in operable communication with the EMS garment.

In some examples, establishing the stimulation protocol comprising selecting a predetermined stimulation protocol based on the medical procedure, one or more target muscle groups, patient baseline biometric data, or a combination thereof. In some examples, the stimulation protocol can be adjustable by a controller.

In some examples, the method further comprises determining pre-procedure muscle characteristics via one of more sensors operably coupled to the EMS garment, the pre-procedure muscle characteristics based on at least muscle tone before the medical procedure. Then, determining post-procedure muscle characteristics via one or more sensors operably coupled to the EMS garment.

In some examples, the method further comprises updating the stimulation protocol based on the determined post-procedure muscle characteristics. In some examples, the stimulation can be supplied to the one or more target muscle groups before surgery, after surgery or a combination thereof.

In general, an electrical muscle stimulation (EMS) apparatus as an adjunctive treatment for surgical procedures, the apparatus can comprise an EMS garment configured to be worn by a patient after a surgical procedure, the EMS garment can comprise one or more electrical muscle stimulation (EMS) electrodes configured to make direct contact with a patient's skin proximate to a stimulation site based on the surgical procedure, one or more sensors can be configured to acquire patient biometric data, and a controller coupled to the sensor and configured to provide EMS power to the one or more EMS electrodes.

In some examples, EMS garment further comprises a first torso portion configured to be worn over the patient's torso and a lower portion configured to be worn over a lower portion of the patient including the patient's legs.

In some examples, the one or more sensors can be configured to provide patient biometric data before surgery, after surgery or a combination thereof. In some examples, the stimulation site comprises one or more target muscle groups associated with the surgical procedure.

In some examples, the one or more sensors comprise at least one accelerometer configured to provide patient movement data. In some examples, the controller is further configured to display positioning confirmation based on the position of the one or more EMS electrode position proximately to the stimulation site.

In some examples, the controller can be configured to provide EMS power based on initial patient biometric data, a user provided input, a power level provided by clinician, or a combination thereof. In some examples, the EMS power can be adjustable based on the acquired biometric data from the one or more sensors. In some examples, the EMS power can be configured to be adjusted based on a pre-determined stimulation protocol.

In some examples, the controller can be configured to adjust a stimulation protocol based on one or more changes in the acquired patient biometric data after the surgical procedure. In some examples, the controller can be configured to determine an increase in muscle tone of the patient and analyze recovery progression. In some examples, the controller can be configured to display an updated treatment plan based on the analyzed recover progression. In some examples, the EMS power is configured to decrease recovery after the surgical procedure.

In general, a method of preventing muscle atrophy can comprise establishing a stimulation protocol based on patient-specific data. Then, positioning an electrical muscle stimulation (EMS) garment on a patient, the EMS garment having one or more electrodes locatable in direct contact with the patient's skin. Then, supplying stimulation according to the stimulation protocol to one or more target muscle groups, via EMS power from the one or more electrodes.

In some examples, the stimulation is supplied prior to a surgical procedure. In some examples, the stimulation protocol is configured to decrease a recovery period after a surgical procedure.

In general the apparatuses and methods described herein may be used as part of a therapeutic or non-therapeutic procedure. For example, these methods and apparatuses may be part of an exercise or fitness (including weight loss) regime. However, the methods and apparatuses described herein may also or alternatively be used as part of a therapy, such as in particular for physiotherapy and/or for treatment of a condition or a disease.

In general, a therapeutic electrical muscle stimulation (EMS) apparatus for treatment of a user having a neurological disorder, the EMS device may comprise a wearable upper torso region with a detection system having one or more sensors configured to detect user-specific biometric data. Also, a processing unit operably coupled to the one or more sensors. The processing unit can be configured to interpret the user-specific data. An interface can be operably coupled to the processing unit, the interface can be configured to receive predetermined one or more predetermined user-specific attributes associated with the neurological disorder. A plurality of electrode assemblies on an inner surface of the upper torso region can be operably connected to the processing unit, wherein each of the electrode assemblies can be configured to supply a therapeutically effective amount of electrical stimulation based on the user-specific data.

For example, a method of treating a user for a neuromuscular disorder may include: receiving user movement data from one or sensors of an electrical muscle stimulation (EMS) suit worn by the user; detecting a neurological and/or neuromuscular indicator from the user movement data; applying, from one or more electrodes of the EMS suit a therapeutic treatment to the user.

Receiving may comprise receiving accelerometer data. In some examples receiving comprises receiving movement data having a frequency consistent with tremor in one or more body parts, e.g., the frequency may be greater than 2 Hz. In some examples the neurological and/or neuromuscular indicator is consistent with stroke. The neurological and/or neuromuscular indicator may be consistent with Alzheimer's disease. In some examples identifying and outputting a potential pathology associated with the neurological and/or neuromuscular indicator.

Also described herein are apparatuses. For example, a therapeutic electrical muscle stimulation (EMS) apparatus for treatment of a user having a neurological disorder may include: a wearable upper torso region comprising a detection system having one or more sensors configured to detect user-specific biometric movement data; a processing unit operably coupled to the one or more sensors, the processing unit configured to interpret the user-specific data to identify a neurological and/or neuromuscular indicator from the biometric movement data; and a plurality of electrode assemblies on an inner surface of the upper torso region each of the electrode assemblies operably connected to the processing unit, wherein each of the electrode assemblies configured to supply electrical stimulation, wherein the processing unit is further configured to apply, from one or more electrodes of the plurality of electrode assemblies a therapeutic treatment to the user based on the identified neurological and/or neuromuscular indicator.

Also described herein are apparatuses for diagnosing. For example, an electrical muscle stimulation (EMS) apparatus for diagnosis of a disease may include: a wearable upper torso region comprising a detection system having one or more sensors configured to detect user-specific biometric movement data; a processing unit operably coupled to the one or more sensors, the processing unit configured to interpret the user-specific biometric movement data to determine a disease profile; a plurality of electrode assemblies on an inner surface of the upper torso region each of the electrode assemblies operably connected to the processing unit, wherein each of the electrode assemblies configured to supply electrical stimulation; and an interface operably coupled to the processing unit, the interface configured to output a diagnostic comparison of the user-specific biometric data and the one or more disease profiles.

In some examples, the apparatus may also include comprising a controller that can be electrically connected the plurality of electrode assemblies, the controller can be configured to initiate EMS via the plurality of electrode assemblies according to an automatically adjustable stimulation regime based on the data. The one or more sensors may comprise at least one accelerometer that can be configured to detect a change in acceleration associated with the neurological disorder. The interface can be configured to communicate with one or more remote databases to acquire predetermined user-specific biometric data, wherein the therapeutically effective amount of electrical stimulation can be adjusted by the predetermined user-specific biometric data.

In some examples, the processor can be configured to establish one or more thresholds based on initial user-specific biometric data, wherein the initial user-specific biometric data can be acquired by the one or more sensors for a predetermined duration beginning with a first use of the EMS. Each of the one or more sensors can be associated with the plurality of electrode assemblies. A stimulation regime may define a duration, intensity, location, pulse pattern, or stimulation sequence, and wherein the stimulation regime can be configured to be automatically adjusted based on subsequent user-specific biometric data. The apparatus may also comprise a lower region that can be configured to confirm the user's legs and buttocks, the lower region may comprise one or more sensors configured to detect user-specific biometric data associated with a neurological disorder, wherein the one or more sensors are operably coupled to the processing unit; and a plurality of electrode assemblies can be configured to supply the therapeutically effective amount of electrical stimulation to the user's legs and buttocks based on the data. The user-specific biometric data can be associated with an incidence of a tremor.

In some examples, the user-specific data can be shared with the one or more remote databases, and wherein the therapeutically effective amount of electrical stimulation can be associated with a threshold configured to be adjusted based on one or more changes in the one or more remote databases. The therapeutically effective electrical stimulation can be automatically adjusted based on subsequent user-specific biometric data. The one or more sensors can include a plurality of sensors configured to acquire data associated with muscle tissue. At least one of the one or more sensors can be an electromyography sensor configured to predict a tremor, wherein biological electrical signaling can be detected before an involuntary muscle contraction. The neurological disorder can be Alzheimer's disease, Parkinson's Disease, Huntington's Disease, brain injury, spinal cord injury, autoimmune disease, restless leg syndrome, essential tremor, and a genetic neurological disease.

In some examples, the therapeutically effective amount of electrical stimulation can be sufficient to prevent or reduce involuntary muscle activity associated with the neurological disorder. The one or more sensors may comprise a plurality of sensors configured to detect user-specific data associated with respiration. The one or more sensors may comprise a plurality of sensors configured to detect user-specific data associated with body temperature. The one or more sensors may comprise a plurality of sensors configured to detect user-specific data associated with perspiration. Each of the one or more sensors can be integrated with the plurality of electrode assemblies. The user-specific biometric data may comprise a plurality of biometric characteristics obtained from more than one sensor. The processing unit can be configured to compare the interpreted data against one or more neurological disorder profiles.

In general, an electrical muscle stimulation (EMS) apparatus for diagnosis of a disease may comprise a wearable upper torso region comprising a detection system that may have one or more sensors configured to detect user-specific biometric data. A processing unit can be operably coupled to the one or more sensors. The processing unit may be configured to interpret the user-specific biometric data and compare the interpreted user-specific biometric data against one or more disease profiles. A plurality of electrode assemblies on an inner surface of the upper torso region each of the electrode assemblies can be operably connected to the processing unit, wherein each of the electrode assemblies configured to supply electrical stimulation, wherein the electrical stimulation can be at least effective to challenge biological tissue response. An interface can be operably coupled to the processing unit, the interface can be at least configured to present a diagnostic comparison of the user-specific biometric data and the one or more disease profiles.

In some examples, the apparatus may further comprise a controller electrically connected the plurality of electrode assemblies. The controller can be configured to initiate a diagnostic EMS challenge via the plurality of electrode assemblies. The one or more sensors may comprise at least one accelerometer configured to detect a change in acceleration associated with the disease. The interface can be configured to communicate with one or more remote databases to acquire one or more predetermined biometric factor ranges, wherein the processing unit is configured to compare the user-specific biometric data against the one or more predetermined biometric factor ranges.

In some examples, the processor can be configured to establish one or more thresholds based on initial user-specific biometric data, wherein a detected deviation in user-specific biometric data from the initial user-specific biometric data is associated with a disease. Each of the one or more sensors can be associated with the plurality of electrode assemblies. The user-specific data can be shared with the one or more remote databases, and wherein the therapeutically effective amount of electrical stimulation is associated with a threshold configured to be adjusted based on one or more changes in the one or more remote databases. The diagnosis of a disease can be based on the user-specific biometric data. The one or more sensors may include a plurality of sensors configured to acquire data associated with muscle tissue. One of the one or more sensors can be an electromyography sensor configured to detect a tremor. The diagnosed disease can be a neurological disorder.

In some examples, the one or more sensors may comprise a plurality of sensors configured to detect user-specific data associated with respiration. The one or more sensors may comprise a plurality of sensors configured to detect user-specific data associated with body temperature. Each of the one or more sensors can be integrated with the plurality of electrode assemblies. The user-specific biometric data may comprise a plurality of biometric characteristics obtained from more than one sensor. The processing unit can be configured to compare the interpreted data against one or more neurological disorder profiles to determine the diagnosis of the disease.

All of the methods and apparatuses described herein, in any combination, are herein contemplated and can be used to achieve the benefits as described herein.

Described herein are methods and apparatuses (including light-therapy suits, user interfaces, feedback systems and control systems, etc.), which may include hardware, software and/or firmware, for light therapy (LT) systems for the diagnosis, prevention, treatment, and detection of diseases and conditions, including symptoms associated therewith.

In general, the apparatuses and methods described herein may be used as part of a therapeutic or non-therapeutic procedure. For example, these methods and apparatuses may be part of photobiomodulation (PBM) regime. However, the methods and apparatuses described herein may also or alternatively be used as part of a cosmetic adjustment and/or therapy, such as physiotherapy and/or for treatment of a condition or a disease.

In general, a method of treating a user with a photobiomodulation system can comprise the steps of receiving user data from one or sensors of a photobiomodulation (PBM) suit worn by the user; detecting, by one or more sensors, one or more user-specific indicators; and applying, from one or more light source arrays of the PBM suit, a therapeutically effective light energy treatment to the user, wherein the therapeutically effective light energy may be based on the one or more indicators.

In some examples, the one or more user-specific indicators is associated with a disease or condition and the therapeutically effective light energy may be based on the one or more user-specific indicators. In some examples, the step of receiving comprises receiving pulse oxygen data. In some examples, the step of receiving comprises receiving user data from one or more remote devices.

In some examples, the step of applying comprises applying the therapeutically effective light energy treatment having wavelength configured to penetrate one or more biological tissues. In some examples, the wavelength can be between 400 nm and 1100 nm. In some examples, the one or more user-specific indicators can be a neuromuscular indicator consistent with a neuromuscular disease or condition. In some examples, the method can further comprise a step of identifying and outputting a potential pathology associated with the one or more user-specific indicators.

In general, a photobiomodulation (PBM) garment system can comprise an upper torso region comprising one or more light source arrays configured to transmit therapeutically effective light energy to a user; and a controller operably connected the one or more light source arrays, the controller can be configured to initiate a transmission of the therapeutically effective light energy via the one or more light source arrays according to a treatment regime.

In some examples, the therapeutically effective light energy comprises one or more wavelengths between 400 nm and 1100 nm. In some examples, the therapeutically effective light energy can comprise a wavelength between 600 nm and 700 nm. In some examples, the therapeutically effective light energy can comprise a wavelength between 800 nm and 900 nm. In some examples, the therapeutically effective light energy can comprise a wavelength between 900 nm and 1000 nm. In some examples, the therapeutically effective light energy can comprise one or more energy densities between 75 J/cm2 and 700 J/cm2.

In some examples, the treatment regime can comprise a duration, intensity, location, pulse pattern, or transmission sequence. In some examples, the treatment regime can be a predetermined treatment regimen based on a disease or condition. In some examples, the therapeutically effective light energy can comprise a wavelength effective to penetrate one or more biological tissues. In some examples, the treatment regime can be configured to prevent a disease or condition, wherein the therapeutically effective light energy can be configured to contact one or more tissues associated with the disease or condition.

In some examples, the one or more light source arrays can comprise one or more light emitting diodes (LEDs). In some examples, the one or more light source arrays can comprise a plurality of laser diodes. In some examples, the system can comprise a plurality of sensors configured to acquire user-specific data.

In some examples, the treatment regime can be based on user specific-data. In some examples, the system can comprise one or more sensors configured to acquire user-specific data, wherein the treatment regime can be adjustable based on the user-specific data. In some examples, the system can further comprise a lower region comprising one or more light source arrays configured to transmit therapeutically effective energy to the user based on the treatment regime. In some examples, the controller can comprise a user interface configured to adjust the treatment regime.

In some examples, the system can comprise a hood region coupled to the torso portion, the hood region comprising one or more light source arrays configured to transmit therapeutically effective light energy to the user's neck and head. In some examples, the hood region can comprise one or more light source arrays configured to transmit therapeutically effective light energy to a user's face.

In general, a therapeutic photobiomodulation (PMB) apparatus for treatment of a user having a disease or condition can comprise a wearable upper torso region comprising a detection system having one or more sensors configured to detect user-specific biometric data; a processing unit operably coupled to the one or more sensors, the processing unit configured to interpret the user-specific data to identify one or more indicators from the user-specific data; and a plurality of light emitting assemblies on an inner surface of the upper torso region each of the light emitting assemblies operably connected to the processing unit, wherein each of the light emitting assemblies can be configured transmit therapeutically effective light energy. The processing unit can be further configured to apply, from one or more light sources of the plurality of light emitting assemblies a therapeutic treatment to the user based on the identified one or more indicators.

In some examples, the processing unit comprises a controller electrically connected the plurality of light emitting assemblies, the controller configured to initiate PBM via the plurality of light emitting assemblies according to an automatically adjustable treatment regime based on the data. In some examples, the one or more sensors can comprise at least one oximeter configured to detect an oxygen level in blood.

In some examples, the interface can be configured to communicate with one or more remote databases to acquire predetermined user-specific biometric data, wherein the therapeutically effective light energy can be adjusted by the predetermined user-specific biometric data. In some examples, the processor is configured to establish one or more thresholds based on initial user-specific biometric data, wherein the initial user-specific biometric data can be acquired by the one or more sensors for a predetermined duration beginning with a first use of the PBM apparatus. In some examples, each of the one or more sensors can be associated with the plurality of light emitting assemblies.

In some examples, a treatment regime can comprise a duration, intensity, location, pulse pattern, or transmission sequence, and wherein the treatment regime can be configured to be automatically adjusted based on subsequent user-specific biometric data.

In some examples, the apparatus may further comprise a lower region that can be configured to confirm the user's legs and buttocks, the lower region comprising one or more sensors configured to detect user-specific biometric data, wherein the one or more sensors can be operably coupled to the processing unit; and a plurality of light emitting assemblies configured to supply the therapeutically effective light energy to the user's legs and buttocks based on the data.

In some examples, the user-specific data is shared with the one or more remote databases, and wherein the therapeutically effective amount of light energy can be associated with a threshold configured to be adjusted based on one or more changes in the one or more remote databases. In some examples, the therapeutically effective light energy is automatically adjusted based on subsequent user-specific biometric data. In some examples, the one or more sensors include a plurality of sensors configured to acquire data associated with circulatory system activity. In some examples, the one or more indicators comprises a prevention indicator, wherein the therapeutically effective light energy is applied based on a predetermined treatment regime.

In some examples, the therapeutically effective light energy can be sufficient to prevent or reduce oxidative stress associated with the disease or condition. In some examples, the one or more sensors can comprise a plurality of sensors configured to detect user-specific data associated with respiration. In some examples, the one or more sensors can comprise a plurality of sensors configured to detect user-specific data associated with body temperature. In some examples, the one or more sensors can comprise a plurality of sensors configured to detect user-specific data associated with perspiration.

In some examples, each of the one or more sensors are integrated with the plurality of light emitting assemblies. The user-specific biometric data can comprise a plurality of biometric characteristics obtained from more than one sensor. The processing unit can be configured to compare the interpreted data against one or more disease profiles.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 2A-2C show an example of parts of an EMS or LT apparatus.

FIGS. 3A-3B illustrate examples of EMS or LT apparatuses (e.g., EMS or LT suits) worn on a user.

FIGS. 4A-4B show another example of an EMS or LT apparatus as described herein.

FIG. 5 illustrates hydrating an example of an electrode for an EMS or LT apparatus.

DETAILED DESCRIPTION

Figures 1A, 1B, 1C, 1D, 1E, 1F:
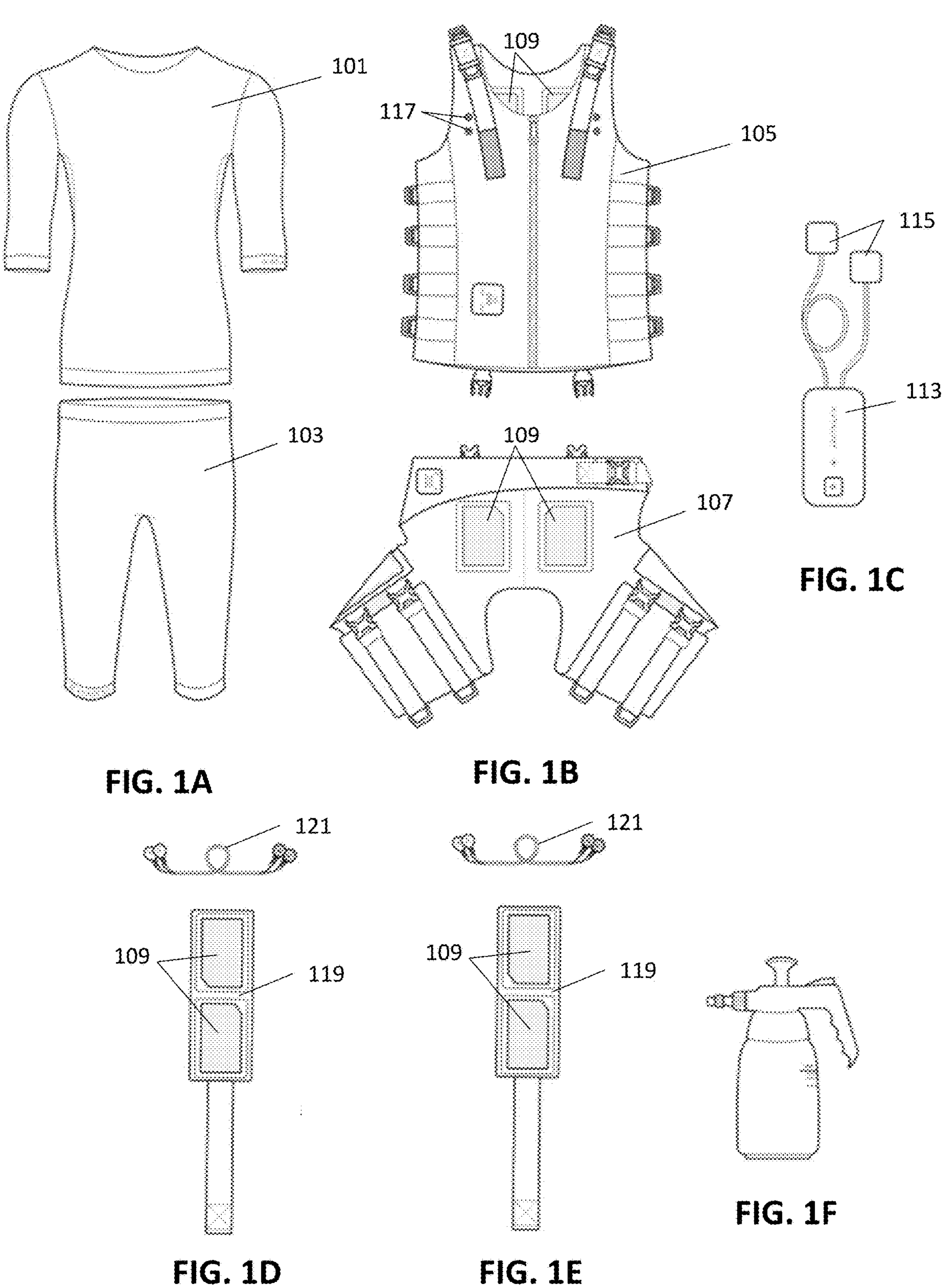
FIGS. 1A-1F show one example of an EMS or LT apparatus as described herein.

Described herein are electrical muscle stimulation (EMS) apparatuses (e.g., devices and systems, including suits, controls, operational protocols, etc.) including a therapeutic system for the improving outcomes of invasive medical procedures (e.g., surgery).

Pre-operative muscle condition can have significant impact on outcomes associated with invasive medical procedures. In some examples, decreased, reduced, sub-optimal, atrophied, or loss of muscle mass can negatively impact outcomes of surgery (e.g., invasive medical procedures). Invasive medical procedures, including minimally invasive procedures can be associated with physical changes to a patient's anatomy. For example, invasive procedures can include any procedure associated with a physical intervention (e.g., incision) on one or more biological tissues.

The EMS apparatuses may include a plurality of structural elements adapted to acquire user-specific data related biological tissue characteristics (e.g., composition). For example, the user-specific data can include data related to muscle tissue associated with a surgical site, in advance of an invasive medical procedure. The structural elements may include sensors associated with the EMS apparatus and configured to obtain user-specific data before, during and/or after use that may can be used to establish a treatment protocol (e.g., stimulation protocol) to modify biological tissue characteristics in advance of an invasive medical procedure. In some examples, the treatment protocol may be adapted to decrease recovery time after the procedure (e.g., surgery), increase wound healing, decrease scarring, decrease procedure-related atrophy, increase muscle tone, increase muscle mass, increase muscle area, etc., or a combination thereof.

Each of the sensors may be configured to receive or acquire data that may be interpreted by the therapeutic system and used in the preparation of a surgical site in advance of an invasive medical procedure. For example, the sensors may detect or acquire biometric data associated with the user.

In some examples, the therapeutic system may include an interface operably connected to the therapeutic system and configured to receive one or more inputs relating to the user. For example, the user interface may receive user input to generate a profile of the user that may adjust parameters of the therapeutic system (e.g., the sensors). In some examples, the interface may be in communication with one or more databases or electronic systems having data generated or established outside of the EMS apparatus, which may be incorporated into the therapeutic system operations. For example, the interface may communication with one or more electronic medical record systems having user-specific information such as medical history, lab test results, examination notes, or other relevant information related to a disease or condition, or risk factor thereof. The therapeutic system may interpret this remote user-specific information and adjust one or more of the sensors or one or more parameters for the sensors operation to target sensor operation based on the remote user-specific information.

In some examples, the stimulation (EMS) apparatuses may include one or more sensors configured to acquire and/or generate data and information within the apparatus to detect, diagnose, prevent, and/or treat a patient in advance of an invasive medical procedure (e.g., surgery) based on user-specific characteristics. The sensors may utilize various techniques to acquire biological and physiological information (e.g., muscle characteristics) from a user. For example, the sensors may be configured to detect muscle characteristics (e.g., tone, area, mass, density, etc.) that may be interpreted by the EMS apparatus (e.g., via a therapeutic system) and used in determining, establishing, and/or executing therapeutic stimulation protocols based on the detected characteristics.

In some examples, an EMS apparatus as described herein may include one or more sensors to acquire user-specific biometric data related to the incidence of a tremor. For example, one or more sensors may include an accelerometer to determine movement (e.g., acceleration) on a macro or micro scale. The EMS apparatus (e.g., EMS suit) may include one or more accelerometer sensors located or locatable within, on and/or associated with the EMS suit to sufficiently operate and detect user-specific data. An accelerometer sensor (e.g., an accelerometer) may be configured to sense changes in acceleration of the user at an area or region of the user's anatomy and/or the user's entire body. The detected changes may include a ratio of change or changes in acceleration from a steady state of movement to a deviation movement. A steady state of movement may include no movement (e.g., sedentary) or movement that is associated with natural or native biomechanical operation of a user's anatomy (e.g., biological tissue such as musculature). The accelerometer sensors may include one or more inertia measuring units (IMUs) configured to detect or acquire user-specific data associated with the inertia of the user's anatomy.

In some examples, the accelerometer sensors may be configured to detect a symptom of a disease or condition (e.g., sarcopenia, atrophy, etc.). Detection by the sensor may include acquiring data by the sensor that is interpreted by the EMS apparatus (e.g., the therapeutic system).

In some examples, the EMS apparatus may supply electrical stimulation via one or more electrodes as described herein. For example, a stimulation regime may be established based on the sensor data or interpretation of the sensor data including stimulation parameters such as stimulation intensity, duration, anatomic location, sequence, etc. In some examples, the stimulation regime may be adjustable based on subsequent data acquired by one or more of the sensors associated with the EMS apparatus (e.g., EMS suit). In some examples, the adjustment is dynamic and may increase or decrease or a combination in increase and decrease one or more of the stimulation parameters based on the subsequently acquired data. For example, an initial stimulation regime may be established based on the detection of a tremor and, after a period of time additional data may be acquired associated with persistence of the tremor that may cause the stimulation regime to change one or more of the stimulation parameters. In some examples, the stimulation regime may terminate after a therapeutically effective stimulation has been supplied.

One or more of the sensors may include a thermal sensor configured to detect biometric data related to the internal and/or external temperature of a user. Body temperature may be a factor related to determining the characteristics, condition, composition, etc. of biological tissues involved in an invasive medical procedure. The thermal sensors (e.g., temperature sensors) may be located or locatable on the EMS apparatus to acquire or detect the temperature of the user via contact, infrared sensing, etc. The data may then be sent to the processing unit for interpretation and analysis according to any of the processes described herein.

One or more of the sensors may be adapted to detect user-specific biometric data associated with respiration. For example, respiration volume, cadence, pulse oxygen levels, etc may be detected by the one or more respiration sensors. In some examples, the respiration sensors may include sensors associated with the EMS suit that detect a change in volume as the user inhales. For example, resistance sensors positioned throughout the suit may detect a strain on the EMS suit as the user inhales. The quantity of strain detected may be interpreted in one or more algorithms adapted to quantify the volume and rate of respiration. The respiration sensors may also include an optical element configured to detect pulse oxygen through optically sensing a flow of blood through one or more blood vessels associated with the sensor.

One or more of the sensors may include an electromyography sensor configured to detect electrical events associated with muscle function. Electromyography sensors may detect or acquire user-specific data associated with the function of a muscle and may be configured to predict voluntary, involuntary or a combination of involuntary and voluntary muscle function.

Detection of user-generated electrical signaling may provide data related to the incidence or prediction of an impending disease-associated biological activity. For example, the electromyography sensors may detect impulses from the nervous system to one or more biological tissues related to biological activity simultaneously, or prior to the incidence. The data may be interpreted by the processing unit and may be a factor in supplying electrical stimulation to optimize biological tissues associated with a surgical site. For example, treatment incorporating electromyography sensor data may provide support for stimulation parameters and supplying of EMS by the one or more electrodes.

The muscle characteristics may relate to the form and/or function of one or more muscle groups, muscles, or regions of muscle. One example of a muscle characteristic can be muscle density. The muscle characteristics may be entirely acquired by the sensors. In some examples, elements of a muscle characteristic may be acquired by the sensors and input into one or more algorithms adapted to calculate or quantify a muscle characteristic including the acquired data. In some examples, a quantification of muscle density may relate to a ratio of muscle to non-muscle tissue across or throughout an area of a user's body. In some examples, a quantification of muscle density may relate to a ratio of lean muscle to other tissue across or throughout an area of a user's body. In some examples, a quantification of muscle density may relate to a ratio of muscle tissue (e.g., muscle fiber) concentration within, across or throughout a user's body.

In general, an EMS apparatus may include an EMS suit having one or more sensors coupled or couplable thereto. Sensors may be associated with the EMS suit in a configuration allowing for associated operation of the sensor to acquire data and information. The sensors may be operably connected to the EMS suit and/or associated with one or more elements associated with the EMS suit (e.g., electrical circuitry, electrodes, controller, processor, power supply, etc). Each sensor may operate independently or in combination with one or more other sensors or EMS suit elements to acquire and/or determine user-related attributes (e.g., muscle characteristics) and transmit the user-related attributes to the EMS system associated with the system for stimulation and/or stimulation regime management.

The EMS apparatuses, as described herein, may include optical sensors configured for measuring user-specific muscle characteristics. Optical sensors may be located or locatable on the EMS suit. The location or disposition of the optical sensors may be based on target areas of the user subject to analysis. Optical sensors may be located on the EMS suit in a position exterior of the user and proximal to a muscle group. For example, the psoas muscle is located in the lower lumbar region of the spine and extends through the pelvis to the femur. Optical sensors configured to acquire muscle density of the psoas muscle may, therefore, be correspondingly positioned on the EMS suit at or near the anatomical location of the psoas muscle.

Optical sensors may operate based on the transmission of light modified by one or more body tissues (e.g., muscle tissue). Muscle characteristics may be determined or determinable based on the changes in light emitted from the optical sensors. Changes in light may relate to changes or modifications in one or more attributes of the light emitted by the optical sensors. The emitted light is received by the optical sensors after being transmitted. Changes in the received light may relate to or be appreciated as an impact of the light contacting a user's anatomy (e.g., muscle tissue). The changes in the emitted light may relate to one or more optical properties of biological tissues. Some examples of optical properties may include absorption, refraction, reflection, and scattering of light. Optical properties may relate to determinable characteristics of the tissue contacted by the emitted light.

In some examples, changes in the emitted light may include refraction of the light passing through the user's anatomy. For example, a change of the emitted light may be a function of a refractive index (RI). RI is a characteristic optical variable that controls the propagation of light in the medium (e.g., biological tissues). A measurement of RI of a biological tissue (e.g., muscle tissue), can be associated with the density of the tissue as a factor of the change in velocity of the light passing through it. For example, one or more of the optical sensors of the EMS apparatus, described herein, may emit light with an initial velocity through one or more layers of tissues of the user's body. When the light passes through a layer of tissue, an initial velocity can be observed by the optical sensor and a modified velocity may be observed based on the change in velocity as the light passes through each layer of tissue. Considering muscle tissue, the optical sensors may emit light that can penetrate the user's skin and continue through the skin to muscle tissue, where the light has a velocity at a point of initial contact with the muscle tissue. The velocity of the light may change (e.g., decrease) as the light passes through the muscle tissue and the change in velocity can be acquired by the optical sensors. In some examples, changes in the emitted light may be observed or acquired by the optical sensors at different intervals of distance (e.g., the depth of penetration) and/or time.

In some examples, the optical sensors described herein are adapted to acquire scattered light as a result of the emitted light contacting one or more biological tissues (e.g., muscle tissue). Scattered light analysis by the EMS apparatus described herein may relate to the impact of a biological tissue on emitted light causing light particles to scatter upon contact with various tissues structures (e.g., cells, fibers, extracellular matricies, etc.). For example, the light emitted by an optical sensor transmission element may have initial light attributes (e.g., wavelength, frequency, intensity, etc.). As the emitted light contacts or engages biological tissue (e.g., muscle tissue or muscle fibers), particles from the emitted light may be scattered by the tissue and the optical sensors may acquire or sense the scattered light particles. Attributes of the acquired scattered light (e.g., vectors, reflection angles, velocity, quantity, concentration, etc.) may provide data input for quantification of one or more characteristics of the biological tissue (e.g., density of muscle tissue).

In some examples, the optical sensors described herein are adapted to acquire information or data related to the reflection of light emitted into or through biological tissue (e.g., muscle tissue). For example, an optical sensor may emit light that is reflected by one or more layers of biological tissue. The reflected light may be acquired or sensed by the optical sensors and data or information such as the angle of reflection, velocity, duration, and other optical properties may be interpreted by the EMS apparatus described herein. Reflection of the emitted light may provide different modifications of the light based on the biological tissue impacting the reflection. For example, muscle tissue may reflect light differently, or the same, as dermal tissue or interstitial tissue. The EMS system can interpret the sensor data to determine specific tissue characteristics (e.g., muscle density).

In some examples, an EMS suit (e.g., an EMS apparatus) may include more than one optical sensors having a transmission element and each transition element may be configured to emit light having attributes unique to the associated transmission element. The unique light attribute values may be interpreted by one or more receiver elements of the optical sensors and incorporated into the data received by each receiver element to distinguish the location of the associated transmission element from which the light was emitted. For example, a first light may be emitted by an optical sensor transmission element having initial light attributes X and penetrate the user's body. After the light contacts one or more biological tissues (e.g., muscle tissue) and particles of initial light attribute X may become scattered and change to attributes Y that can be sensed by optical sensors. The difference of attributes X and attributes Y can be processed within the EMS apparatus (e.g., by the processing unit) to calculate muscle characteristics. The calculated muscle characteristics may then be incorporated into EMS apparatuses and a stimulation regime may be established whereby stimulation is supplied based on the muscle characteristic data.

In some examples, the optical sensors include a transmission element and a receiver element. The transmission element and receiver element may be incorporated into a single sensor unit. The transmission element may be capable of emitting light into or through one or more tissues of the user's body. The receiver element may be capable of receiving light after the light has contacted or otherwise been modified by the one or more biological tissues (e.g., the user's muscle tissue).

In some examples, the light emitted by the optical sensors is a laser light or other form of light adapted to sufficiently penetrate biological tissues (e.g., muscle tissue) for analysis of sensing by the optical sensors and EMS apparatus (e.g., EMS suit).

The EMS apparatus, as described herein, may include one or more bioelectrical sensors to evaluate bioelectric characteristics of biological tissue (e.g., muscle tissue). For example, impedance of the electrical impulse or energy emitted into the biological tissues of the user may related to biological characteristics of the tissue (e.g., muscle tissue). Some examples of bioelectrical sensors may include a transmission element and a receiver element. A bioelectrical sensor transmission element may emit an electrical pulse into, through, across or throughout body tissue of a user. The emitted electrical pulse may penetrate through one or more biological tissues and be modified the composition, orientation, location, type, arrangement, etc. of the biological tissue. For example, muscle tissue density may provide different modifications based on an increased density or a decreased density.

In some examples, the bioelectrical sensors may include a transmission element and a receiver element. The transmission element may be configured to transmit an electrical impulse into, through, and/or across one or more biological tissues. The receiver element may be configured to receive the transmitted electrical impulse after it has contacted or otherwise been modified by one or more biological tissues (e.g., muscle tissue). In some examples, the electrical impulse from the sensor may be modified from initial attributes at the time the impulse is transmitted or emitted from the sensor. The difference in the received impulse may be incorporated or appreciated by the EMS apparatus to determine or calculate a muscle characteristic that can be used to determine and establish the stimulation regime. For example, where a muscle is more dense, the impedance may be greater. The receiver element may accordingly acquire or sense the change in electrical pulse related to increased muscle density and adjust or establish stimulation parameters based on the sensor data.

In some examples, the sensors are ultrasonic sensors having a transmission element and a receiver element. The ultrasonic sensors may be adapted to emit sound of an initial frequency and wavelength into, across, or through one or more biological tissues. The receiver element may be configured to receive the transmitted ultrasonic waves after they have contacted or otherwise been modified by one or more biological tissues (e.g., muscle tissue). In some examples, the ultrasonic waves from the sensor may be modified from initial attributes at the time the ultrasonic waves are transmitted or emitted from the sensor. The difference in the received ultrasonic waves may be incorporated or appreciated by the EMS apparatus to determine or calculate a muscle characteristic that can be used to determine and establish the stimulation regime. For example, where a muscle is more dense, the ultrasonic waves may be decreased or reduced after contacting or passing through the muscle tissue. The receiver element may accordingly acquire or sense the change in ultrasonic waves related to increased muscle density and adjust or establish stimulation parameters based on the sensor data.

In some examples, the sensors coordinate with each other to combine or compile data acquired thereby. The sensors may communicate sensor data and sensor attributes such as sensor location and sensor parameters to compile and/or combine data to be interpreted by the EMS apparatus in the establishment, determination and/or adjustment of the stimulation regime. For example, sensors on the chest of the EMS suit, may communicate information of the pre-determined location, targetable muscle groups, and biological tissue characteristics. In some examples, the energy (e.g., light, sound, electricity, etc.) may be emitted by a first sensors and received by a second sensor. The second sensor may be the same sensor or different sensors. The second sensor may be the same type of sensor as the first sensor or may be a different type of sensor than the first sensor. For example, a first sensor may emit some type of energy on an anterior side or portion of the user that passes through biological tissues to be received on a posterior side or portion of the user.

In some examples, the EMS apparatus described herein may include a processing unit operably coupled to the sensors. The processing unit may be adapted to interpret the data or information acquired or sensed by the sensors. For example, the processing unit may be adapted to incorporated sensor data into one or more algorithms for the quantification of a tissue characteristic (e.g., muscle tissue density). In some examples, the processing unit may be adapted to include one or more coefficients for the interpretation of the sensor data. In some examples, the coefficients are predetermined based on known quantitative analysis of optical properties of the biological tissues (e.g., muscle tissue). In some examples, coefficients, as described herein, may be established based on training the algorithms over a period of time beginning with the user engaging the EMS suit. For example, a user may engage the EMS suit and the sensors may begin to acquire data from one or more sensors. The data may be interpreted into an initial algorithm that is modified over a period of time until sufficient calculations provide for a user-specific coefficient that can be applied to subsequent user engagement.

The stimulation regime or treatment protocol may be developed or established based on the interpretation of sensor data. Stimulation intensity, duration, arrangement, frequency, etc. may be modified based on the sensor data or interpretation of the sensor data by the EMS apparatus (e.g., the processing unit). For example, the optical sensors may obtain data related to the optical characteristics of muscle tissue contacted by light emitted from an optical sensor. The optical characteristic may provide data for determining the muscle density of the user and the muscle density value may provide for a user-specific modification to the stimulation regime. The stimulation regime may provide for increased intensity, higher frequency, shorter pulse duration, for muscle tissue that is more dense. Each factor or aspect of the stimulation regime may be adapted to the user-specific muscle characteristics to provide optimal stimulation of one or more muscles. In some examples, the stimulation regime may be more intense or less intense based on optimized electrical stimulation for the sensed muscle characteristics. Another example may include the bioelectrical sensors obtaining data related to the bioelectrical characteristics of muscle tissue contacted by electrical pulse emitted from a bioelectrical sensor. The bioelectrical characteristic may provide data for determining the muscle density of the user and the muscle density value may provide for a user-specific modification to the stimulation regime.

In some examples, the stimulation parameters of a stimulation regime may be adjusted by sensor data while the user is engaging the EMS apparatus. Sensors may continuously acquire data over a period of time and the data may result in adjustments to the stimulation regime or parameters of the stimulation regime or both. For example, sensed increased in muscle density may increase stimulation parameters to increase the stimulation supplied by the electrodes.

The EMS apparatuses may include an integrated controller and power supply, including an integrated controller and power supply with a user input/output (e.g., touchscreen) that is compact and may be coupled to an EMS suit for controlling the suit and/or for communicating with one or more remote servers. Also described herein are EMS apparatuses having wettable electrical contacts that are adapted for reliable and easy use by the wearer of the suit (e.g., in an at-home or studio setting). Also described herein are EMS suit apparatuses that are easier to put on, adjust and maneuver in than traditional EMS suits, and may allow movement and flexibility while maintaining reliable and sufficient contact between the user and the multiple EMS electrodes. Any of the apparatuses described herein may include a user interface configured to enhance the case of operation and effectiveness of an EMS suit. For example, described herein are apparatuses (e.g., systems) that may be used to regulate the safe and effective operation of the EMS suit, including limiting or preventing operation in ways that may be less effective and/or dangerous to the user.

In some examples, one or more sensors acquire data to be incorporated into an algorithm for computing one or more user-specific muscle properties. For example, one or more of the sensors may acquire dimensions of a muscle based on the changes in energy (e.g., light, sound, ultrasonic vibrations, etc.) from the transmission element to the receiver element after the energy has been modified based on contact with muscle tissue. Initial values or attributes of the energy signal transmitted into and/or through the tissue of the user may be different that the terminal values or attributes of the energy received by the receiver element. The different in energy attribute values may be input to an algorithm adapted to generate one or more functional values used in development and/or execution of the stimulation regime (e.g., the duration, intensity, sequence, stimulation arrangement, etc). For example, muscle thickness and/or muscle density may be a muscle characteristic relating to the stimulation regime. A transmission element of a sensor may emit a signal through the user's dermal layers until the first incidence of the signal contacting the muscle tissue. At the first incidence of contact, the signal may be changed distance from sensor to beginning of the muscle tissue and the is the (time elapsed from the sensor sending then receiving a sound/energy pulse X the speed of sound)/2.

In general, an EMS apparatus may include an EMS suit having a plurality of electrodes coupled or couplable thereto, wherein the electrodes are positioned/positionable on the EMS suit in an arrangement that provide muscle stimulation while preventing dangerous (e.g., transthoracic flow) of electrical current through a body of a user wearing the EMS suit during operation of the EMS suit. Individual electrodes of the EMS suit may be controllable by a processor(s) to deliver electrical impulses to muscles of a user who is wearing the EMS suit. In some examples, the processor controls the electrodes based on data and information received from the sensors. When an electrical impulse is delivered via a pair of electrodes, electrical current (i.e., the flow of charged particles) flows from one electrode (of the pair), through a portion of the user's body (e.g., through muscle tissue underlying the pair of electrodes), and to the other electrode (of the pair). The user's body completes an electrical circuit that includes the pair of electrodes, thereby allowing electrical current to flow between the pair of electrodes during operation of the EMS suit, as electrical impulses are delivered via the electrodes. A pair of electrodes may include two electrodes that correspond to a common channel of multiple channels that are used to deliver electrical impulses, channel-by-channel, during operation of the EMS suit. A pair of electrodes may also include two electrodes that allow for electrical current to flow therebetween during operation of the EMS suit, one electrode of the pair operating as a positive electrode (anode) and the other electrode of the pair operating as a negative electrode (cathode). With alternating current (AC), each electrode of a given pair may reverse current with each cycle (or frame). That is, each electrode may change from a positive electrode (anode) to a negative electrode (cathode) with each cycle (or frame).

For example, FIGS. 1A-1F illustrate an example of an EMS system as described herein. This example shows a wireless, whole-body electrical muscle stimulation (EMS) system that includes a suit/vest, a lower body (pants/shorts) portion, a combined power supply/controller/user interface, and an electrode wetting source (e.g., spray bottle). FIG. 1A shows an example of an upper 101 and lower 103 under suit. The under suit may be configured to allow electrical connection between electrodes and the underlying skin in the appropriate region of the body (e.g., over the target muscle groups). For example, the under suit may include openings and/or electrically conductive regions (or may be wholly conductive). The under suit may be configured to conform to the patient's body, e.g., as a stretch and/or compression garment. The under suit may be washable.

FIG. 1B shows an example of an upper torso (e.g., vest) portion 105 of the EMS suit and a lower body 107 portion of the EMS suit. The upper torso portion and the lower body portion may support the plurality of electrodes 109, which may be integrated into the apparatus. These electrodes, as described in greater detail below, may be wettable electrodes adapted to be easily wetted by the user. The upper torso and lower body portions may include one more adjustable straps allowing the user to attach and adjust the fit. The upper torso 105 portion shown in FIG. 1B is configured as a vest, and the lower body region is configured as a chaps-like configuration to be worn over the under suit. In some examples the under suit and the upper torso and lower body regions may be integrated together into a single garment, as shown in FIGS. 4A-4B, below.

In any of these examples the EMS suit may have electrodes strategically positioned so as to apply EMS to the target muscle groups, such as the quadriceps (quads), hamstrings, glutes, abs, chest, lower back, mid back, upper back (trapezius), biceps and triceps, and/or calves.

In any of these examples, the electrical connectors (e.g., "cables") may be integrated into the suit. For example, coupling the power supply/controller into the suit may automatically couple the electrodes to the power source/controller via a single (e.g., multiplexed) connection, dramatically simplifying the contact. For example, the integrated electrical connectors may be coupled via internal cabling that is arranged so as not to limit freedom of movement.

The electrodes of the EMS suit may be arranged in the EMS suit to cover parts of the user's body in order to excite particular muscle groups (e.g., arms, legs, chest, abdominals, back, etc.) through the delivery of electrical impulses that stimulate the muscle tissue beneath the user's skin. In particular, as will be described in greater detail below, the electrodes described herein may be arranged in a manner that increases the ability of the electrodes to remain in reliable communication with the patient's skin and therefore provide energy to the underlying muscle during a treatment.

For example, upper body portion (e.g., torso, including chest, vest, etc.) may be worn on an upper trunk of the user's body. The upper body portion may be coupled to the lower body portion, e.g., via one or more mechanical and/or electrical connectors. Thus any of the buckles/straps shown may include both mechanical and electrical connectors.

In any of these apparatuses the connectors 111 (e.g., buckles) may be configured to make and/or confirm electrical connection. For example, the power source/controller may sense and/or confirm that each connector is coupled and/or secured. The controller may, for example, provide a test current/pulse to confirm the electrical connection (via. the electrical properties of the connection, showing an open circuit if not properly attached). The electrical contact with the skin of the user may similarly or additionally be confirmed by the system and may be used as part of a safter interlock and/or power-saving protocol.

In some examples the upper body portion may comprise a left front portion, a right front portion, and a back portion. In some embodiments, the left front portion has a first pair of electrodes positioned on an inner surface of the left front portion and within a top half of the left front portion, while the right front portion has a second pair of electrodes positioned on an inner surface of the right front portion and within a top half of the right front portion. In this manner, when the body of a user is wearing the EMS suit, the first pair of electrodes may be disposed on (or atop) one or more left pectoral muscles of the body, and the first pair of electrodes may, therefore, be positioned on a first (e.g., left) side of a midsagittal plane of the body, as well as on a first (e.g., front) side of the frontal plane of the body. A second pair of electrodes may be disposed on (or atop) one or more right pectoral muscles of the body, and the second pair of electrodes may be positioned on a second (e.g., right) side of the midsagittal plane of the body, as well as on the first (e.g., front) side of the frontal plane of the body.

Electrical impulses may be delivered by the respective pairs of electrodes so that the flow of electrical current is primarily passed between each pair of electrodes, though the target muscle region, so that electrical current does not flow between an electrode of the first pair of electrodes and an electrode of the second pair of electrodes, or any other pair, in order to avoid applying electrical energy to regions that are not intended to be stimulated. For example, the apparatuses described herein may prevent electrical current from flow across the midsagittal plane of the user's body in a region of the thoracic cavity during operation of the EMS suit.

FIG. 1C also illustrates an example of an integrated controller/power supply 113. In this example, the integrated power supply/controller includes a separate mechanical and electrical connector; however in some examples the same connector may make both mechanical and electrical connection with the EMS suit. For example, in FIG. 1C the apparatus includes a pair of electrical connectors 115 that may attach to electrical coupling contacts on the suit. In FIGS. 1A-1F only a single pair (e.g., anode/cathode) of connectors are shown. In some examples, multiple connectors/contacts may be used. In this example the suit may include an integrated multiplexing electrical manifold that may direct and/or switch the applied energy to the one or more pairs of electrodes to which power is to be applied to apply EMS. In general, power may be applied to individual pairs of electrodes at a time (sequentially) or in a manner so that nearby electrodes in communication with the body are not concurrently activated by the application of electrical energy. The power supply/controller 113 may be held to the EMS suit by a pocket and/or a mechanical connector such as Velcro, straps, etc. Multiple mechanical connectors may be included.

FIGS. 1D and 1E illustrate examples of arm electrode supports 119 including electrodes 109 that may be used to apply electrical energy to the biceps and/or triceps. In this example, in which the arm electrode supports are not integral with the upper/torso portion 105, addition external cables 121 may be used to connect the arm electrodes to contact 117 on the upper/torso portion (vest) 105. Alternatively in some examples the electrode and/or electrode supports may be integrated into an upper/torso EMS garment.

In any of these apparatuses, the back of the upper body portion of the EMS suit may include multiple electrodes 109, including, e.g., a third pair of electrodes positioned on an inner surface of the back portion and within a left half of the back portion, and a fourth pair of electrodes positioned on the inner surface of the back portion and within a right half of the back portion. When the body of a user is wearing the EMS suit, the third pair of electrodes may be disposed on (or atop) one or more left back muscles of the body, and the third pair of electrodes may, therefore, be positioned on the first (e.g., left) side of a midsagittal plane of the body, as well as on a second (e.g., back) side of the frontal plane of the body. Meanwhile, the fourth pair of electrodes may be disposed on (or atop) one or more right back muscles of the body, and the fourth pair of electrodes may, therefore, be positioned on the second (e.g., right) side of the midsagittal plane of the body, as well as on the second (e.g., back) side of the frontal plane of the body. Other configurations and arrangements may be used.

Any of the electrodes described herein may be wettable electrodes that include an absorbent substrate (forming a fluid/wetting reservoir) in electrical communication with the electrode and configured to contact the user's skin (either directly or through the under suit). These wettable electrodes are configured to hold a conductive fluid (e.g., water, including saline) that may help make a reliable electrical contact with the user's skin, and maintain the electrical properties, even as the user sweats during physical exercise wearing the EMS suit. This may be particularly helpful, as these wettable electrodes may be configured (by size and position) to allow continuous electrical contact with the skin without having the electrical properties significantly change doe to sweating. The electrode assembly may also include one or more ports or opening configured to mate with the fluid source 125 (e.g., such as the spray bottle shown as an example in FIG. 1F). to allow delivery of the conductive fluid (e.g., saline) to the fluid reservoir. For example, each electrode assembly may include a port on an outward-facing side to which the fluid source may be engaged to apply (e.g., by spraying) fluid. The fluid port may also be configured to prevent leakage of fluid (e.g., saline) out of the port and/or out of the electrode assembly. The electrode assembly may include the fluid reservoir, which may be a porous material (e.g., sponge and/or wettable hydrogel, etc.).

The apparatus shown in FIGS. 1A-1F does not show the associated application or other components of the apparatus that may be used to control the applied power to drive EMS of target muscle(s). The controller 113 may include a user interface (e.g., touchscreen) for direct communication with the user and/or it may be configured to wirelessly communicate with one or more external processors, such as a smartphone, tablet, computer, etc. In some examples the user may communicate via a smartphone or tablet (not shown). In some examples the user may communicate with a remote processor. Any of all of the controller/power supply, smartphone, and/or remote processor may include software, firmware and/or hardware for engaging with the user and/or for controlling operation of the apparatus, including for engaging in one or more safety protocols to prevent a user from exceeding a predetermined or calculated amount of EMS to individual body regions (muscled) and/or the entire body based on the user's condition and prior operation of one or more EMS apparatuses.

Figure 2A:
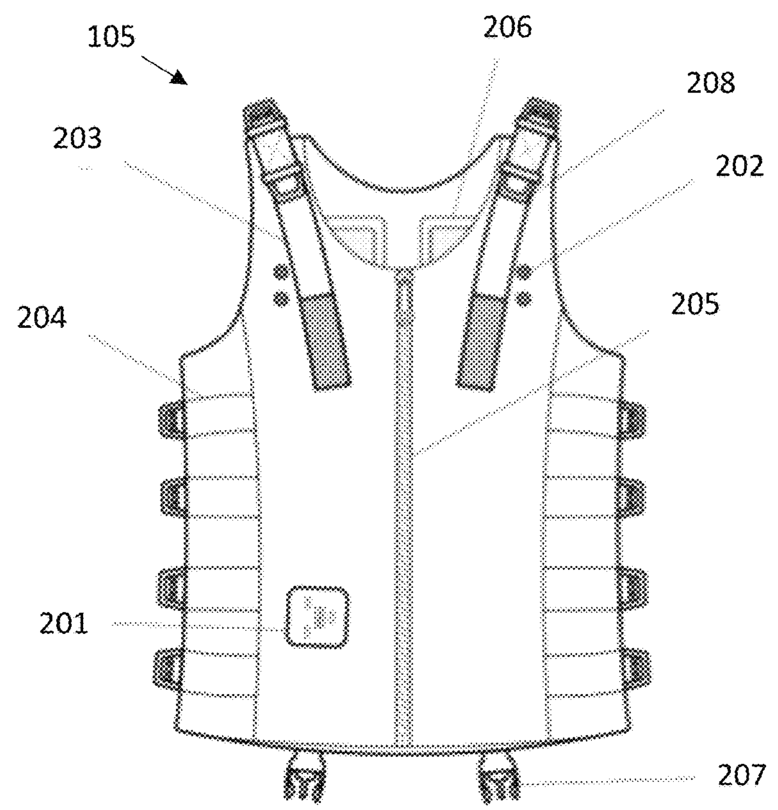

FIG. 2A shows an example of an upper torso portion 105. In this example, the upper torso portion includes a connector port 201 that may coupe with an integrated controller/power supply (not shown). The apparatus also includes a plurality of mechanical connectors (e.g., clasps, snaps, etc.) 202, and a plurality of adjustable straps (e.g., Velcro straps) 203, including side straps 204. The upper torso portion in this example also includes a zipper 205. A plurality of electrode pads 206 may also be integrated into the upper torso portion. The apparatus may also include connectors (e.g., buckles) 207 for coupling to a lower portion. Any of these connectors and/or straps may be adjustable and may include retainers 208.

Figure 2B:
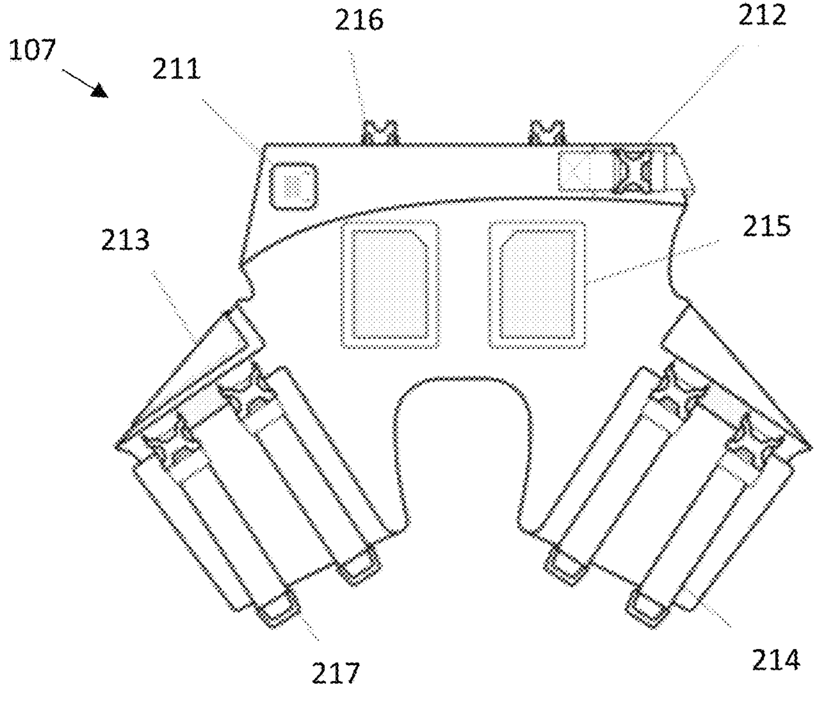

FIG. 2B shows an example of a lower portion 107. The lower portion may also include one or more mechanical and/or electrical connectors 216 for coupling to an upper portion (onto which a power supply/controller may be attached). Alternatively or additionally the lower portion may hold the controller/power supply (and may provide power and control operation of the upper portion(s)). For example, the lower portion may include a pocket and/or attachment site 213 for the controller/power supply and/or may include a connector port 211. The lower portion may include a hip belt 212 for securing the apparatus to waist (e.g., onto or over an under suit). In some examples the apparatus may include adjustable straps and/or buckles and/or other components to adjust the fit 216. The lower portion may also include one or more electrode assemblies (including electrical pads 215) for applying EMS to a muscle/muscle group on the lower body.

FIG. 2C illustrates an example of an arm electrode support 119 shown from the top 229 and bottom 228 (user-contacting side). The arm electrode support may include one or more attachments (e.g., straps 221) including loops 223 and/or Velcro attachment portions 224. The arm electrode support may also include one or more electrode assemblies 222.

FIGS. 3A and 3B illustrate examples of EMS suits as described herein, worn on a user. In FIG. 3A the EMS suit including all of the components described above, including an upper portion 305, a lower portion 307. The upper and lower portions are coupled together, and a power supply/controller 350 is shown coupled to the lower portion. The user is also wearing an upper 301 and lower 303 under suit.

The EMS suits shown may include electrodes on the legs, e.g., quadriceps, buttocks, lumbar region, back, trapezious, and one or more on the abdomen, pectorals, and arms. The positions may be adjustable, within a predetermined or arbitrary range. For example, on the legs, the lower portion may be configured to allow adjustment of the position(s) of the electrodes in one or two positions, such as over the medial thigh muscle or the medial and lateral muscles. Electrodes may be positioned between 5 cm and 10 cm apart. In another example, the apparatus may be configured to allow adjustment of the position of the muscles of the abdomen, including adjusting the pairs of electrodes to be further or closer apart. The central abdomen may be adjusted and/or a more laterally separated position may be used.

FIGS. 4A-4B illustrate another example of an EMS suit apparatus similar to that described above, in which an under suit may not be needed. In this example, the apparatuses include a wetsuit-like appearance, and may be formed, at least in part of an elastic material, such as a polymeric material (e.g., neoprene, etc.) that is breathable, and is configured to hold the electrodes (e.g., the electrode assemblies) in contact with the skin. For example, in FIGS. 4A and 4B, the EMS suit may include an upper 405 and a lower 407 portion, or may be a unitary suite (e.g., integrated upper and lower portion). The suite may be formed of an elastic fabric and includes a closing system 447 (e.g., zipper). The electrode assemblies may be integrated into the suit but may be configured to allow selection of one or more alternative positions, e.g., to allow the user to adjust the separation the anode and cathode electrodes. Thus, the electrodes may include an input (e.g., strap, selector, etc.) for allowing or locking internal movement of the electrode assembly position. As mentioned above, any of these electrode assemblies may be configured to allow fluid (e.g., saline) to be applied as part of the electrode assembly. In the example apparatus shown in FIGS. 4A and 4B the electrode may be coupled to the power supply/controller 450 by internal wires (not visible).

In some examples, the electrode assemblies or electrodes described herein may comprise one or more sensors as described herein. For example, FIG. 4B illustrates an exaggerated arrangement of sensors positioned throughout the EMS apparatus. Sensors 412 are shown and examples of sensor elements (e.g., a transmission element or a receiver element) 413 may be positioned at a location on the EMS apparatus to operably communicate with the biological tissues of the user. In some examples, the sensors 412 are integrated or otherwise associated with the electrodes or electrode assemblies. In some examples, the sensors 412 are located or locatable on an interior of the EMS suit such that they contact or are substantially proximal to the user's skin.

As mentioned above, any of these apparatuses may include electrode assemblies configured as wet or wettable electrodes. For example, these apparatuses may be configured so that fluid (e.g., water, saline, etc.) may be added to wet a skin-contacting surface of the electrode assembly. Electrical contact is essential to proper function and control of an EMS apparatus. The electrode assemblies may be wet prior to applying the apparatus and/or after applying the apparatus, and in particular the electrode assemblies including the fluid reservoir regions, e.g., a porous material (e.g., sponge and/or wettable hydrogel, etc.). FIG. 5 illustrates an example of the application of fluid (e.g., water) 567 via a spray bottle to wet electrodes 565 (and in particular, to wet the porous skin-contacting surface of the electrode) on the inside of the suit 563. In some examples the suit may include one or more ports into which a fluid (e.g., water, saline, etc.) may be added. The fluid may be a conductive fluid.

Any of the apparatuses described herein may include sensors, e.g., motion sensors, position sensors, etc. that may confirm the position and/or activity of the user. Sensors may be included with the one or more electrodes and/or may be included with the controller (or power supply and/or controller, including integrated power supply/controller). The sensor(s) such as an accelerometer, may be used to confirm that the user is performing a predetermined action/exercise (as described below) and may therefore coordinate the application of the EMS with the prescribed movement(s). The sensor(s) may also be used as a safety trigger, for example, stopping or pausing (or in some cases decreasing) the application of EMS based on the sensed motion and/or position.

In general, the suits described herein may be cleaned and maintained by the user. For example, the suits may be treated with an antibacterial solution and rinsed with water. An anti-odor product may be applied following each use, and/or after applying the antibacterial solution. The suit may be dried, e.g., by handling in a drying area. An air-drying system may be used to expedite drying. Heated or room-temperature air may be used to dry the suit. In general, the suit may be washed, e.g., by soaking in a soapy solution at low concentrations. The suit may be washed and/or rinsed in cold water to clean (including removing excess salts from the added fluid and/or sweat).

Figure 6:
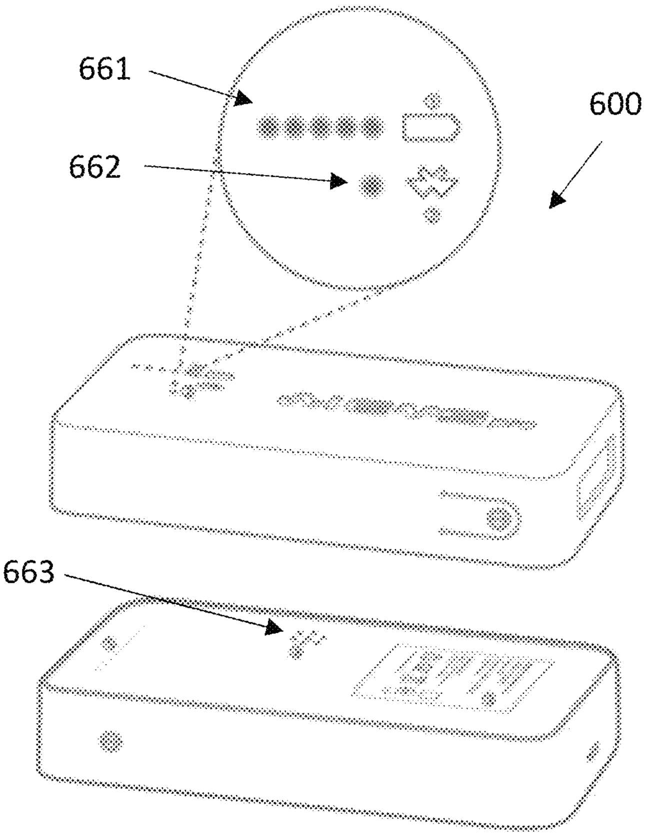
FIG. 6 shows one example of a power supply for an EMS or LT apparatus.
Figures 7A, 7B, 7C, 7D, 8A, 8B, 8C, 8D, 8E:
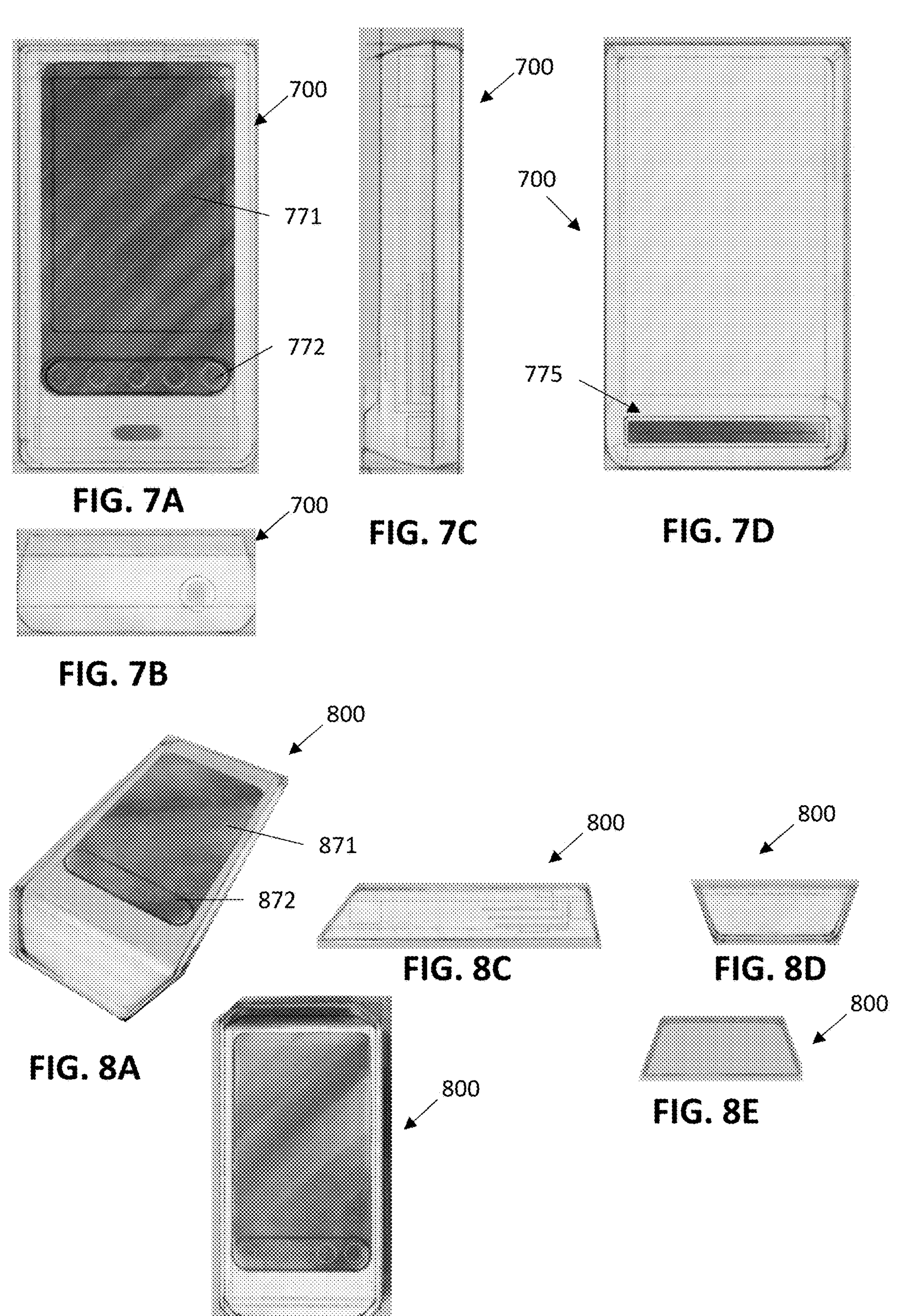
FIGS. 7A-7D illustrate an example of a combined power supply and controller for an EMS or LT apparatus as described herein.
FIGS. 8A-8E illustrate an example of a combined power supply and controller for an EMS or LT apparatus.

Also described herein are power sources and/or combined power sources (e.g., batteries) and controllers. FIG. 6 illustrates one example of a power source (e.g., battery) 600. This example may be used with an apparatus as shown herein and may include a simple user interface showing power level 661, wireless connectivity 662 (e.g., Bluetooth connection), etc. In some examples, described in greater detail below, additional user interface information (e.g., touchscreen) may be included. Any of theses apparatuses may include an audio output 663 (e.g., speaker) that may be used as an output. The power source/controller may be, e.g., 500 g or less (e.g., 450 g or less, 400 g or less, 350 g or less, 300 g or less, 250 g or less, etc.). The apparatus may be relatively small (e.g., 20×10×5 cm or less, 18×8×3 cm or less, 16.5×8×3 cm or less, etc.). The apparatus may also include an on/off button that may be manually or automatically controlled. Any of these power sources may be configured as batteries, such as lithium ion (Li-Ion) batteries. The power source may include a charging port (e.g., mini-USB port). In some examples the power source may also or additionally include a port for connecting to the EMS suit, and/or a cable connected to the EMS suit. As mentioned above, in some examples the power source (or power source/controller) may be configured to be secured within a pocket in the suite and may electrically couple to the suit while within the pocket.

Any of these power sources and power source/controllers may include one or more emergency shutoff controls, or an override shutoff control. The shutoff control may be configured to immediately stop the application of power to the electrodes. In some configuration the shutoff control may be configured to completely shut off the apparatus; in other examples, the shutoff control may continue sensing/monitoring and processor functions but may disable the application of power to any of the electrodes (e.g., for delivery of EMS) until a rest condition is satisfied. For example, in some examples an emergency shutoff control (or an override shutoff control) may be included on the outer surface of the battery or battery/controller. In some examples the suit may have an integrated shutoff control on the front outer surface of the suit that may be easily actuated by the user.

Any of these suits may include one or more sensors (e.g., physiological sensors), including heart rate sensors, pulse oxygenation sensors, respiratory sensors, etc. In some examples the apparatus may be configured to trigger a safety shutoff of EMS if the sensors detect user physiological signals that exceed a predetermined safety threshold. For example, if the heart rate exceeds, e.g., 180 bpm (e.g., 155 bpm, 160 bpm, 165 bp, 170 bpm, 175 bpm, 180 bpm, 190 bpm, 195 bpm, 200 bpm, 205 bpm, etc.), and/or if the blood pressure exceeds a predetermine range, etc.

FIGS. 7A-7D illustrate one example of a combined power source/controller 700. In this example the combined power source/controller including a touchscreen input 771, and may include one or more additional inputs 772, including an emergency shutoff control. The combined power source/controller may also include an attachment (input) 775 for coupling to a charging source and/or for coupling to an input/output (including a cable input/output) on the EMS suit. FIGS. 8A-8E show another example of a combined power source/controller 800 similar to that shown in FIGS. 7A-7D, also including a display screen (which may optionally be a touchscreen) 871 and one or more inputs 872, including, e.g., an emergency shutoff control. FIGS. 9A-9F shown another example of a combined power source/controller including a display 971 and inputs 972. This example also shows nan interface or adapter 976 for coupling to the EMS suit and/or a charger for charging the power supply integrated with the controller.

Figures 9A, 9B, 9C, 9D, 9E, 9F, 10:
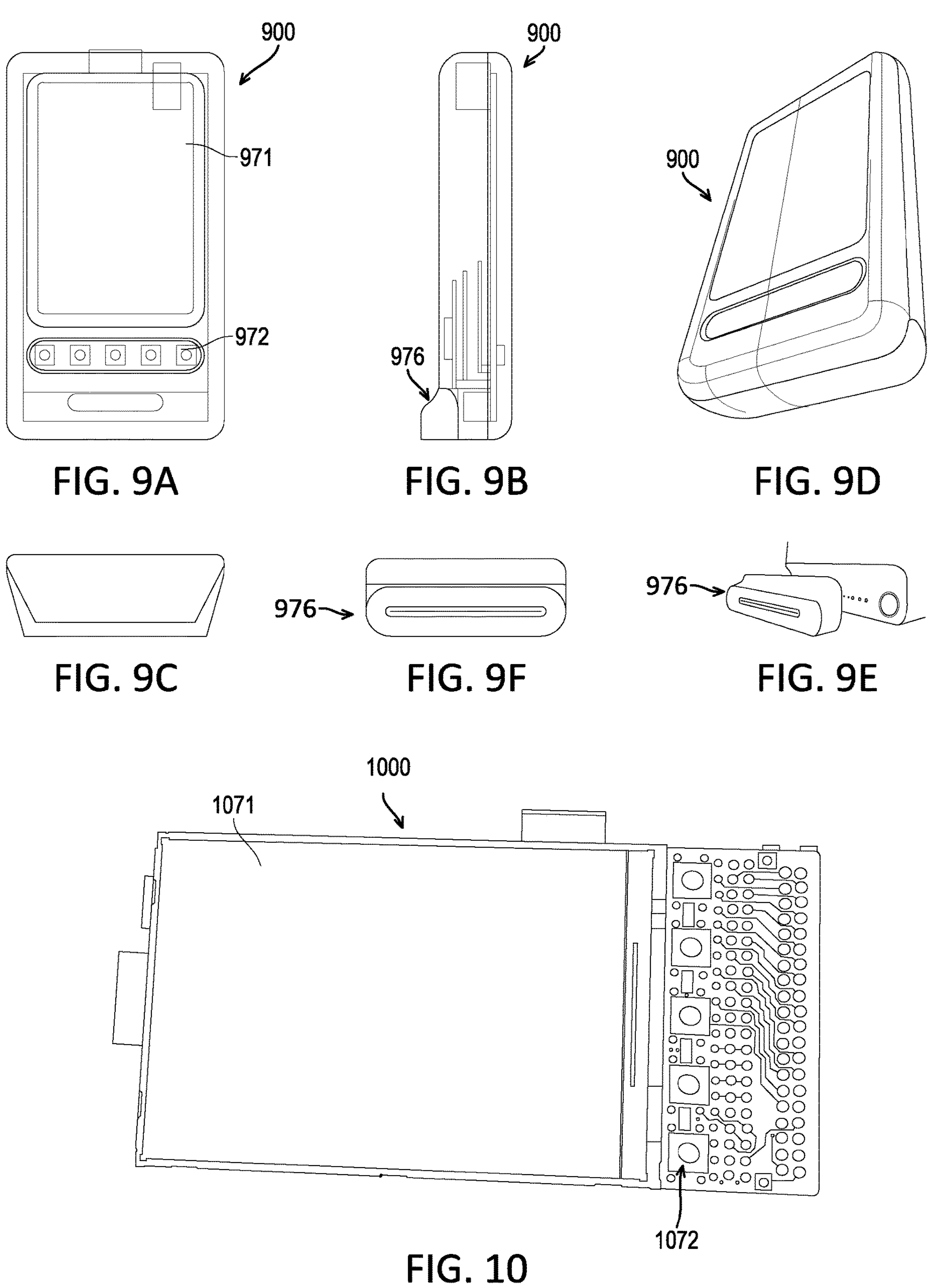
FIGS. 9A-9F illustrate an example of a combined power supply and controller for an EMS or LT apparatus.
FIG. 10 illustrates one example of a portion of a combined power supply/controller for an EMS or LT apparatus.

FIG. 10 shows an image of a prototype combined power source/controller 1000, with the outer housing removed, showing the display screen 1071 and inputs 1072 visible. The controller may include one or more processors, memory, timer(s), and control circuitry, including wireless circuitry and/or power control circuitry.

Figure 11:
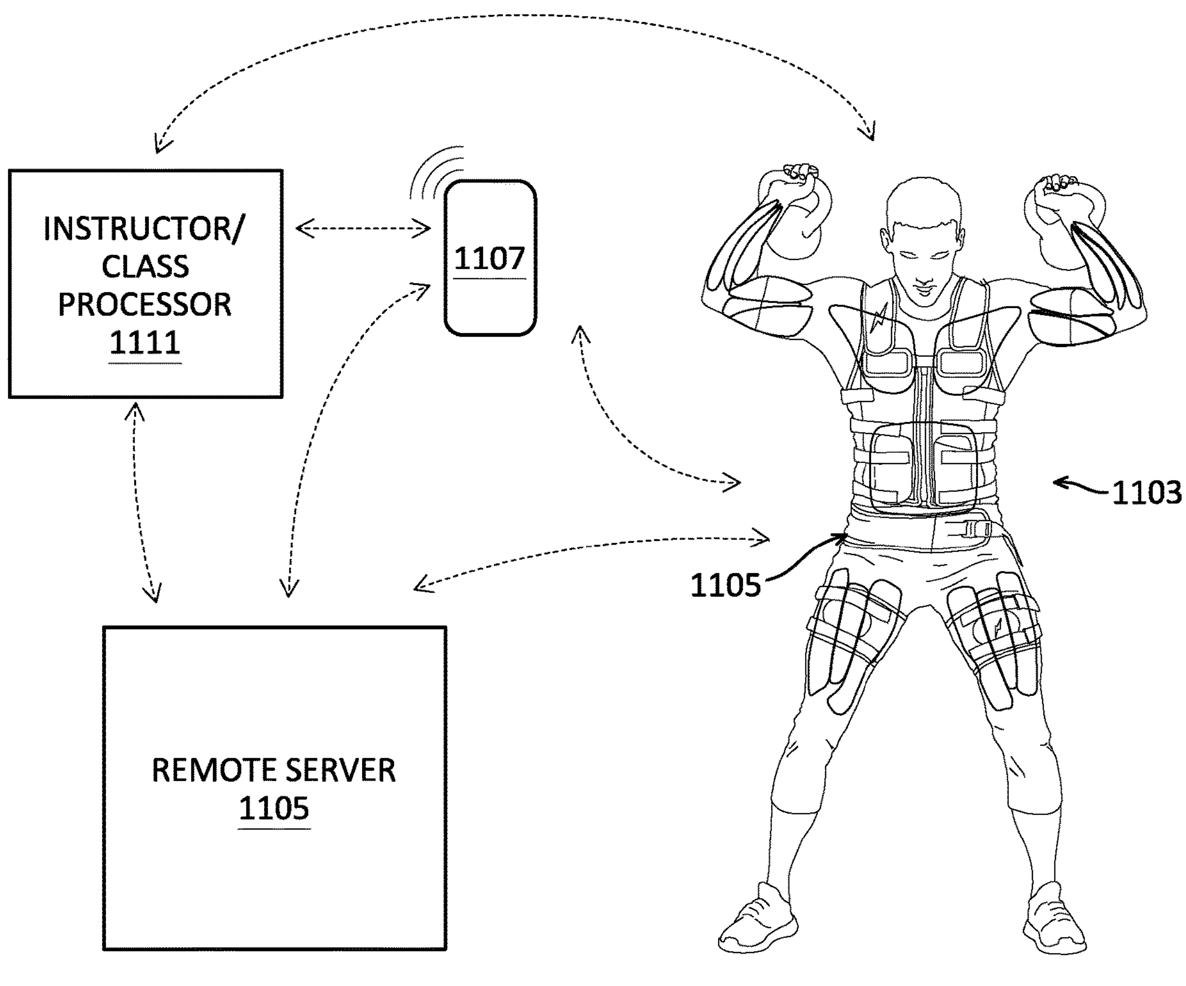
FIG. 11 schematically illustrates one example of an EMS or LT apparatus as described herein.

FIG. 11 illustrates one example of an EMS apparatus, including an EMS suit 1103, including a controller/power source that may operate with software on one or more of a user device (e.g., smartphone 1107), remote server 1105 and/or an instructor (or class) processor 1111. In FIG. 11, the EMS suit 1103 may be controlled by a worn controller 1105. The locally worn (EMS suit) controller may include the safety override control and may generally control the application of EMS to the electrodes/electrode assemblies in the suit, as described above. The locally worn controller (e.g., an integrated power supply/controller 1105) may communicate wirelessly, e.g., via Bluetooth (or other wireless technique) to any of the user device 1107, instructor/class processor 1111 and/or remote server. For example, the suit, which may be identified by a unique identifier associated with the user (e.g., name, number, address, etc.) may receive instructions for delivering a predetermined EMS protocol corresponding to a desired training regimen. The protocol may be delivered by the local controller but may be run in combination with the remote server, instructor class/server (for example, for group exercise) or from the user device (e.g., smartphone 1111).

In particular, the apparatus may be configured so that during a training episode, a selected or prescribed training regimen may be provided to the user, instructing the user to perform one or more actions. As mentioned above, a sensor, e.g., a motion sensor (e.g., accelerometer) may be included as part of a combined power source/controller and the controller may confirm that the user has begun, is in the midst of continuing to perform, or has completed, a prescribed movement before applying or continuing the application of EMS.

In general, the application of EMS may be targeted to a particular set of muscles or muscle groups corresponding to a particular activity. For example, the apparatus may be configured to apply a workout targeting a particular user goal, such as increasing endurance, mobility, and/or strength. These workouts may include a defined set of movement or actions (e.g., exercises, yoga/stretching poses or movements, etc.) and may be presented to the user concurrently with the application of EMS to one or more muscles (or muscle groups) related to the movements or actions.

For example, strength training routines may include resistance exercises (weights, bands, bodyweight, etc.), core strength, high-intensity interval training, etc., and may target specific muscles. The apparatus may automatically apply EMS in a coordinated manner with the presentation (and presumed performance) of the movements and/or may detect the user's movements and apply EMS when the user is performing the appropriate corresponding movement or shortly thereafter. In some examples the apparatus may therefore provide immediate feedback to the user that the movement is being performed within a desired level of activity, further reinforcing the effects of the EMS.

In any of these apparatuses, the intensity of the apparatus may be automatically adjusted to either adjust the applied EMS or to set the range of EMS intensities within which the user may select intensities (e.g., high, medium, low, off, or X % of 100%, where the range of 100% is set automatically by the system).

In particular, the apparatuses described herein may control and/or set the maximum EMS power/intensity that may be applied to a particular user based at least in part on one or more of: (1) an initial baseline (e.g., starting baseline) for the user; (2) the user-provided input(s); and (3) the historical (including within the last z hours or days) application of EMS by the same user. The apparatus may control the applied EMS power/intensity specific to each muscle or muscle group (e.g., the maximum intensity/power applied to the quadriceps may be different from the maximum power/intensity applied to the biceps, for example). Alternatively, the maximum power/intensity of the EMS applied may be the same across all muscles/muscle groups. The apparatuses described herein may adjust the EMS power/intensity by adjusting one or more of the pulse frequency applied (e.g., between 0/off and 120 Hz, e.g., between 0-100 Hz, between 50-120 Hz, between 60-120 Hz, between 70-120 Hz, between 80-100 Hz, between 70-100 Hz, etc.), the current applied (e.g., between about 0.2-120 milliamps (mA), between about 1-90 mA, between about 1-100 mA, between about 5-110 mA, between about 1-120 mA, etc. or any range within these), the pulse width (e.g., between about 100 microseconds (μs) to about 500 μs, between about 200 us to about 450 μs, between about 150 us to about 400 μs, or any ranges therebetween). In some examples the EMS power/intensity may be modulated by adjusting the ramp-up time (time to ramp up to a maximum applied current) and/or by adjusting the frequency within an application session (increasing or decreasing the frequency).

In some examples, the automatic adjustment of the intensity or the stimulation parameters or stimulation regime may be adjusted based on information acquired by the sensors (e.g., optical ultrasonic, electrical sensors). In some examples, the adjustment may be triggered based on a predetermined interval or duration of stimulation. In other examples, the user may be able to selectively engage the controller to initiate an update or adjustment procedure including the operation of the sensors to acquire data and provide updated sensor data for processing by the EMS apparatus that can be used for adjustment.

In general, the apparatuses described herein may be configured to apply power to just a subset of the electrodes (e.g., muscles or muscle groups) and may apply power to separate sets of electrodes corresponding to different muscles in an alternating manner, to avoid concurrent stimulation of multiple sets of electrodes.

The apparatuses described herein may be configured to safely apply EMS by controlling the applied energy (e.g., frequency and/or current and/or pulse width and/or ramp-up/ramp down time) based on a combination of on one or more of: (1) an initial baseline (e.g., starting baseline) for the user; (2) the user-provided input(s); and (3) the historical (including within the last z hours or days) application of EMS by the same user. In particular the apparatuses described herein may automatically set the maximum applied EMS power and/or intensity by estimating a maximum specific to a particular user base on the user's specific baseline and the user's recent (e.g., within the last z hours, where z is between about 8 hours or less, about 24 hours or less, about 36 hours or less, about 48 hours or less, about 60 hours or less, about 72 hours or less, etc.).

An initial baseline may be set based on a user's initial response to questions, such as the user's age, fitness level, general or specific health concerns, etc. In some examples the apparatus may perform an automated question and answer/testing session to set a baseline/initial user level. For example, the user may respond to questions regarding their ability to feel certain EMS inputs one or more (or all) of the electrodes. The user may also be asked to perform various actions (e.g., exercises) while wearing the apparatus and/or without wearing the apparatus and may provide feedback by self-reporting or via one or more sensors (e.g., heart rate, pulse oxygenation, accelerometer/position sensors, etc.).

The baseline data may be estimated, and an initial maximum level of EMS intensity/power may be determined. The initial baseline may be determined from population data of similarly-situated users (e.g., by age group, gender, health, weight, height, etc.). Initial baseline data may be set in part based on user-reported response to a variety of different EMS stimulation levels for each (or a subset of) muscles/muscle groups.

A dataset for each user may be maintained locally (e.g., on the user-specific EMS suit/controller) and/or may be kept in a remote database and accessed by the user-specific EMS. The user information (data) may include specific responses to the initial baseline data collection and/or the initial baseline values estimated by the system, including initial baseline values specific to each muscle or a subset of muscles). In some cases, initial baseline values for different muscles may be determined based on a patient-specific estimate for one or more muscles (e.g., quadriceps, biceps, pectorals, etc.).

User-specific baseline data may be adjusted periodically. User-specific data may be secured. For example, if user-specific date is recorded in a remote database it may be anonymous and indexed by a separately secured key corresponding to a particular user. In some cases, baseline information may be specific to an EMS system (e.g., EMS suit) and/or specific to a user. A user may be uniquely associated with a particular EMS suit).

The maximum EMS intensity/power that may be applied to the user may be adjusted with operation of the system. In general, the initial (e.g., baseline) EMS intensity/power may be set low, to avoid harming the user. With consistent use, the maximum intensity may be adjusted. For example, the apparatus may be configured to increase the maximum intensity with regular use and/or with user-requested increase.

As a safety, any of the apparatuses described herein may reduce and/or reset the maximum if EMS is not applied within a particular timeframe (e.g., if it has been more than x hours or days since the last EMS use). For example, for every x hours that the user has not operated the EMS apparatus the maximum intensity/power may be scaled towards the initial baseline (e.g., if no EMS has been performed by the user within 4 days, 5 days, 6 days, 7 days, 8 days, 9 days, 10 days, 11 days, 12 days, 13 days, 14 days, etc.).

Further, the system may lock out or prevent EMS from being applied more frequently than a predetermined time period. For example, the apparatus may be configured to prevent the user from applying EMS more than one session (or more than a maximum number of minutes or a maximum aggregate energy) every x hours or day (e.g., no more than once per 20 hours, per 24 hours, per 30 hours, per 36 hours, per 40 hours, per 44 hours, per 48 hours, per 52 hours, per 56 hours, per 60 hours, etc.).

Any of the apparatuses described herein may gradually increase the intensity of the EMS (e.g., the power of the EMS), e.g., by increasing one or more of the frequency, pulse width, amplitude, etc., over the course of a treatment session, up to a limit of the maximum intensity. For example, the apparatus may automatically increase the applied EMS power from an initial starting level up to 100% of the maximum EMS power/intensity available to the patient as calculated for a particular session (based on the baseline, historical, and/or user-selected input). In one example, a new user may have a maximum baseline power for their first session of 60 Hz, and a pulse width of about 200 us and an amplitude (which may depend on the electrode parameters) of, e.g., 100 mA. The applied intensity/power may be a function of one or more of these parameters. The apparatus may increase the applied EMS power/intensity from 50% of this value up to the maximum 100% (e.g., starting at 30 Hz and increasing to 60 Hz, etc.), which may be specific to a particular muscle or set of muscles.

Figure 12:
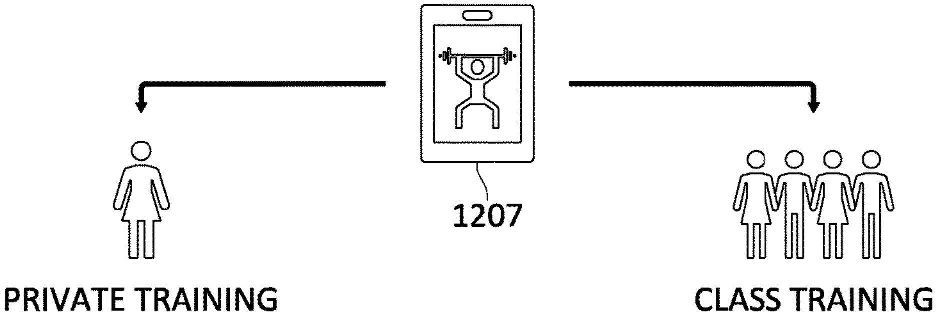
FIG. 12 schematically illustrates an example of a control system (e.g., application software) for an EMS or LT apparatus.

In general, these apparatuses may include software that may perform any of these methods. For example, the software may be an application software (app) that is configured to run on the user's device (e.g., smartphone) and/or on the power supply/controller. The software may be configured to control the EMS to a particular use or to coordinate the control of a group of users that may be exercising together, e.g., as part of a class. For example, FIG. 12 schematically illustrates a user software 1207 that may be used to assist the user in private training or in training a part of a class.

The application software 1207 may allow a user to select a particular training session and/or class and may coordinate the application of the training session and the application of the EMS. In some examples the application software may record the progress and may adjust the maximum possible EMS intensity/power for each session, as described above. The application software may therefore automatically adjust the settings (EMS settings) for each workout.

The sessions ("workouts') may start the EMS with settings based on the individual base settings (baseline) as mentioned above, and the apparatus may optimize the maximum possible EMS intensity and/or power for each setting, as well as the onset of this maximum during the course of a session. As described above, this may therefore be customized to each user and specific to their body and fitness level and configured to prevent harm or discomfort to the user. The apparatus may recalibrate the base settings.

Any of these apparatuses may include a user interface that may be displayed, for example, on the power supply/controller and/or on the user apparatus (e.g., smartphone, television/display, etc.). This user interface may include input/outputs for each of the EMS electrodes and/or corresponding muscle groups, including showing an intensity level (e.g., as frequency, amplitude, pulse width, and/or some combination or derived value of these, e.g., generically "intensity"). The user may be permitted to select a value for each or some of these which may be limited to the maximum level selected or set by the system. The user interface may also show the corresponding positions/movements/exercise and/or may display an instructor or model performing or guiding the user in performing them. In general, the apparatus (e.g., software, firmware, etc.) may coordinate the application of EMS via the EMS suit to the session being performed, including coordinating activating of the appropriate electrodes.

The techniques and systems described herein may also allow for one or more devices to conserve resources with respect to communications bandwidth resources, processing resources, memory resources, power resources, and/or other resources, as described herein. Additional technical effects can also be realized from an implementation of the technologies disclosed herein. Described herein are example processes, as well as systems and devices comprising one or more processors and one or more memories, as well as non-transitory computer-readable media storing computer-executable instructions that, when executed, by one or more processors perform various acts and/or processes disclosed herein.

Applications

The EMS apparatuses, systems and methods described herein may be adapted to supply therapeutically effective treatment to a patient in preparation of an invasive medical procedure. Increased muscle tone, mass, density, area, etc. can beneficially impact outcomes from an invasive medical procedure (e.g., surgery) and reduce complications.

The wearability of the EMS apparatus can increase patient compliance. For example, optimized preoperative conditions may include an increased muscle mass that may otherwise require prolonged exercise regimens that may not be possible for certain patients having a disease or condition impacting the patient's ability to effectively perform such exercise regimen. In some examples, a patient may engage the EMS apparatus (e.g., EMS suit) and receive electrical stimulation adapted to increase muscle mass, increase circulation, and otherwise modify the characteristics of one or more biological tissues in advance of a surgical procedure.

In some examples, the EMS apparatus and/or treatment protocol supplied thereby may be configured to increase muscle mass by less than 1%, 1%, more than 1%, more than 5%, 10%, 15%, 20%, or more. In some examples, the percent increase of muscle mass may be a target adjustment.

In some examples, the EMS apparatus may be configured to interpret a target modification of one or more biological tissues (e.g., increase in muscle mass). The target modification may be established or predetermined by a healthcare provider (e.g., physician, physical therapist, etc.). In some examples, the target modification may be based on the patient-specific biometric data acquired by the EMS apparatus. In some examples, the target modification may be based on a one or more databases (e.g., literature) in communication with the EMS apparatus and relating to reported or known outcomes of patients having the same or similar invasive procedure.

In some examples, the EMS apparatus as described herein is used as a therapeutic device to supply electrical stimulation adapted to modify one or more characteristics or composition of a biological tissue associated with an invasive medical procedure. Therapeutic applications may relate to any disease or condition including diseases or conditions that may be detectable with minimally invasive or non-invasive sensors associated with the EMS apparatus. Diseases or conditions may include any disease, condition, or natural decrease in muscle mass, muscle density, muscle function, muscle activity, etc. In some examples, one or more profiles may be stored, developed, established, acquired, or otherwise known to the EMS apparatus and can be used to compare or cross-reference the user-specific biometric data obtained by the EMS apparatus via the one or more sensors. The profile may be associated with a patient-specific range of biological tissue characteristics optimized for pre-operative conditioning to improve surgical outcomes and decrease complications.

The systems described herein may include one or more disease profiles cross-referenceable against the patient and invasive procedure. The profile may include known characteristics of a disease or condition such as symptoms, risk factors, genetic factors, biological factors, physiological factors, and/or any other relevant information associated with an outcome of a surgical procedure. The profile may provide a similarity score based on the comparison of the user-specific (e.g., patient specific) against a database of matched patient outcomes of those with similar patient attributes (e.g., age, weight, height, body mass index, pre-existing conditions or diseases, etc.) biometric data acquired by the EMS apparatus. For example, a similarity score may indicate a similarity between the observed or acquired user-specific biometric data and the known characteristics of a condition such as sarcopenia, or similar condition, known to be associated with negative procedural outcomes.

In some examples, an EMS apparatus as described herein can detect a disease or condition that may negatively impact an outcome or complication associated with an invasive procedure. Detection of a disease or condition may include the EMS suit sensing or analyzing user-specific factors relating to a disease of condition. One or more sensors within the suit may be adapted to receive biological and/or physiological data relating to the user and associated with a sign, symptom or other manifestation of a disease or condition. For example, detection may include the accelerometer sensors detecting a change in user-related acceleration and may signal a contemporaneous or impending incidence of biological activity (e.g., muscle activity) associated with a disease. In some examples, more than one type of sensor detect different user-specific biometric information that is interpreted and compiled by the processor for consideration as an incidence of detection of disease-related biological activity.

For any of the applications of the EMS apparatus described herein, a threshold may be established related to the user-specific biometric data detected by the sensors. A threshold may be a user-specific threshold based on a user engaging the EMS apparatus (e.g., the user wearing the apparatus) for a period of time. In establishing a threshold, the duration of time may begin with a first use as the sensors begin to acquire user-specific data. As data is accumulated by the EMS apparatus, patterns, rhythms, or other natural fluctuations in the user-specific biometric data may be incorporated into establishing a threshold specific to the user. For example, developing a threshold with the EMS apparatus may be a calibration of the EMS apparatus for a specific user.

In some examples, developing a threshold or standard values associated with the biometric data detected by the sensors may be predetermined. For example, known values include a range of values with a minimum and maximum that can be considered to be a healthy state. A healthy state value range may include an upper limit or lower limit associated with the particular biometric factor being evaluated. In some examples, predetermined thresholds may be adjusted or established by an individual (e.g., a healthcare provider) based on known acceptable or healthy-state values for a particular biometric factor.

In some examples, an EMS apparatus as described herein may be used to generate a report of surgical site (e.g., biological tissue) characteristics that can impact an outcome of a surgical procedure. Generating a surgical site report may include the EMS suit sensing or analyzing user-specific factors relating to a tissues proximal to or associated with a surgical site. One or more sensors within the suit may be adapted to receive biological and/or physiological data relating to the user and associated with a tissue characteristic (e.g., tone, composition, innervation, mass, density, etc.). In some examples, generating a surgical site report may include an EMS stimulation as a test or challenge of one or more biological tissues. The diagnostic EMS challenge may be supplied by one or more electrode assemblies, as described herein. In some examples, the diagnostic EMS challenge may be supplied according to a testing regime based on the user-specific information, predetermined user information, one or more profiles, one of more evaluation procedures based on an invasive procedure profile, etc. The one or more sensors may acquire or detect user-specific information and one or more electrode assemblies may supply an electrical pulse or stimulation to challenge or test associated biological tissue (e.g., muscle tissue) which can illicit a physiological response. The response may be detected by one or more sensors and the data may be sent to the processor for interpretation. The processor may interpret the data and compare detected user-specific information against profiles to generate a surgical site report (e.g., pre-operative report) of tissue condition in advance of a surgery.

In some examples, an EMS apparatus as described herein may treat a patient in preparation of an invasive procedure. For example, treatment may be adapted to optimize biological tissue for the reduction or prevention of complications of a surgery. Treatment of a patient may include the EMS suit sensing or analyzing user-specific factors relating to the condition of biological tissues associated with, impacting, or impacted by an invasive medical procedure.

Treating a patient as described herein, may include EMS supplied by one of more electrodes (e.g., electrode assemblies) based on user-specific biometric data. In some examples, the supplied EMS may be dynamically adjusted based on the user-specific biometric data. In some examples, the EMS may be dynamically adjusted based on a known or suspected condition of the user that may be associated with negative surgical outcomes. In some examples, the EMS may be adjustable by the user or by another individual (e.g., a healthcare provider) through engaging the interface of the system to adjust EMS maximum, minimum, or values therebetween.

In some examples, the user may be at an increased risk of complications due to an invasive medical procedure. The increased risk of complications may be associated with natural decrease in muscle tone (e.g., aging, sex, dietary impact, etc.). The risk of complications may be associated with a disease negatively impacting biological tissues associated with a surgical site (e.g., aging, sarcopenia, atrophy, lifestyle, cancer, neuromuscular conditions, hormone imbalance, etc.).

An example of a disease or condition that may be detected, prevented, treated and/or diagnosed may be Sarcopenia. Sarcopenia is a muscular disorder associated with a decrease in muscle mass. These methods and apparatuses described herein may be use in particular to treat sarcopenia instead of, or in addition to, other techniques for treating sarcopenia. For example, sarcopenia may be treated by the application of EMS either to one or more anatomical regions of the user.

In general, sarcopenia may be treated by applying EMS during one or more treatment sessions as described herein. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be atrophy. atrophy is a muscular disorder, may be treated with pharmaceuticals or conservatively. The methods and apparatuses described herein may be use in particular to treat or reverse atrophy instead of, or in addition to, other techniques for treating atrophy. For example, atrophy may be treated by the application of EMS either to one or more anatomical regions of the user.

In general, atrophy may be treated by applying EMS during one or more treatment sessions as described above. Treatment may be passive (e.g., without the user/patient) exercising, or active, including actively moving or exercising. One or more treatment may be applied, including one or more 5-40 minute sessions (e.g., 10-30 min. 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be age-related decrease in muscle mass. Age-related decrease in muscle mass can be based on natural senescent processes, accelerated by one or more genetic aberrations, or a combination thereof. In some examples, symptoms of aging (e.g., age-related decrease in muscle mass) may be treated with pharmaceuticals or conservatively. These methods and apparatuses described herein may be use in particular to treat age-related muscle mass decrease instead of, or in addition to, other techniques for treating age-related muscle mass decrease. For example, age-related muscle mass decrease may be treated by the application of EMS either to one or more anatomical regions of the user.

In general, age-related muscle mass decrease may be treated by applying EMS during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be any disease or condition associated with a negative impact on muscle mass, density, composition, circulation, innervation, area, etc. or a combination thereof. Neurological disorders, cancer, neuromuscular disorders, eating disorders, behavioral conditions, psychiatric disorders, auto-immune diseases, etc., may be associated with, or have as a symptom, a negative impact on biological tissues that can increase the incidence or risk of surgical complications. One or more treatment sessions (e.g., EMS stimulation treatments with the EMS apparatus) may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). The EMS treatment may be adapted to counteract the disease-associated impact on the biological tissues associated with a surgical site. By counteracting the disease-associated impact on the biological tissue, the EMS apparatus may sufficiently improve the biological tissues to decrease a risk of complications associated therewith. In some examples, the complications may include the time required to recover function, aesthetics, composition, activity, etc. or a combination thereof relating to the surgery.

The EMS apparatus (e.g., suit, system, treatment protocol, or combination thereof) may be adapted to supply therapeutic electrical stimulation to a patient not having a disease or condition. In some examples, the patient does not have a disease or condition and may engage the EMS apparatus in preparation of an invasive medical procedure. The EMS apparatus can supply electrical stimulation manually, or according to a treatment protocol (e.g., stimulation protocol) to improve tissue characteristics in anticipation or preparation for surgery. The treatment can decrease recovery time, decrease scarring, decrease complications, etc. or a combination thereof.

Any of the methods and apparatuses described herein may be used for one or more therapeutic indication, such as for physiotherapy by a patient (user) recovering from an injury, surgery, etc. For example, a patient may be subjected to an invasive medical procedure and engage and EMS apparatus described herein to supply therapeutic electrical stimulation. The stimulation supplied by the EMS apparatus can be configured to decrease recovery time, increase range of motion, increase muscle function, decrease scarring, increase circulation, etc. or a combination thereof.

In some examples, a user is at risk of a disease or condition based on the user's family history, age, sex, lifestyle, habits, comorbidity, genetic mutations, acquired molecular aberrations etc.

In some examples, the EMS apparatus, system and methods described herein may be configured to decrease recovery time and improve other outcomes related to a ligament replacement. For example, anterior cruciate ligament (ACL) reconstruction recovery to restore stability and function to the knee may takes nine months or more. A patient may engage an EMS apparatus described herein prior to, after or a combination thereof to reduce the recovery time after an ACL reconstruction or replacement surgery. For example, the recovery time may be reduced from nine months on average to less than nine months on average.

In some examples, the EMS apparatus, system, and methods described herein may be configured to decrease recovery time and improve other outcomes related to an organ transplant, removal, or repair. For example, a lobectomy (e.g., related to lung cancer or another disease) may require several months to a year or more of recovery time. A patient may engage an EMS apparatus described herein prior to, after or a combination thereof to reduce the recovery time after a lobectomy. For example, the recovery time may be reduced from a year on average to less than a year on average.

In some examples, the EMS apparatus, system and methods described herein may be configured to decrease recovery time and improve other outcomes related to a splenectomy. A splenectomy is the total or partial surgical removal of the spleen. Laparoscopy procedure uses smaller surgical cuts. Even laparoscopic splenectomy may be less invasive (e.g., minimally invasive) still requiring at least four to six weeks to recover from the procedure. For example, splenectomy recovery may take two months or more. A patient may engage an EMS apparatus described herein prior to, after or a combination thereof to reduce the recovery time after a splenectomy. For example, the recovery time may be reduced from two months on average to less than two months on average.

In some examples, the EMS apparatus, system and methods described herein may be configured to decrease recovery time and improve other outcomes related to a joint replacement. For example, hip replacement or reconstruction recovery to restore stability and function may takes several months to a year or more. A patient may engage an EMS apparatus described herein prior to, after or a combination thereof to reduce the recovery time after a joint replacement surgery. For example, the recovery time may be reduced from several months or more than a year to less than several months.

In some examples, a method of decreasing recovery time after an invasive medical procedure may include a patient engaging an EMS apparatus described herein. The EMS apparatus can supply electrical stimulation to the patient via one or more electrodes. The electrodes may supply the electrical stimulation according to one or more stimulation protocols. The electrical stimulation can modify one or more characteristics of muscle tissue, vascular tissue, circulation, dermal characteristics, nerve characteristics, associated functions, etc. or a combination thereof. The electrical stimulation can beneficially impact one or more tissues and thereby decrease the recovery time including decreasing the time to recover range of motion or function of the muscle and associated biological systems.

Figure 13:
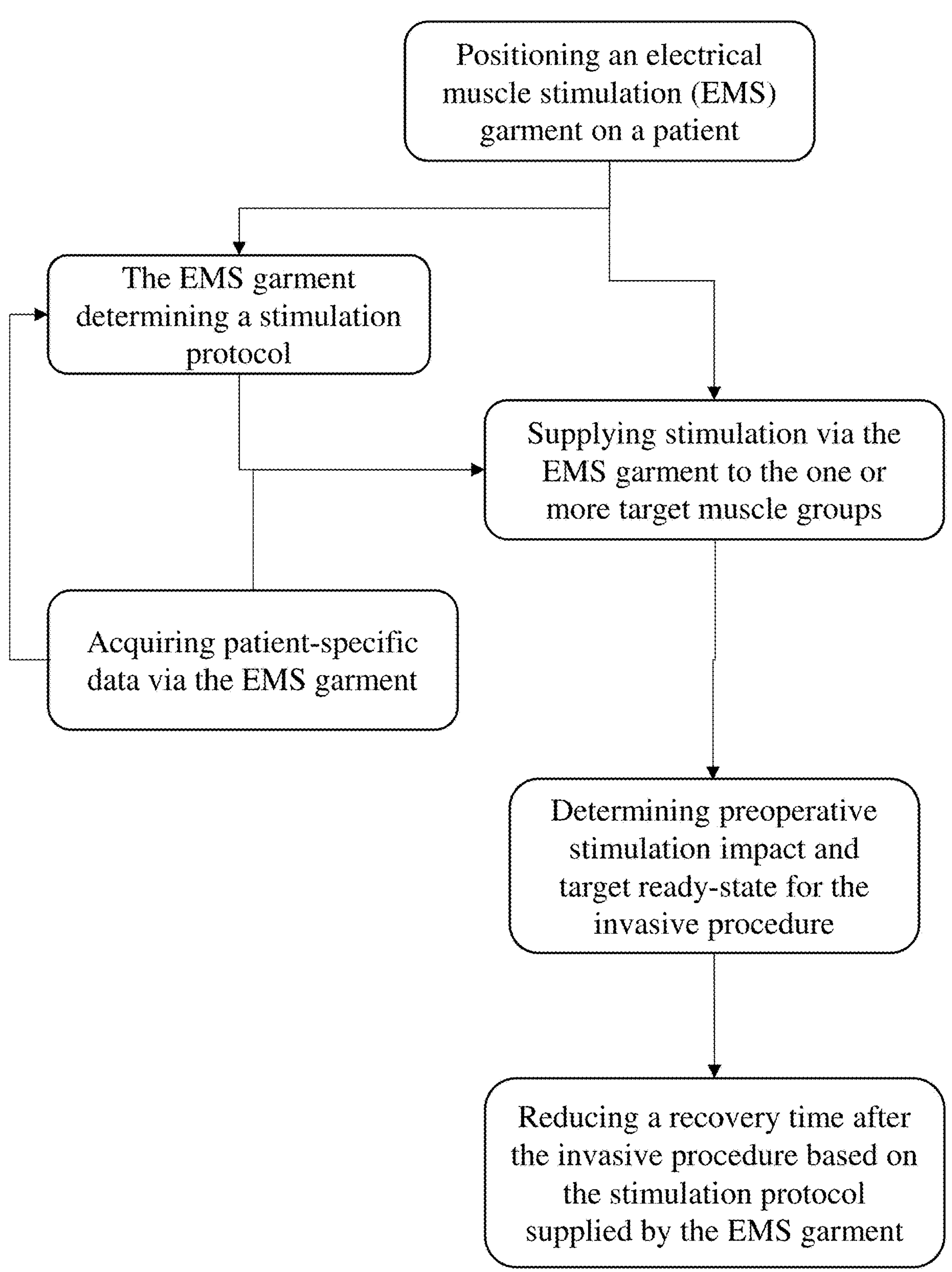
FIG. 13 schematically illustrates an example of a method for using an EMS or LT apparatus, as described herein.

In FIG. 13, a diagram of a method for reducing recovery time is illustrated. The patient may engage the EMS garment and the garment may determine a stimulation protocol based on the data obtained from one or more sensors. A control may be employed to calculate and direct the operation of stimulation via the one or more electrodes according to the stimulation protocol. Then, the electrical stimulation is supplied by the EMS garment (e.g., apparatus). For example, the electrical stimulation may be supplied according to the stimulation protocol, manually, or a combination thereof. The EMS garment may acquire additional patient-specific information and adjust the stimulation protocol. The acquired data may not result in any adjustment to the previous (e.g., initial or existing stimulation protocol). The EMS apparatus may also be configured to determine a viability of procedural success. In some examples, the EMS garment (e.g., apparatus) may be configured to acquire data used to determine the success of the electrical stimulation to improve or modify the muscle tone or other biological tissue characteristics in preparation of the invasive procedure. In some examples, determining the stimulation impact may be used to generate a projection or date of completion for the pre-operative electrical therapy (e.g., electrical stimulation). Finally, the recovery time is reduced based on the impact of the electrical stimulation prior to the invasive procedure. In some examples, the EMS suit may be continued in use after the procedure.

The method may also include the EMS suit acquiring patient specific data (e.g., muscle mass, tone, density, etc.) to determine the potential for beneficially impacting one or more muscles associated with a surgical site. In some examples, the EMS apparatus may acquire patient specific data via the one or more sensors. The patient specific data may be interpreted by the system and incorporated in, or modify one or more algorithms defining the stimulation protocol. The modification of the stimulation protocol can optimize the stimulation characteristics to improve biological tissues in advance of an invasive procedure.

The patient may incorporate one or more medications or lifestyle changes to support or amplify the impact of the electrical stimulation supplied by the EMS apparatus. Methods described herein may include an adaptation of the simulation protocol based on monitoring or subsequently acquired patient-specific data (e.g., data acquired after an initial use or input). The stimulation protocol may be adjusted according to changes observed, acquired, or sensed by the EMS apparatus. In some examples, the stimulation protocol may be manually adjusted by a user (e.g., the patient and/or healthcare provider) based on a desired outcome or modification process based on the electrical stimulation protocol.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

In general, any of the methods and apparatuses described herein may be used for physiotherapy. For example, EMS may be used as a rehabilitation tool for a range of neuromuscular conditions in adults and children, including (but not limited to) stroke, spinal cord injury, ABI and cerebral palsy. EMS may be used alone or with other conventional physiotherapy adjuncts. For example EMS may be used to reverse muscle atrophy and improved muscle strength; for support of function (i.e. stepping of the foot during gait), for improved local circulation and reduction in skin breakdown; for increasing and/or maintenance joint range of motion, for reduction of spasticity or muscle spasms; for an increase in cardiovascular function (e.g., via simultaneous activity of large muscle groups); for habilitation (e.g., learning new activity via movement normally unobtainable); for maintenance of bone density; and/or for restorative therapy (e.g., CNS cell birth & CNS myelination).

Figure 14:
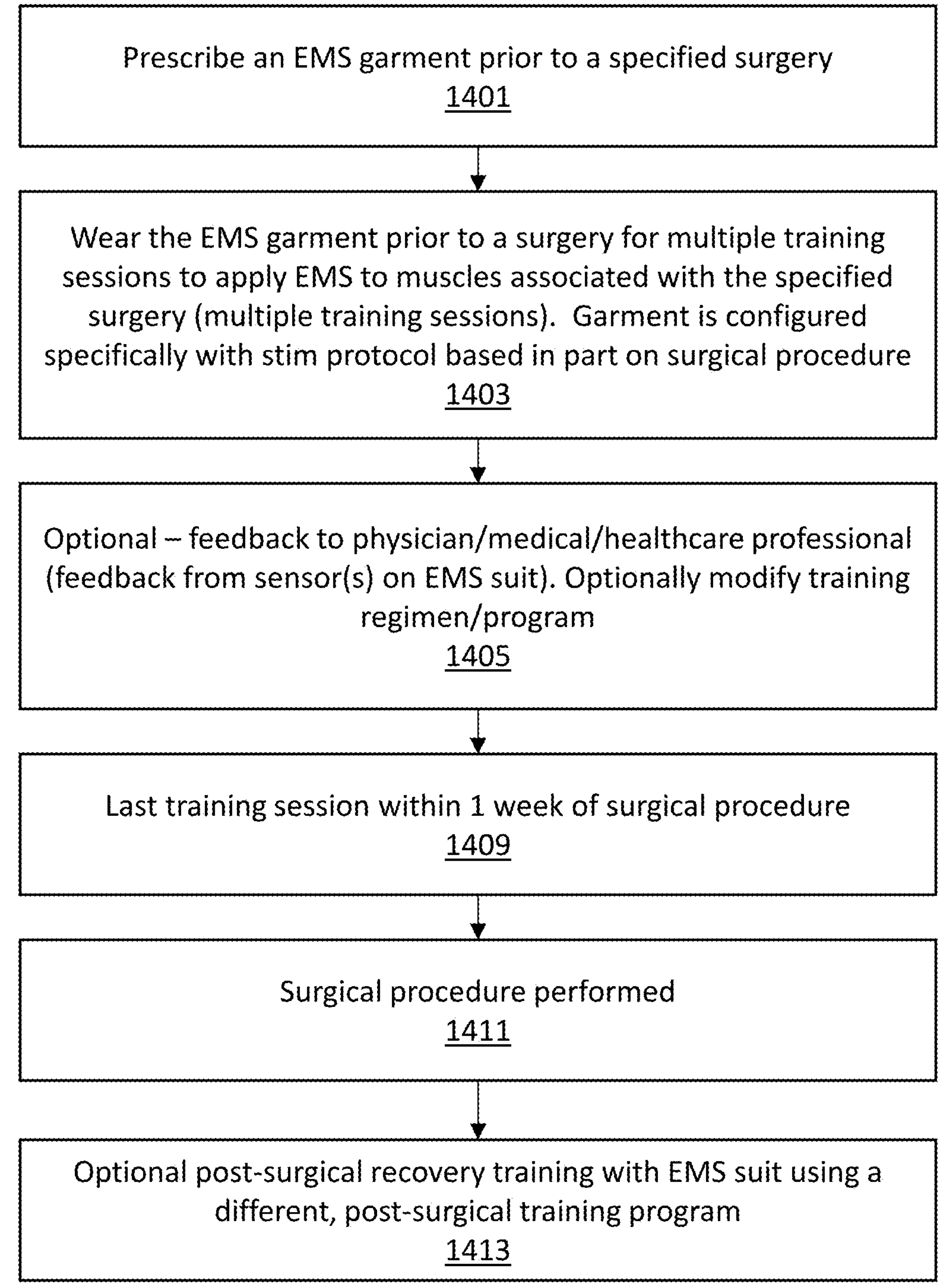
FIG. 14 schematically illustrates an example of a method of using an EMS or LT apparatus for pre-(and optionally post-) surgical treatment to significantly reduce recover times.

FIG. 14 illustrates one example of a method for pre-surgical treatment using an EMS apparatus as described herein which may significantly reduce recovery time and complications as described herein. In FIG. 14, the method includes receiving (e.g., by a patient) a prescription for an EMS pre-surgical treatment 1401. The prescription may be made by a medical practitioner (e.g., doctor, therapist, etc.). A prescription may be an optional step. The EMS apparatus may be preconfigured based on the type of surgical procedure, including the placement of the electrodes and/or the programming for operating the apparatus.

The patient may wear the EMS apparatus (garment) during a series of training sessions prior to the surgical procedure 1403. For example, daily, every-other-day, every 3 days, etc. training sessions may be performed. The stimulation parameters may be configured specifically to increase tone and response of muscle that are associated with the surgical procedure, including those that may be treated and/or those muscles that couple with or support the region being treated. In addition to the applied energy, the apparatus may guide the user through one or more actions (movements, exercises, etc.) concurrent with the application of energy.

Optionally, the method may include feedback from the medical professional (doctor, technician, nurse, physician assistant, therapist, etc.) 1405. The patient may be monitored and/or the treatment protocol may be modified.

Typically the patient may continue the pre-operative use until at least 1 week (e.g., 5 days, 4 days, 3 days, 2 days, 1 day) of the surgical procedure 1409. The surgical procedure may then be performed 1411.

Optionally, the patient may receive post-surgical use of the EMS apparatus specific to the performed surgery 1413. The training regimen (program) of the EMS apparatus may be different than the pre-surgical training regimen (program), and may also optionally be monitored and/or modified by the medical professional.

Described herein are LT apparatuses (e.g., devices and systems, including suits, controls, light sources, operational protocols, etc.) including a therapeutic system for the detection, prevention, diagnosis and/or treatment of a disease or condition. The LT apparatuses may include a plurality of structural elements adapted to acquire user-specific data related to a disease or condition. One or more light sources configured to supply therapeutically effective light (e.g., radiation energy) can be positioned and/or locatable on and/or in an LT apparatus.

A LT apparatus can have one or more light sources configured to emit energy to a user. The light energy can be therapeutically effective to diagnose, prevent, treat, etc. a disease or condition. In some examples, the light therapy can be therapeutically effective to beneficially affect or impact a change to one or more biological processes and/or biological tissues. Light therapy can be effective in the treatment of a disease or condition, as well as beneficially impact patients in a healthy state (e.g., without a disease or condition).

In some examples, light therapy may be photobiomodulation therapy (PBM), laser therapy (e.g., low-level laser therapy), blue light therapy, red light therapy, phototherapy, ultraviolet (UV) light therapy, etc. In some examples, light therapy may be a therapeutic application of energy from one or more light sources via an LT apparatus (e.g., LT system) described herein. Any example of light therapy can involve one or more light sources. For example, a light source may be a light emitting diode (LED) and/or laser or other light source configurable of generating, emitting, supplying, applying etc. radiation energy (e.g., light energy). In some examples, the one or more light sources are configured to emit energy (e.g., radiation energy) that can have one or more energized particles.

The light energy (e.g., light therapy) can be configured to improve biological tissue and/or biological processes. For example, treatment with an LT apparatus can improve mitochondrial function and reduce inflammation. In some examples, a LT apparatus can be configured to supply light therapy treatment via one or more light sources. The treatment can modulate cell signaling and may be beneficial in the prevention, treatment, abatement, etc. of a disease or condition. In some examples, the treatment can be effective to modulation one or more biological tissues or processes for a desirable cosmetic (e.g., not related to a disease) impact.

One or more sensors can be operably coupled to an LT apparatus and configured to obtain user-specific data before, during and/or after use that may relate to a sign or symptom of a disease, condition, or risk factor for the same. Each of the sensors may be configured to receive or acquire data that may be interpreted by the therapeutic system and used in the detection, prevention, diagnosis and/or treatment of a disease or condition. For example, the sensors may detect or acquire biometric data associated with the user. In some examples, each of the sensors (e.g., one or more sensors) may be configured to receive or acquire data that may be interpreted by the LT system and used in a subjective or desired (e.g., cosmetic) adjustment by the LT system. In some examples, a desirable cosmetic adjustment regime by an LT system can be detection, prevention, diagnosis and/or treatment, as described herein.

In some examples, the LT apparatuses may include one or more sensors configured to acquire and/or generate data and information within the apparatus to detect, diagnose, prevent, and/or treat a disease of condition based on user-specific characteristics. The sensors may operate using various techniques to acquire biological and physiological information (e.g., composition and/or characteristics of one or more biological tissues) from a user. For example, the sensors may be configured to detect inflammation or other symptom of a disease or condition that may be interpreted by the LT apparatus (e.g., via a therapeutic system) and used in determining, establishing, and/or executing therapeutic protocols based on the detected inflammation. The LT treatment protocols may be adapted to the symptom or detected information relating to a disease or condition.

In some examples, an LT apparatus as described herein may include one or more sensors to acquire user-specific biometric data related to the composition and/or concentration of cells in one or more biological tissues. For example, one or more sensors may include an optical sensor. The LT apparatus (e.g., LT suit) may include one or more optical sensors located or locatable within, on and/or associated with the LT suit to sufficiently operate and detect user-specific data. An optical sensor may be configured to sense changes in composition and/or biological activity within one or more biological tissues of the user at an area or region of the user's anatomy and/or the user's entire body. The detected changes may include a ratio of change or changes over time (e.g., duration). The duration may be relative to an initial or baseline biometric data acquisition. In some examples, optical sensors may acquire initial biometric data upon initiation of a sensing period and/or at the beginning of a treatment session.

In some examples, one or more optical sensors described herein may be configured to acquire user-specific biometric data based on analysis of changes in wavelength, intensity, propagation, spectral distribution, polarity of sensor-emitted light, etc. Changes in the sensor-emitted light can be a result of contact or other interaction of the sensor-emitted light with the user. In some examples, one or more optical sensors described herein can also or alternatively be configured to acquire user-specific biometric data based on analysis of user-associated absorption, scattering, etc. of sensor-emitted light.

In some examples, optical sensors can be surface plasmon resonance based (SPR), localized surface plasmon based (LSP), optical waveguide based, optical resonator based, photonic crystal based (PC), optical fiber based, etc. For example, one or more sensors can be SPR sensors configured to monitor and acquire biometric data associated with molecular interaction within one or more biological tissues of the user. An SPR sensors can be configured to sense (e.g., acquire) systemic, intracellular and/or extracellular molecular attributes for analysis of antibodies, proteins, enzymes, drugs, small molecules, peptides, nucleic acids, xenobiotics, etc.

In some examples, and optical sensor may operate based on the sensor-emitted light modified by one or more body tissues (e.g., myofascial tissue). Changes in sensor-emitted light may relate to changes or modifications in one or more attributes of the light emitted by the optical sensors. The emitted light is received by the optical sensors after being transmitted. Changes in the received sensor-emitted light may relate to or be appreciated as an impact of the sensor-emitted light contacting a user's anatomy (e.g., dermis). The changes in the emitted light may relate to one or more optical properties of biological tissues. Optical properties may relate to determinable characteristics of the tissue contacted by the emitted light.

In some examples, the optical sensors described herein can be configured to acquire biometric data such as scattering of sensor-emitted light after contacting one or more biological tissues (e.g., dermis). Scattered light analysis by the LT apparatus described herein may relate to the impact of a biological tissue on sensor-emitted light causing light particles to scatter upon contact with various tissues structures (e.g., cells, fibers, extracellular environments, etc.). For example, the sensor-emitted light may have initial light attributes (e.g., wavelength, frequency, intensity, etc.). As the sensor-emitted light contacts or engages biological tissue (e.g., blood, dermis, muscle, etc.), particles from the sensor-emitted light can be scattered by the tissue and the optical sensors may acquire or sense the scattered light particles. Attributes of the acquired scattered light (e.g., vectors, reflection angles, velocity, quantity, concentration, etc.) may provide data input for quantification of one or more characteristics of the biological tissue (e.g., sign or symptom of a disease).

In some examples, an LT suit (e.g., an LT apparatus) may include more than one optical sensor having a transmission element and each transition element may be configured to emit light having sensor-specific attributes unique to the associated transmission element. The sensor-specific light attributes may be interpreted by one or more receiver elements of the optical sensors and to distinguish the location of the associated transmission element from which the light was emitted. In some examples, the optical sensors include a transmission element and a receiver element. The transmission element and receiver element may be incorporated into a single sensor unit. The transmission element may be capable of emitting light into or through one or more tissues of the user's body. The receiver element can receive light after the light has contacted or otherwise been modified by the one or more biological tissues (e.g., dermis, muscle blood, lymph, etc.).

One or more sensors (e.g., optical sensors) can be configured to sense (e.g., acquire) cell counts. For example, one or more sensors can be configured to distinguish different cells comprising an anatomic region of the user. The user-specific data acquired relating to user-specific cell counts can be interpreted by an LT system (e.g., LT apparatus) to develop, supply, adjust, evaluate, etc. treatment with the LT system. In some examples, a sensor can be configured to quantify different cell types in the user's biological tissue. For example, a sensor can be configured to sense biometric data of cells and composition passing through the patient's vasculature and the LT system can determine a quantity of cosinophils, hemoglobin, etc. In some examples, sensors can be configured to identify and/or distinguish different cell types based on the sensed characteristics and attributes (e.g., morphology) of the cell.

In some examples, an LT apparatus as described herein may include one or more sensors to acquire user-specific biometric data related to the visible characteristics of one or more biological tissues. For example, one or more sensors may include an imaging sensor. The LT apparatus (e.g., LT suit) may include one or more imaging sensors located or locatable within, on and/or associated with the LT suit to sufficiently operate and detect user-specific data. An imaging sensor may be configured to acquire observable (e.g., visible) user-specific biometric data. For example, user-specific images may be acquired by the imaging sensor of one or more anatomic regions of the user.

In some examples, imaging sensors may acquire more than one image when the LT apparatus is in use. Images may be captured or acquired over a duration of use and/or during subsequent uses of the LT apparatus. For example, an imaging sensor can be configured to acquire user-specific images showing a skin condition (e.g., psoriasis) that may be interpreted by the LT system (e.g., LT apparatus) to direct, implement, develop, supply, etc. application of light therapy in response to the acquired user-specific images.

An imaging sensor may be a camera system configured to acquire images and/or other observable user-specific biometric data. For example, the camera system may have one or more cameras positioned or locatable on an LT apparatus, as described herein. The camera system can be configured to acquire an image of an exterior surface of the user. In some examples, the camera system can have one or more thermal imaging cameras (e.g., forward-looking infrared) configured to acquire images having thermal attributes associated with the user. Images acquired by an imaging sensor (e.g., camera system) can be interpreted by an LT apparatus (e.g., LT system). For example, acquired images may be processed by a processor in operably communication with the LT system. One or more processing algorithms may be applied to the acquired image (e.g., images acquired by a camera system) and one or more elements of the image may be quantified for interpretation by the LT system in developing, supplying, adjusting, evaluating, etc. therapy supplied to the user by the LT system.

One or more of the sensors may include a thermal sensor (e.g., thermography sensor) configured to detect biometric data related to the internal and/or external temperature of a user. Body temperature may be a factor of one or more disease states or use in detecting, predicting, treating, preventing or diagnosing a disease of condition. The thermal sensors (e.g., temperature sensors) may be located or locatable on the LT apparatus to acquire or detect the temperature of the user via contact, infrared sensing, etc. The data may then be sent to the processing unit for interpretation and analysis according to any of the processes described herein. In some examples, the forward-looking infrared (FLIR) can be a thermal sensor configured to acquire user-specific thermal biometric data interpretable by an LT system (e.g., LT apparatus) to develop, supply, adjust, evaluate, etc. treatment applied by the LT system.

One or more of the sensors may be adapted to detect user-specific biometric data associated with respiration. For example, respiration volume, cadence, pulse oxygen levels, etc. may be detected by the one or more respiration sensors. In some examples, the respiration sensors may include sensors associated with the LT suit (e.g., LT apparatus) that detect a change in volume as the user inhales. For example, resistance sensors positioned throughout the suit may detect a strain on the LT suit as the user inhales. The quantity of strain detected may be interpreted in one or more algorithms adapted to quantify the volume and rate of respiration. The respiration sensors may also include an optical element configured to detect pulse oxygen through optically sensing a flow of blood through one or more blood vessels associated with the sensor.

One or more of the sensors may include an electromyography sensor configured to detect electrical events associated with muscle function. Electromyography sensors may detect or acquire user-specific data associated with the function of a muscle and may be configured to predict voluntary, involuntary or a combination of involuntary and voluntary muscle function.

Detection of user-generated electrical signaling may provide data related to the incidence or prediction of an impending disease-associated biological activity. For example, the electromyography sensors may detect impulses from the nervous system to one or more biological tissues related to a disease-associated biological activity simultaneously, or prior to the incidence. The data may be interpreted by the processing unit and may be a factor in detecting, diagnosing, preventing, and/or treating a disease. For example, treatment incorporating electromyography sensor data may provide support for treatment parameters and supplying of light energy (e.g., radiation energy) by the one or more light sources.

In general, an LT apparatus may include an LT suit having one or more sensors coupled or couplable thereto. Sensors may be associated with the LT suit in a configuration allowing for associated operation of the sensor to acquire data and information. The sensors may be operably connected to the LT suit and/or associated with one or more elements associated with the LT suit (e.g., electrical circuitry, light sources, controller, processor, power supply, etc.). Each sensor may operate independently or in combination with one or more other sensors or LT suit elements to acquire and/or determine user-related attributes (e.g., muscle characteristics) and transmit the user-related attributes to the LT system associated with the system for treatment and/or treatment regime management.

The LT apparatus, as described herein, may include one or more bioelectrical sensors to evaluate bioelectric characteristics of biological tissue. For example, impedance of the electrical impulse or energy emitted into the biological tissues of the user may related to biological characteristics of the tissue (e.g., dermis). Some examples of bioelectrical sensors may include a transmission element and a receiver element. A bioelectrical sensor transmission element may emit an electrical pulse into, through, across or throughout body tissue of a user. The emitted electrical pulse may penetrate through one or more biological tissues and be modified the composition, orientation, location, type, arrangement, etc. of the biological tissue. Changes in the electrical pulse can be interpreted by an LT system (e.g., LT apparatus) to develop, supply, adjust, evaluate, etc. treatment applied by the LT system.

In some examples, the bioelectrical sensors may include a transmission element and a receiver element. The transmission element may be configured to transmit an electrical impulse into, through, and/or across one or more biological tissues. The receiver element may be configured to receive the transmitted electrical impulse after it has contacted or otherwise been modified by one or more biological tissues (e.g., muscle tissue). In some examples, the electrical impulse from the sensor may be modified from initial attributes at the time the impulse is transmitted or emitted from the sensor. The difference in the received impulse may be interpreted by an LT system (e.g., LT apparatus) to develop, supply, adjust, evaluate, etc. treatment applied by the LT system.

In some examples, the sensors are ultrasonic sensors having a transmission element and a receiver element. The ultrasonic sensors may be adapted to emit sound of an initial frequency and wavelength into, across, or through one or more biological tissues. The receiver element may be configured to receive the transmitted ultrasonic waves after they have contacted or otherwise been modified by one or more biological tissues (e.g., muscle tissue). In some examples, the ultrasonic waves from the sensor may be modified from initial attributes at the time the ultrasonic waves are transmitted or emitted from the sensor. The difference in the received ultrasonic waves may be interpreted by an LT system (e.g., LT apparatus) to develop, supply, adjust, evaluate, etc. a treatment applied by the LT system.

The LT apparatus, as described herein, may include one or more spectrometry sensors to evaluate one or more characteristics of biological tissue (e.g., microcirculation). Some examples of spectrometry sensors can be near-infrared spectroscopy sensor (NIRS), tissue reflectance spectrophotometry sensor (TRS), optical coherence tomography sensor (OCT) etc. user-specific biometric data acquired by the one or more spectrometry sensors can be interpreted by an LT system (e.g., LT apparatus) to develop, supply, adjust, evaluate, etc. treatment applied by the LT system.

In some examples, one or more sensors can sense physical movement of the user (e.g., inertia measurement unity and/or accelerometer sensors). In some examples, the sensors can be accelerometers and may be configured to detect a symptom of a disease or condition. Detection by the sensor may include acquiring data by the sensor that is interpreted by the LT apparatus (e.g., the therapeutic system). Based on the interpretation and acquired data, the LT apparatus may provide an alert or notification of the detected incident.

In some examples, any of the sensors can be configured to acquire data associated with and/or related to identification and/or evaluation of an infection by microorganisms (e.g., bacteria and/or viruses).

In some examples, the sensors coordinate with each other to combine or compile data acquired thereby. The sensors may communicate acquired (e.g., sensed) data and sensor characteristics such as sensor location and sensor parameters to aggregate, organize, test, validate, etc. data that can be interpreted by an LT system (e.g., LT apparatus) to develop, supply, adjust, evaluate, etc. a treatment applied by the LT system. For example, sensors on the chest of the LT suit, may communicate information of the pre-determined location, targetable anatomy, and biological tissue characteristics. In some examples, the energy (e.g., light, sound, electricity, etc.) may be emitted by a first sensors and received by a second sensor. The second sensor may be the same sensor or a different sensor. The second sensor may be the same type of sensor as the first sensor or may be a different type of sensor than the first sensor. For example, a first sensor may emit some type of energy on an anterior side or portion of the user that passes through biological tissues to be received on a posterior side or portion of the user.

In some examples, the LT apparatus (e.g., LT system) described herein may include a processing unit operably coupled to one or more sensors. The processing unit may be adapted to interpret the user-specific biometric data acquired by the sensors. Interpretation of the user-specific biometric data can be used to develop, supply, adjust, evaluate, etc. a treatment (e.g., treatment regime) applied by the LT system.

In some examples, the processing unit can use one or more algorithms, for the interpretation of the user-specific sensor data. For example, the processing unit (e.g., processor) can interpret user-specific biometric data using one or more algorithms related to determining a status, result, or other relevant result based on the user-specific biometric data.

In some examples, interpretation of the user-specific data can provide results that may influence, prompt, or otherwise be relevant to diagnosis, detection, prediction, etc. of a disease or condition. In some examples, algorithms within the LT system may be established, adjusted, adapted, included, excluded, etc. based on training of the system (e.g., processing unit algorithms) over a period of time. For example, a user may engage the LT suit and the sensors may begin to acquire data from one or more sensors. The data may be interpreted into an initial algorithm that is modified over a period of time until sufficient calculations provide for a user-specific algorithms that can be applied to subsequent user engagement.

In some examples, the therapeutic system may include an interface operably connected to the therapeutic system and configured to receive one or more inputs relating to the user. For example, the user interface may receive user input to generate a profile of the user that may adjust parameters of the therapeutic system (e.g., the sensors). In some examples, the interface may be in communication with one or more databases or electronic systems having data generated or established outside of the LT apparatus, which may be incorporated into the therapeutic system operations. For example, the interface may communication with one or more electronic medical record systems having user-specific information such as medical history, lab test results, examination notes, or other relevant information related to a disease or condition, or risk factor thereof. The therapeutic system may interpret this remote user-specific information and adjust one or more of the sensors or one or more parameters for the sensors operation to target sensor operation based on the remote user-specific information.

In some examples, an LT system may be in communication with one or more remote devices configured to control, adjust, evaluate one or more functions of the LT system (e.g., LT apparatus). For example, an LT system can have a communication system configured to receive and transmit data therebetween. A healthcare provider may be able to engage the remote device for adjustment based on additional user-specific biometric data, therapeutic strategies, etc.

In some examples, the LT apparatus may supply radiation energy via one or more light sources (e.g., light source arrays) as described herein. For example, a treatment regime may be established based on the sensor data or interpretation of the sensor data including treatment parameters such as treatment intensity, duration, anatomic location, sequence, etc. In some examples, the treatment regime may be adjustable based on subsequent data acquired by one or more of the sensors associated with the LT apparatus (e.g., LT suit). In some examples, the adjustment is dynamic and may increase or decrease or a combination in increase and decrease one or more of the treatment parameters based on the subsequently acquired data. For example, an initial treatment regime may be established based on the detection of a tremor and, after a period of time additional data may be acquired associated with persistence of the tremor that may cause the treatment regime to change one or more of the treatment parameters. In some examples, the treatment regime may terminate after a therapeutically effective treatment has been supplied.

The treatment regime or treatment protocol may be developed or established based on the interpretation of sensor data. Treatment intensity, duration, arrangement, frequency, etc. may be modified based on the sensor data or interpretation of the sensor data by the LT apparatus (e.g., the processing unit). For example, the optical sensors may acquire data related to the optical characteristics of biological tissue. A treatment regime can be established by the LT apparatus after interpreting the acquired data. The treatment regime may provide for increased intensity, higher frequency, shorter pulse duration based on the acquired data.

Each factor or aspect of the treatment regime may be adapted to the user-specific biometric data to provide optimal treatment.

In some examples, the treatment parameters of a treatment regime may be adjusted by sensor data while the user is engaging the LT apparatus. Sensors may continuously acquire data during use and the data may result in adjustments to the treatment regime or parameters of the treatment regime or both. For example, sensed data from one or more sensors may increase treatment parameters to increase the intensity of radiation energy supplied by the light sources.

The LT apparatuses may include an controller and power supply, including a controller and power supply with a user input/output (e.g., touchscreen) that is compact and may be coupled to an LT suit for controlling the suit and/or for communicating with one or more remote servers. Also described herein are LT apparatuses can be adapted for reliable and easy use by the wearer of the suit (e.g., in an at-home or studio setting). Also described herein are LT suit apparatuses that are easier to put on, adjust and maneuver in than traditional LT suits, and may allow movement and flexibility while maintaining reliable and sufficient positioning between the user and the multiple LT light sources. Any of the apparatuses described herein may include a user interface configured to enhance the case of operation and effectiveness of an LT suit. For example, described herein are apparatuses (e.g., systems) that may be used to regulate the safe and effective operation of the LT suit, including limiting or preventing operation in ways that may be less effective and/or dangerous to the user.

In general, an LT apparatus may include an LT suit having a plurality of light sources coupled or couplable thereto, wherein the light sources are positioned/locatable on the LT suit in an arrangement that provide treatment while preventing danger to the user. Individual light sources of the LT suit may be controllable by a processor(s) to deliver pulses of light energy to a user who is wearing the LT suit. In some examples, the processor controls the light sources based on data and information received from the sensors. When an energy pulse (e.g., light energy) is delivered via one or more light sources, light is transmitted from the one or more light sources to a portion of the user's body (e.g., through one or more layers of the dermis).

In some examples, a LT apparatus may have additional stimulation elements in addition to the one or more light sources. For example, an LT apparatus may have one or more light sources configured to supply light therapy treatment and one or more electrodes configured to supply electrical stimulation. A LT suit having a plurality of electrodes coupled or couplable thereto, wherein the electrodes are positioned/locatable on the LT suit in an arrangement that provide treatment while preventing danger to the user. Individual electrodes of the LT suit may be controllable by a processor(s) to deliver pulses of electrical stimulation to a user who is wearing the LT suit. In some examples, the electrical stimulation may be supplied in combination with the light therapy. In some examples, the electrical stimulation and light therapy may be supplied separately from one another (e.g., via different treatment regimes). In some examples, the processor controls the electrodes based on data and information received from the sensors. When an energy pulse (e.g., electrical stimulation) is delivered via a pair of electrodes, electrical current (i.e., the flow of charged particles) flows from one electrode (of the pair), through a portion of the user's body (e.g., through muscle tissue underlying the pair of electrodes), and to the other electrode (of the pair). The user's body completes an electrical circuit that includes the pair of electrodes, thereby allowing electrical current to flow between the pair of electrodes during operation of the LT suit, as electrical impulses are delivered via the electrodes. A pair of electrodes may include two electrodes that correspond to a common channel of multiple channels that are used to deliver electrical impulses, channel-by-channel, during operation of the LT suit. A pair of electrodes may also include two electrodes that allow for electrical current to flow therebetween during operation of the LT suit, one electrode of the pair operating as a positive electrode (anode) and the other electrode of the pair operating as a negative electrode (cathode). With alternating current (AC), each electrode of a given pair may reverse current with each cycle (or frame). That is, each electrode may change from a positive electrode (anode) to a negative electrode (cathode) with each cycle (or frame).

For example, FIGS. 1A-1F illustrate an example of an LT system as described herein. This example shows a wireless, whole-body light therapy (LT) system that includes a suit/vest, a lower body (pants/shorts) portion, and a combined power supply/controller/user interface. FIG. 1A shows an example of an upper 101 and lower 103 under suit. The under suit may be configured to allow sufficient positioning between one or more light sources and the underlying skin in the appropriate region of the body (e.g., over the target muscle groups). For example, the under suit may include openings configured to allow unobstructed transmission of light from one or more light sources. The under suit may be configured to conform to the patient's body, e.g., as a stretch and/or compression garment. The under suit may be washable.

FIG. 1B shows an example of an upper torso (e.g., vest) portion 105 of the LT suit and a lower body 107 portion of the LT suit. The upper torso portion and the lower body portion may support the plurality of light sources 109, which may be integrated into the apparatus. The upper torso and lower body portions may include one more adjustable straps allowing the user to attach and adjust the fit. The upper torso 105 portion shown in FIG. 1B is configured as a vest, and the lower body region is configured as a chaps-like configuration to be worn over the under suit. In some examples the under suit and the upper torso and lower body regions may be integrated together into a single garment, as shown in FIGS. 4A-4B, below.

In any of these examples the LT suit may have light sources strategically positioned so as to apply light therapy treatment to the target region of the user, such as the quadriceps (quads), hamstrings, glutes, abs, chest, lower back, mid back, upper back (trapezius), biceps and triceps, and/or calves.

In any of these examples, the electrical connectors (e.g., "cables") may be integrated into the suit. For example, coupling the power supply/controller into the suit may automatically couple the light sources to the power source/controller via a single (e.g., multiplexed) connection, dramatically simplifying the contact. For example, the integrated electrical connectors may be coupled via internal cabling that is arranged so as not to limit freedom of movement.

The light sources (e.g., light source arrays) of the LT suit may be arranged in the LT suit to cover parts of the user's body in order to direct radiation energy to target anatomy through the delivery of light energy pulses directed towards the user's skin. In particular, as will be described in greater detail below, the light sources described herein may be arranged in a manner that increases the ability of the light sources to remain in reliable communication with the patient's skin and therefore provide energy to the underlying biological tissue during a treatment.

For example, upper body portion (e.g., torso, including chest, vest, etc.) may be worn on an upper trunk of the user's body. The upper body portion may be coupled to the lower body portion, e.g., via one or more mechanical and/or electrical connectors. Thus any of the buckles/straps shown may include both mechanical and electrical connectors.

In any of these apparatuses the connectors 111 (e.g., buckles) may be configured to make and/or confirm electrical connection. For example, the power source/controller may sense and/or confirm that each connector is coupled and/or secured. The controller may, for example, provide a test current/pulse to confirm the electrical connection (via. the electrical properties of the connection, showing an open circuit if not properly attached). The electrical contact with the skin of the user may similarly or additionally be confirmed by the system and may be used as part of a safter interlock and/or power-saving protocol.

In some examples the upper body portion may comprise a left front portion, a right front portion, and a back portion. In some embodiments, the left front portion has one or more light sources positioned on an inner surface of the left front portion and within a top half of the left front portion, while the right front portion has one or more light sources positioned on an inner surface of the right front portion and within a top half of the right front portion. In this manner, when the body of a user is wearing the LT suit, light sources may be disposed on (or atop) one or more left pectoral muscles of the body, and the light sources may, therefore, be positioned on a first (e.g., left) side of a midsagittal plane of the body, as well as on a first (e.g., front) side of the frontal plane of the body. A second pair of electrodes may be disposed on (or atop) one or more right pectoral muscles of the body, and the second pair of electrodes may be positioned on a second (e.g., right) side of the midsagittal plane of the body, as well as on the first (e.g., front) side of the frontal plane of the body.

FIG. 1C also illustrates an example of an integrated controller/power supply 113. In this example, the integrated power supply/controller includes a separate mechanical and electrical connector; however in some examples the same connector may make both mechanical and electrical connection with the LT suit. For example, in FIG. 1C the apparatus includes a pair of electrical connectors 115 that may attach to electrical coupling contacts on the suit. In FIGS. 1A-IF only a single pair (e.g., anode/cathode) of connectors are shown. In some examples, multiple connectors/contacts may be used. In this example the suit may include an integrated multiplexing electrical manifold that may direct and/or switch the applied energy to the one or more light sources to which power is to be applied to apply LT. In general, power may be applied to individual light sources at a time (sequentially) or in a manner so that nearby light sources in communication with the body are not concurrently activated by the application of electrical energy. The power supply/controller 113 may be held to the LT suit by a pocket and/or a mechanical connector such as Velcro, straps, etc. Multiple mechanical connectors may be included.

FIGS. 1D and 1E illustrate examples of arm light source supports 119 including light sources 109 that may be used to apply light energy to the biceps and/or triceps. In this example, in which the arm light source supports are not integral with the upper/torso portion 105, addition external cables 121 may be used to connect the arm light sources to contact 117 on the upper/torso portion (vest) 105. Alternatively in some examples the light sources and/or light source supports may be integrated into an upper/torso LT garment.

In any of these apparatuses, the back of the upper body portion of the LT suit may include multiple light sources 109, including, e.g., light sources positioned on an inner surface of the back portion and within a left half of the back portion, and light sources positioned on the inner surface of the back portion and within a right half of the back portion. When the body of a user is wearing the LT suit, the light sources may be disposed on (or atop) one or more left back region of the body, and the light sources may, therefore, be positioned on the first (e.g., left) side of a midsagittal plane of the body, as well as on a second (e.g., back) side of the frontal plane of the body. Meanwhile, the light sources may be disposed on (or atop) one or more right back muscles of the body, and the fourth pair of electrodes may, therefore, be positioned on the second (e.g., right) side of the midsagittal plane of the body, as well as on the second (e.g., back) side of the frontal plane of the body. Other configurations and arrangements may be used.

In some examples, where the LT apparatus has one or more electrodes in addition to the light sources, the electrodes may be wettable electrodes that include an absorbent substrate (forming a fluid/wetting reservoir) in electrical communication with the electrode and configured to contact the user's skin (either directly or through the under suit). These wettable electrodes are configured to hold a conductive fluid (e.g., water, including saline) that may help make a reliable electrical contact with the user's skin, and maintain the electrical properties, even as the user sweats during physical exercise wearing the LT suit. This may be particularly helpful, as these wettable electrodes may be configured (by size and position) to allow continuous electrical contact with the skin without having the electrical properties significantly change doe to sweating. FIG. 1F illustrates an example of a LT apparatus including a hood or portion of the LT suit configured to engage and/or supply light energy to the user at one or more regions above their neck. For example, a hood or head piece element of the LT suit may be configured to direct or supply light therapy to a user's head, face, eyes, etc.

The apparatus shown in FIGS. 1A-1F does not show the associated application or other components of the apparatus that may be used to control the applied power to drive LT of target muscle(s). The controller 113 may include a user interface (e.g., touchscreen) for direct communication with the user and/or it may be configured to wirelessly communicate with one or more external processors, such as a smartphone, tablet, computer, etc. In some examples the user may communicate via a smartphone or tablet (not shown). In some examples the user may communicate with a remote processor. Any of all of the controller/power supply, smartphone, and/or remote processor may include software, firmware and/or hardware for engaging with the user and/or for controlling operation of the apparatus, including for engaging in one or more safety protocols to prevent a user from exceeding a predetermined or calculated amount of LT to individual body regions (muscled) and/or the entire body based on the user's condition and prior operation of one or more LT apparatuses.

FIG. 2A shows an example of an upper torso portion 105. In this example, the upper torso portion includes a connector port 201 that may coupe with an integrated controller/power supply (not shown). The apparatus also includes a plurality of mechanical connectors (e.g., clasps, snaps, etc.) 202, and a plurality of adjustable straps (e.g., Velcro straps) 203, including side straps 204. The upper torso portion in this example also includes a zipper 205. A plurality of light sources 206 may also be integrated into the upper torso portion. The apparatus may also include connectors (e.g., buckles) 207 for coupling to a lower portion. Any of these connectors and/or straps may be adjustable and may include retainers 208.

FIG. 2B shows an example of a lower portion 107. The lower portion may also include one or more mechanical and/or electrical connectors 216 for coupling to an upper portion (onto which a power supply/controller may be attached). Alternatively or additionally the lower portion may hold the controller/power supply (and may provide power and control operation of the upper portion(s)). For example, the lower portion may include a pocket and/or attachment site 213 for the controller/power supply and/or may include a connector port 211. The lower portion may include a hip belt 212 for securing the apparatus to waist (e.g., onto or over an under suit). In some examples the apparatus may include adjustable straps and/or buckles and/or other components to adjust the fit 216. The lower portion may also include one or more light sources assemblies (including electrical pads 215) for applying LT to a region of the lower body.

FIG. 2C illustrates an example of an arm light source support 119 shown from the top 229 and bottom 228 (user-contacting side). The arm light source support may include one or more attachments (e.g., straps 221) including loops 223 and/or Velcro attachment portions 224. The arm light source support may also include one or more light source assemblies 222.

FIGS. 3A and 3B illustrate examples of LT suits as described herein, worn on a user. In FIG. 3A the LT suit including all of the components described above, including an upper portion 305, a lower portion 307. The upper and lower portions are coupled together, and a power supply/controller 350 is shown coupled to the lower portion. The user is also wearing an upper 301 and lower 303 under suit.

The LT suits shown may include light sources on the legs, e.g., quadriceps, buttocks, lumbar region, back, trapezius, and one or more on the abdomen, pectorals, and arms. The positions may be adjustable, within a predetermined or arbitrary range. For example, on the legs, the lower portion may be configured to allow adjustment of the position(s) of the light sources in one or two positions, such as over the medial thigh muscle or the medial and lateral muscles. light sources may be positioned between 5 cm and 10 cm apart. In another example, the apparatus may be configured to allow adjustment of the position of the muscles of the abdomen, including adjusting the light sources to be further or closer apart. The central abdomen may be adjusted and/or a more laterally separated position may be used.

FIGS. 4A-4B illustrate another example of an LT suit apparatus similar to that described above, in which an under suit may not be needed. In this example, the apparatuses include a wetsuit-like appearance, and may be formed, at least in part of an elastic material, such as a polymeric material (e.g., neoprene, etc.) that is breathable, and is configured to hold the light sources (e.g., the light source assemblies) in contact with the skin. For example, in FIGS. 4A and 4B, the LT suit may include an upper 405 and a lower 407 portion, or may be a unitary suite (e.g., integrated upper and lower portion). The suite may be formed of an elastic fabric and includes a closing system 447 (e.g., zipper). The light source assemblies may be integrated into the suit but may be configured to allow selection of one or more alternative positions, e.g., to allow the user to adjust the light sources. Thus, the light sources may include an input (e.g., strap, selector, etc.) for allowing or locking internal movement of the electrode assembly position. In the example apparatus shown in FIGS. 4A and 4B the light sources may be coupled to the power supply/controller 450 by internal wires (not visible).

In some examples, the light source assemblies or light sources described herein may comprise one or more sensors as described herein. For example, FIG. 4B illustrates an exaggerated arrangement of sensors positioned throughout the LT apparatus. Sensors 412 are shown and examples of sensor elements (e.g., a transmission element or a receiver element) 413 may be positioned at a location on the LT apparatus to operably communicate with the biological tissues of the user. In some examples, the sensors 412 are integrated or otherwise associated with the light sources or light source assemblies. In some examples, the sensors 412 are located or locatable on an interior of the LT suit such that they contact or are substantially proximal to the user's skin.

As mentioned above, any of these apparatuses may include light source assemblies configured as wet or wettable electrodes. For example, these apparatuses may be configured so that fluid (e.g., water, saline, etc.) may be added to wet a skin-contacting surface of the light source assembly. In some examples, the LT suit comprises one or more electrodes, as described herein, configured to supply electrical stimulation in combination with, or alternatively to the light energy from one or more light sources. Electrical contact is essential to proper function and control of an LT apparatus. FIG. 5 illustrates an example of the application of fluid (e.g., water) 567 via a spray bottle to wet electrodes 565 (and in particular, to wet the porous skin-contacting surface of the electrode) on the inside of the suit 563. In some examples the suit may include one or more ports into which a fluid (e.g., water, saline, etc.) may be added. The fluid may be a conductive fluid.

Any of the apparatuses described herein may include sensors, e.g., motion sensors, position sensors, etc. that may confirm the position and/or activity of the user. Sensors may be included with the one or more light sources and/or may be included with the controller (or power supply and/or controller, including integrated power supply/controller). The sensor(s) such as an accelerometer, may be used to confirm that the user is performing a predetermined action/exercise (as described below) and may therefore coordinate the application of the LT with the prescribed movement(s). The sensor(s) may also be used as a safety trigger, for example, stopping or pausing (or in some cases decreasing) the application of LT based on the sensed motion and/or position.

In general, the suits described herein may be cleaned and maintained by the user. For example, the suits may be treated with an antibacterial solution and rinsed with water. An anti-odor product may be applied following each use, and/or after applying the antibacterial solution. The suit may be dried, e.g., by handling in a drying area. An air-drying system may be used to expedite drying. Heated or room-temperature air may be used to dry the suit. In general, the suit may be washed, e.g., by soaking in a soapy solution at low concentrations. The suit may be washed and/or rinsed in cold water to clean (including removing excess salts from the added fluid and/or sweat).

Also described herein are power sources and/or combined power sources (e.g., batteries) and controllers. FIG. 6 illustrates one example of a power source (e.g., battery) 600. This example may be used with an apparatus as shown herein and may include a simple user interface showing power level 661, wireless connectivity 662 (e.g., Bluetooth connection), etc. In some examples, described in greater detail below, additional user interface information (e.g., touchscreen) may be included. Any of theses apparatuses may include an audio output 663 (e.g., speaker) that may be used as an output. The power source/controller may be, e.g., 500 g or less (e.g., 450 g or less, 400 g or less, 350 g or less, 300 g or less, 250 g or less, etc.). The apparatus may be relatively small (e.g., 20×10×5 cm or less, 18×8×3 cm or less, 16.5×8×3 cm or less, etc.). The apparatus may also include an on/off button that may be manually or automatically controlled. Any of these power sources may be configured as batteries, such as lithium ion (Li-Ion) batteries. The power source may include a charging port (e.g., mini-USB port). In some examples the power source may also or additionally include a port for connecting to the LT suit, and/or a cable connected to the LT suit. As mentioned above, in some examples the power source (or power source/controller) may be configured to be secured within a pocket in the suite and may electrically couple to the suit while within the pocket.

Any of these power sources and power source/controllers may include one or more emergency shutoff controls, or an override shutoff control. The shutoff control may be configured to immediately stop the application of power to the light sources. In some configuration the shutoff control may be configured to completely shut off the apparatus; in other examples, the shutoff control may continue sensing/monitoring and processor functions but may disable the application of power to any of the light sources (e.g., for delivery of LT) until a rest condition is satisfied. For example, in some examples an emergency shutoff control (or an override shutoff control) may be included on the outer surface of the battery or battery/controller. In some examples the suit may have an integrated shutoff control on the front outer surface of the suit that may be easily actuated by the user.

Any of these suits may include one or more sensors (e.g., physiological sensors), including heart rate sensors, pulse oxygenation sensors, respiratory sensors, etc. In some examples the apparatus may be configured to trigger a safety shutoff of LT if the sensors detect user physiological signals that exceed a predetermined safety threshold. For example, if the heart rate exceeds, e.g., 180 bpm (e.g., 155 bpm, 160 bpm, 165 bp, 170 bpm, 175 bpm, 180 bpm, 190 bpm, 195 bpm, 200 bpm, 205 bpm, etc.), and/or if the blood pressure exceeds a predetermine range, etc.

FIGS. 7A-7D illustrate one example of a combined power source/controller 700. In this example the combined power source/controller including a touchscreen input 771, and may include one or more additional inputs 772, including an emergency shutoff control. The combined power source/controller may also include an attachment (input) 775 for coupling to a charging source and/or for coupling to an input/output (including a cable input/output) on the LT suit. FIGS. 8A-8E show another example of a combined power source/controller 800 similar to that shown in FIGS. 7A-7D, also including a display screen (which may optionally be a touchscreen) 871 and one or more inputs 872, including, e.g., an emergency shutoff control. FIGS. 9A-9F shown another example of a combined power source/controller including a display 971 and inputs 972. This example also shows nan interface or adapter 976 for coupling to the LT suit and/or a charger for charging the power supply integrated with the controller.

FIG. 10 shows an image of a prototype combined power source/controller 1000, with the outer housing removed, showing the display screen 1071 and inputs 1072 visible. The controller may include one or more processors, memory, timer(s), and control circuitry, including wireless circuitry and/or power control circuitry.

FIG. 11 illustrates one example of an LT apparatus, including an LT suit 1103, including a controller/power source that may operate with software on one or more of a user device (e.g., smartphone 1107), remote server 1105 and/or an instructor (or class) processor 1111. In FIG. 11, the LT suit 1103 may be controlled by a worn controller 1105. The locally worn (LT suit) controller may include the safety override control and may generally control the application of LT to the light sources in the suit, as described above. The locally worn controller (e.g., an integrated power supply/controller 1105) may communicate wirelessly, e.g., via Bluetooth (or other wireless technique) to any of the user device 1107, instructor/class processor 1111 and/or remote server. For example, the suit, which may be identified by a unique identifier associated with the user (e.g., name, number, address, etc.) may receive instructions for delivering a predetermined LT protocol corresponding to a desired training regimen. The protocol may be delivered by the local controller but may be run in combination with the remote server, instructor class/server (for example, for group exercise) or from the user device (e.g., smartphone 1111).

In particular, the apparatus may be configured so that during a training episode, a selected or prescribed training regimen may be provided to the user, instructing the user to perform one or more actions. As mentioned above, a sensor, e.g., a motion sensor (e.g., accelerometer) may be included as part of a combined power source/controller and the controller may confirm that the user has begun, is in the midst of continuing to perform, or has completed, a prescribed movement before applying or continuing the application of LT.

In general, the application of LT may be targeted to a particular biological tissue corresponding to a particular activity. For example, the apparatus may be configured to apply a workout targeting a particular user goal, such as increasing endurance, mobility, and/or strength. These workouts may include a defined set of movement or actions (e.g., exercises, yoga/stretching poses or movements, etc.) and may be presented to the user concurrently with the application of LT to one or more biological tissues related to the movements or actions.

In general, these apparatuses may include software that may perform any of these methods. For example, the software may be an application software (app) that is configured to run on the user's device (e.g., smartphone) and/or on the power supply/controller. The software may be configured to control the LT to a particular use or to coordinate the control of a group of users that may be utilizing the LT apparatus for a similar objective, therapy, or desired outcome, e.g., as part of a class. For example, FIG. 12 schematically illustrates a user software 1207 that may be used to assist the user in establishing a LT treatment regime for a desired outcome or impact.

In some examples, the LT apparatus can have a plurality of electrodes configured to supply electrical stimulation during an exercise session. Software may be used to coordinate electrical stimulation during a particular class or exercise. The application software 1207 may allow a user to select a particular training session and/or class and may coordinate the application of the training session and the application of the electrical stimulation. In some examples the application software may record the progress and may adjust the maximum possible electrical stimulation intensity/power for each session, as described above. The application software may therefore automatically adjust the settings (energy settings) for each workout.

The sessions ("workouts') may start the energy settings with settings based on the individual base settings (baseline) as mentioned above, and the apparatus may optimize the maximum possible LT intensity and/or power for each setting, as well as the onset of this maximum during the course of a session. As described above, this may therefore be customized to each user and specific to their body and fitness level and configured to prevent harm or discomfort to the user. The apparatus may recalibrate the base settings. In some examples, the electrodes may supply electrical stimulation before, during and/or after exercise and the LT apparatus light sources can supply LT after to promote recovery and support to biological tissues after the exercise. In some examples, the exercise and/or activity of the electrodes and electrical stimulation can be interpreted by the LT apparatus for the development of a LT recovery treatment regime. For example, based on the intensity and duration of electrical stimulation, LT parameters can be adjusted to optimize application of LT for recovery.

For example, strength training routines may include resistance exercises (weights, bands, bodyweight, etc.), core strength, high-intensity interval training, etc., and may target specific muscles. The apparatus may automatically apply LT in a coordinated manner with the presentation (and presumed performance) of the movements and/or may detect the user's movements and apply LT when the user is performing the appropriate corresponding movement or shortly thereafter. In some examples the apparatus may therefore provide immediate feedback to the user that the movement is being performed within a desired level of activity, further reinforcing the effects of the LT.

In any of these apparatuses, the intensity of the apparatus may be automatically adjusted to either adjust the applied LT or to set the range of LT intensities within which the user may select intensities (e.g., high, medium, low, off, or X % of 100%, where the range of 100% is set automatically by the system).

In particular, the apparatuses described herein may control and/or set the maximum LT power/intensity that may be applied to a particular user based at least in part on one or more of: (1) an initial baseline (e.g., starting baseline) for the user; (2) the user-provided input(s); and (3) the historical (including within the last z hours or days) application of LT by the same user. The apparatus may control the applied LT power/intensity specific to biological tissue. Alternatively, the maximum power/intensity of the LT applied may be the same across all biological tissues. The apparatuses described herein may adjust the LT power/intensity by adjusting one or more of the light pulse wavelength applied (e.g., between 0/off and 2000 nm, e.g., between 0-100 nm, between 100-500 nm, between 500-1000 nm, between 1000-1500 nm, between 1500-2000 nm, or more, or any range within these etc.), the energy applied (e.g., between about 0.01-1 milliwatts (mW), between about 1-5 mW, between about 5-10 mW, between about 10-15 mW, between about 15-20 mW, etc. or any range within these), the pulse width. In some examples the LT power/intensity may be modulated by adjusting the ramp-up time (time to ramp up to a maximum applied current) and/or by adjusting the frequency within an application session (increasing or decreasing the frequency).

In some examples, the wavelength of light supplied by the one or more light sources may be within a range of a biological window of wavelengths. For example, a biological window wavelength range may be from 500 nm to 1100 nm (e.g., 600 nm-1000 nm). In some examples, the wavelength of light supplied by the LT apparatus as part of the treatment regime may be configured to increase oxygenation capacity of red blood cells (e.g., a wavelength of 800 nm to 825 nm). In some examples, the wavelength of light supplied by the LT apparatus as part of the treatment regime may be configured to affects mitochondria calcium processing, case pain, stimulate circulation, relax muscles, etc. (e.g., 950 nm to 1100 nm). In some examples, the wavelength of light supplied by the LT apparatus as part of the treatment regime may be configured to impact tissue metabolism (e.g., 1050 nm to 1100 nm). In some examples, the wavelength of light supplied by the LT apparatus can be determined based on a depth of penetration required for the therapeutic application. In some examples, the wavelength of light supplied by the one or more light sources may be within a range of an optical window of wavelengths. For example, a biological window wavelength range may be from 650 nm to 900 nm.

In some examples, the automatic adjustment of the intensity or the treatment parameters or treatment regime may be adjusted based on information acquired by the sensors (e.g., optical ultrasonic, electrical sensors). In some examples, the adjustment may be triggered based on a predetermined interval or duration of stimulation. In other examples, the user may be able to selectively engage the controller to initiate an update or adjustment procedure including the operation of the sensors to acquire data and provide updated sensor data for processing by the LT apparatus that can be used for adjustment.

Figure 15:
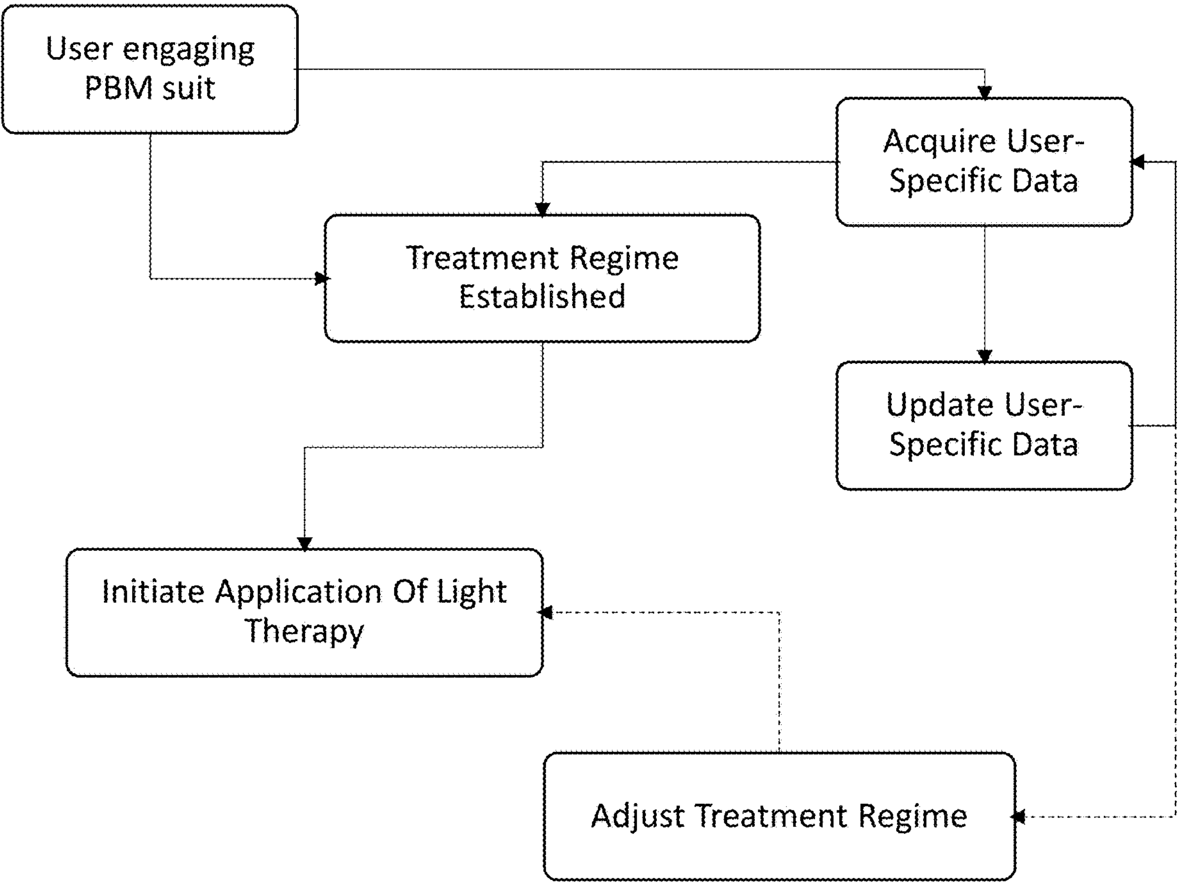
FIG. 15 schematically illustrates an example of a use for an LT apparatus, as described herein.

FIG. 15 illustrates an example of a method of using an LT apparatus. A user first engages the LT suit by wearing one or more of the suit portions (e.g., the torso portion or the lower portion described above). In some examples, the light sources (e.g., light source arrays are positioned on the LT suit such that wearing the suit results in optimized placement and positioning of the light sources for therapy (e.g., treatment). The treatment regime can be established before or after the user engages the suit. In some examples, a LT treatment regime may be predetermined by the user. For example, a user may select a predetermined or existing treatment regime from a database, from previous use, from pre-loaded options within the LT apparatus, etc. Alternatively or additionally, a healthcare provider may predetermine a treatment regime applied by the LT apparatus. In some examples, after the user engages the LT suit, the one or more sensors acquire initial biometric data to be interpreted by the LT system and may contribute to the development of a treatment regime. A feedback loop of sensors acquiring user-specific biometric data can include one or more sensors of the LT apparatus acquiring data continuously, periodically, selectively (e.g., manual acquisition), as necessary, etc. that may be used in establishing, adjusting, or otherwise modifying the treatment regime. In some examples, the acquired biometric data may trigger the treatment regime to start, stop, pause, or otherwise change from an initial treatment regime. After the treatment regime is established, the LT apparatus can initiate application of treatment (e.g., light therapy) to the user based on the treatment regime.

In general, the apparatuses described herein may be configured to apply power to just a subset of the light sources (e.g., less than all the light source assemblies/arrays) and may apply power to separate light sources corresponding to different biological tissues in an alternating manner, to avoid concurrent treatment of multiple light sources.

The apparatuses described herein may be configured to safely apply LT by controlling the applied energy (e.g., wavelength and/or current and/or pulse width and/or ramp-up/ramp down time) based on a combination of on one or more of: (1) an initial baseline (e.g., starting baseline) for the user; (2) the user-provided input(s); and (3) the historical (including within the last z hours or days) application of LT by the same user. In particular the apparatuses described herein may automatically set the maximum applied LT power and/or intensity by estimating a maximum specific to a particular user base on the user's specific baseline and the user's recent (e.g., within the last z hours, where z is between about 8 hours or less, about 24 hours or less, about 36 hours or less, about 48 hours or less, about 60 hours or less, about 72 hours or less, etc.).

An initial baseline may be set based on a user's initial response to questions, such as the user's age, fitness level, general or specific health concerns, health objectives, cosmetic objectives, etc. In some examples the apparatus may perform an automated question and answer/testing session to set a baseline/initial user level. For example, the user may respond to questions regrading their ability to feel certain LT applications (e.g., heat). The user may also be asked to perform various actions (e.g., exercises) while wearing the apparatus and/or without wearing the apparatus and may provide feedback by self-reporting or via one or more sensors (e.g., heart rate, pulse oxygenation, accelerometer/position sensors, etc.).

The baseline data may be estimated, and an initial maximum level of LT intensity/power may be determined. The initial baseline may be determined from population data of similarly-situated users (e.g., by age group, gender, health, weight, height, etc.). Initial baseline data may be set in part based on user-reported response to a variety of different LT treatment levels for each (or a subset of) biological tissue.

A dataset for each user may be maintained locally (e.g., on the user-specific LT suit/controller) and/or may be kept in a remote database and accessed by the user-specific LT. The user information (data) may include specific responses to the initial baseline data collection and/or the initial baseline values estimated by the system. In some cases, initial baseline values for different muscles may be determined based on a patient-specific estimate for one or more biological tissues (e.g., target tissue for determining treatment regime and energy parameters etc.).

User-specific baseline data may be adjusted periodically. User-specific data may be secured. For example, if user-specific date is recorded in a remote database it may be anonymous and indexed by a separately secured key corresponding to a particular user. In some cases, baseline information may be specific to an LT system (e.g., LT suit) and/or specific to a user. A user may be uniquely associated with a particular LT suit).

The maximum LT intensity/power that may be applied to the user may be adjusted with operation of the system. In general, the initial (e.g., baseline) LT intensity/power may be set low, to avoid harming the user. With consistent use, the maximum intensity may be adjusted. For example, the apparatus may be configured to increase the maximum intensity with regular use and/or with user-requested increase.

As a safety, any of the apparatuses described herein may reduce and/or reset the maximum if LT is not applied within a particular timeframe (e.g., if it has been more than x hours or days since the last LT use). For example, for every x hours that the user has not operated the LT apparatus the maximum intensity/power may be scaled towards the initial baseline (e.g., if no LT has been performed by the user within 4 days, 5 days, 6 days, 7 days, 8 days, 9 days, 10 days, 11 days, 12 days, 13 days, 14 days, etc.).

Further, the system may lock out or prevent LT from being applied more frequently than a predetermined time period. For example, the apparatus may be configured to prevent the user from applying LT more than one session (or more than a maximum number of minutes or a maximum aggregate energy) every x hours or day (e.g., no more than once per 20 hours, per 24 hours, per 30 hours, per 36 hours, per 40 hours, per 44 hours, per 48 hours, per 52 hours, per 56 hours, per 60 hours, etc.).

Any of the apparatuses described herein may gradually increase the intensity of the LT (e.g., the power of the LT), e.g., by increasing one or more of the wavelength, pulse width, energy, etc., over the course of a treatment session, up to a limit of the maximum intensity. For example, the apparatus may automatically increase the applied LT power from an initial starting level up to 100% of the maximum LT power/intensity available to the patient as calculated for a particular session (based on the baseline, historical, and/or user-selected input).

Any of these apparatuses may include a user interface that may be displayed, for example, on the power supply/controller and/or on the user apparatus (e.g., smartphone, television/display, etc.). This user interface may include input/outputs for each of the LT light sources and/or corresponding muscle groups, including showing an intensity level (e.g., as frequency, amplitude, pulse width, and/or some combination or derived value of these, e.g., generically "intensity"). The user may be permitted to select a value for each or some of these which may be limited to the maximum level selected or set by the system. The user interface may also show the corresponding positions/movements/exercise and/or may display an instructor or model performing or guiding the user in performing them. In general, the apparatus (e.g., software, firmware, etc.) may coordinate the application of LT via the LT suit to the session being performed, including coordinating activating of the appropriate light sources.

The techniques and systems described herein may also allow for one or more devices to conserve resources with respect to communications bandwidth resources, processing resources, memory resources, power resources, and/or other resources, as described herein. Additional technical effects can also be realized from an implementation of the technologies disclosed herein. Described herein are example processes, as well as systems and devices comprising one or more processors and one or more memories, as well as non-transitory computer-readable media storing computer-executable instructions that, when executed, by one or more processors perform various acts and/or processes disclosed herein.

In some examples, the LT apparatus as described herein is used as a therapeutic device to diagnose, treat, prevent and/or detect a disease and/or condition. Therapeutic applications may relate to any disease or condition including diseases or conditions that may be detectable with minimally invasive or non-invasive sensors associated with the LT apparatus. In some examples, disease profiles may be stored, developed, established, acquired, or otherwise known to the LT apparatus and can be used to compare or cross-reference the user-specific biometric data obtained by the LT apparatus via the one or more sensors.

A disease profile may include known characteristics of a disease or condition such as symptoms, risk factors, genetic factors, biological factors, physiological factors, and/or any other relevant information associated with a disease state. The disease profile may provide a similarity score based on the comparison of the disease profile to the user-specific biometric data acquired by the LT apparatus. For example, a similarity score may indicate a similarity between the observed or acquired user-specific biometric data and the known characteristics of a disease or condition.

In some examples, an LT apparatus as described herein can detect a disease or condition. Detection of a disease or condition may include the LT suit sensing or analyzing user-specific factors relating to a disease of condition. One or more sensors within the suit may be adapted to receive biological and/or physiological data relating to the user and associated with a sign, symptom or other manifestation of a disease or condition. For example, detection may include the accelerometer sensors detecting a change in user-related acceleration and may signal a contemporaneous or impending incidence of biological activity (e.g., tremors) associated with a disease. In some examples, more than one type of sensor detect different user-specific biometric information that is interpreted and compiled by the processor for consideration as an incidence of detection of disease-related biological activity.

Detection may include identifying triggering events associated with a symptom of a condition or disease. The detection may be sufficient to identify factors supporting a prediction of an impending disease-related biological activity. For example, electromyography sensors may sense electrical impulses prior to involuntary muscle activity associated with a disease. Another example may include more than one sensors acquiring different biometric data that may be combined and interpreted by the processing unit to establish a prediction of impending disease-related biological activity.

For any of the applications of the LT apparatus described herein, a threshold may be established related to the user-specific biometric data detected by the sensors. A threshold may be a user-specific threshold based on a user engaging the LT apparatus (e.g., the user wearing the apparatus) for a period of time. In establishing a threshold, the duration of time may begin with a first use as the sensors begin to acquire user-specific data. As data is accumulated by the LT apparatus, patterns, rhythms, or other natural fluctuations in the user-specific biometric data may be incorporated into establishing a threshold specific to the user. For example, developing a threshold with the LT apparatus may be a calibration of the LT apparatus for a specific user.

In some examples, developing a threshold or standard values associated with the biometric data detected by the sensors may be predetermined. For example, known values include a range of values with a minimum and maximum that can be considered to be a healthy state. A healthy state value range may include an upper limit or lower limit associated with the particular biometric factor being evaluated. In some examples, predetermined thresholds may be adjusted or established by an individual (e.g., a healthcare provider) based on known acceptable or healthy-state values for a particular biometric factor.

In some examples, an LT apparatus as described herein may diagnose a disease or condition. Diagnosis of a disease or condition may include the LT suit sensing or analyzing user-specific factors relating to a disease of condition. One or more sensors within the suit may be adapted to receive biological and/or physiological data relating to the user and associated with a sign, symptom or other manifestation of a disease or condition. In some examples, diagnosing a disease or condition may include an LT treatment as a test or challenge of one or more biological tissues. The diagnostic LT challenge may be supplied by one or more light source assemblies, as described herein. In some examples, the diagnostic LT challenge may be supplied according to a testing regime based on the user-specific information, predetermined user information, one or more disease profiles, one of more evaluation procedures based on a disease profile, etc. For example, diagnosing a disease with an LT apparatus as described herein may include a user engaging (e.g., wearing the LT suit) the LT apparatus and initiating diagnostic protocols. The one or more sensors may acquire or detect user-specific information and one or more light source assemblies may supply an light therapy energy pulse or treatment to challenge or test associated biological tissue (e.g., muscle tissue) which can illicit a physiological response. The response may be detected by one or more sensors and the data may be sent to the processor for interpretation. The processor may interpret the data and compare detected user-specific information against disease profiles to present a diagnosis.

Diagnosis may include input from remote sources (e.g., a healthcare provider). Data acquired by the LT apparatus may be transmitted for further evaluation to a remote device or database for further consideration.

In some examples, an LT apparatus as described herein may treat a disease or condition. Treatment of a disease or condition may include the LT suit sensing or analyzing user-specific factors relating to a disease of condition. One or more sensors within the suit may be adapted to receive biological and/or physiological data relating to the user and associated with a sign, symptom or other manifestation of a disease or condition.

Treating a disease with an LT apparatus, as described herein, may include LT supplied by one of more electrodes (e.g., electrode assemblies) based on user-specific biometric data. In some examples, the supplied LT may be dynamically adjusted based on the user-specific biometric data. In some examples, the LT may be dynamically adjusted based on a known or suspected disease of the user. In some examples, the LT may be adjustable by the user or by another individual (e.g., a healthcare provider) through engaging the interface of the system to adjust LT maximum, minimum, or values therebetween.

In some examples, an LT apparatus as described herein may prevent a disease or condition. Prevention of a disease or condition may include the LT suit sensing or analyzing user-specific factors relating to a disease of condition. One or more sensors within the suit may be adapted to receive biological and/or physiological data relating to the user and associated with a sign, symptom or other manifestation of a disease or condition. In some examples, prevention may relate to the prevention of a sign or symptom of a disease or condition. Preventing a disease of condition may include interpretation of user-specific biometric data that is associated with a prediction or evaluation related to impending disease-associated biological activity. For example, the LT apparatus may acquire user-specific biometric data related to an impending stroke or tremor. After acquiring the data, the LT apparatus may establish and execute a treatment regime based on the predicted or observed disease-associated biological activity. By suppling the light therapy prior to or following the disease-associated biological activity, the LT apparatus may prevent the incidence of the disease-associated biological activity (e.g., the treatment may prevent or reduce the severity of the stroke).

An example of a disease or condition that may be detected, prevented, treated and/or diagnosed may be joint swelling. Joint swelling may be related to a disease, injury, or other condition, may be treated with pharmaceuticals or conservatively. The methods and apparatuses described herein may be use in particular to treat joint swelling instead of, or in addition to, other techniques for treating joint swelling. For example, joint swelling may be treated by the application of LT either to one or more anatomical regions of the user.

In general, joint swelling may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be muscle pain, strain and/or soreness. Muscle pain, strain and/or soreness may be related to a disease, injury, or other condition, may be treated with pharmaceuticals or conservatively. The methods and apparatuses described herein may be use in particular to treat muscle pain, strain and/or soreness instead of, or in addition to, other techniques for treating muscle pain, strain and/or soreness. For example, muscle pain, strain and/or soreness may be treated by the application of LT either to one or more anatomical regions of the user.

In general, muscle pain, strain and/or soreness may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be fibromyalgia. Fibromyalgia can be a disorder, may be treated with pharmaceuticals or conservatively. The methods and apparatuses described herein may be use in particular to treat fibromyalgia instead of, or in addition to, other techniques for treating fibromyalgia. For example, fibromyalgia may be treated by the application of LT either to one or more anatomical regions of the user.

In general, fibromyalgia may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be arthritis. Arthritis can be a disorder, and may be treated with pharmaceuticals or conservatively. The methods and apparatuses described herein may be use in particular to treat arthritis instead of, or in addition to, other techniques for treating arthritis. For example, arthritis may be treated by the application of LT either to one or more anatomical regions of the user.

In general, arthritis may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be delayed onset muscle soreness (DOMS). DOMS is a disorder, and may be treated with pharmaceuticals or conservatively. The methods and apparatuses described herein may be use in particular to treat DOMS instead of, or in addition to, other techniques for treating DOMS. For example, DOMS may be treated by the application of LT either to one or more anatomical regions of the user.

In general, DOMS may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be headaches (e.g., migraine headaches). Headaches may be treated with pharmaceuticals or conservatively. The methods and apparatuses described herein may be use in particular to treat headaches instead of, or in addition to, other techniques for treating headaches. For example, headaches may be treated by the application of LT either to one or more anatomical regions of the user.

In general, headaches may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be psoriasis. Psoriasis can be a disorder and may be treated with pharmaceuticals or conservatively. The methods and apparatuses described herein may be use in particular to treat psoriasis instead of, or in addition to, other techniques for treating psoriasis. For example, psoriasis may be treated by the application of LT either to one or more anatomical regions of the user.

In general, psoriasis may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be jaundice. Jaundice may be treated with pharmaceuticals or conservatively. The methods and apparatuses described herein may be use in particular to treat jaundice instead of, or in addition to, other techniques for treating jaundice. For example, jaundice may be treated by the application of LT either to one or more anatomical regions of the user.

In general, jaundice may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be hyperbilirubinemia. Hyperbilirubinemia is a disorder, may be treated with pharmaceuticals or conservatively. The methods and apparatuses described herein may be use in particular to treat hyperbilirubinemia instead of, or in addition to, other techniques for treating hyperbilirubinemia. For example, hyperbilirubinemia may be treated by the application of LT either to one or more anatomical regions of the user.

In w moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be depression (e.g., seasonal depression). Depression is a neurological disorder, may be treated with pharmaceuticals or conservatively. The methods and apparatuses described herein may be use in particular to treat depression instead of, or in addition to, other techniques for treating depression. For example, depression may be treated by the application of LT either to one or more anatomical regions of the user.

In general, depression may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be elevated inflammation (e.g., elevated inflammatory cytokines associated with a disease or condition). Elevated inflammation can have a negative impact on biological tissues and processes. The methods and apparatuses described herein may be use in particular to treat inflammation instead of, or in addition to, other techniques for treating inflammation. For example, inflammation may be treated by the application of LT either to one or more anatomical regions of the user. In some examples, an LT apparatus and method described herein can reduce pro-inflammatory cytokines and/or increase anti-inflammatory molecules.

In general, inflammation may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

An example of a disease or condition that may be detected, prevented, treated and/or diagnosed may be Alzheimer's Disease. Alzheimer's Disease is a neurological disorder, may be treated with pharmaceuticals or conservatively. This methods and apparatuses described herein may be use in particular to treat Alzheimer's Disease instead of, or in addition to, other techniques for treating Alzheimer's Disease. For example, Alzheimer's Disease may be treated by the application of LT either to one or more anatomical regions of the user.

In general, Alzheimer's Disease may be treated by applying LT during one or more treatment sessions as described above. Treatment may be passive (e.g., without the user/patient) exercising, or active, including actively moving or exercising. One or more treatment may be applied, including one or more 5-40 minute sessions (e.g., 10-30 min, 10-20 min, etc.). Multiple treatment sessions may be applied. For example, a treatment session may be repeated as needed, or every x days (e.g., every 2 days, every 3 days, every 4 days, every 5 days, every 6 days, every 7 days, every 8 days, every 9 days, every 10 days, etc.). In some examples, treatment may be repeated a decreasing frequency after an initially number of treatments.

Any of the methods and apparatuses described herein may be used for one or more therapeutic indication, such as for physiotherapy by a patient (user) recovering from an injury, surgery, etc.

In some examples, the user has or is at risk of developing a psychological disorder. Some non-limiting examples of psychological disorders may include: anxiety disorders, agoraphobia, generalized anxiety disorder, panic disorder, separation anxiety disorder, specific phobias, postpartum anxiety, social anxiety disorder, mood disorders, depressive disorders, major depressive disorder, persistent depressive disorder, previously known as dysthymia, peripartum depression, postpartum depression, premenstrual dysphoric disorder, seasonal affective disorder, situational depression, bipolar disorder, major depressive episode, hypomanic episode, manic episode, mixed features, cyclothymic disorder, additional specifiers for bipolar disorder, substance-related disorders, alcohol use disorder, opioid use disorder symptoms, substance use disorder, schizophrenia and related disorders, brief psychotic disorder, catatonia, delusional disorder, postpartum psychosis, psychotic disorder not otherwise specified, schizophrenia, schizoaffective disorder, schizophreniform disorder, schizotypal personality disorder, obsessive-compulsive disorder and related disorders, body dysmorphic disorder, hoarding disorder, dermatillomania, obsessive-compulsive disorder, trichotillomania, feeding and eating disorders, avoidant restrictive food intake disorder (ARFID), anorexia nervosa, binge eating disorder, bulimia nervosa, pica, rumination disorder, stress-related disorders, acute stress disorder, adjustment disorder, disinhibited social engagement disorder, post-traumatic stress disorder (PTSD), reactive attachment disorder, dissociative disorders, depersonalization-derealization disorder, dissociative amnesia, dissociative fugue, dissociative identity disorder, dissociative disorder not otherwise specified, neurodevelopmental disorders, attention deficit hyperactivity disorder (ADHD), autism spectrum disorder, Asperger's syndrome, Rett syndrome, expressive language disorder, intellectual disability, social (pragmatic) communication disorder, specific learning disorder, stereotypic movement disorder, transient tic disorder, personality disorders, antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, schizotypal personality disorder, sexual dysfunctions and paraphilic disorders, erectile disorder (ED), sexual arousal disorder, genito-pelvic pain/penetration disorder, dyspareunia, vaginismus, hypoactive sexual desire disorder, orgasmic disorders, paraphilias, exhibitionistic disorder, fetishistic disorder, frotteuristic disorder, pedophilic disorder, sexual masochism and sadism, transvestic disorder, voyeuristic disorder, persistent genital arousal disorder (PGAD), premature (early) ejaculation, sleep-wake disorders, circadian rhythm sleep-wake disorder, hypersomnolence, insomnia, nightmare disorder, narcolepsy, restless legs syndrome, non-rapid eye movement sleep arousal disorders, sleep terror disorder, sleepwalking disorder, sleep paralysis, neurocognitive disorders, Alzheimer's disease, major neurocognitive disorder, mild neurocognitive disorder, Parkinson's disease, childhood mental health disorders, conduct disorder, disorder of written expression, disruptive mood dysregulation disorder, encopresis, enuresis, oppositional defiant disorder, reading disorder, selective mutism, Tourette syndrome, mental health disorders and symptoms, bereavement, conversion disorder, diabulimia, gaming disorder, gender dysphoria, illness anxiety disorder, formerly known as hypochondriasis, intermittent explosive disorder, kleptomania, psychotic disorder not otherwise specified, pyromania, sex addiction, shared psychotic disorder, somatic symptom disorder, stuttering In some examples, the user has or is at risk of developing a dermatological disease or condition. Some non-limiting examples of dermatological diseases and conditions may include: Acne, Granuloma Annulare, Pimples, *Acanthosis nigricans*, Grover's Disease, *Pityriasis alba*, Acrochordons, Guttate Psoriasis, *Pityriasis lichenoides*, Actinic Keratosis, Hair Loss-Alopecia Areata, *Pityriasis rosea*, Age Spots, Hair Loss-Androgenic Alopecia, *Pityriasis rubra pilaris*, Allergic Contact Dermatitis, Hair Loss-Telogen Effluvium Plantar Warts, Anal Warts, Halo Nevus, Poison Ivy, Angioma, Hand Dermatitis, Poison Oak, Aphthous Ulcers, Heat Rash, Pompholyx, Athlete's Foot, Henoch-Schonlein Purpura, *Porphyria cutanea tarda*, Atopic Dermatitis, Herpes Simplex, Precancers of the Skin, Atypical Moles, Herpes Zoster (Shingles), Pruritus Ani (Itchy Butt), Barnacles of Aging, Hidradenitis Suppurativa, Pseudofolliculitis Barbae, Basal Cell Carcinoma, Hives, Psoriasis, Bateman's Purpura, Hyperhidrosis, Psoriasis of the Scalp, Bed Sores, Ichthyosis, Razor Bumps, Berloque Dermatitis, Impetigo, Rhus Allergy, Blau Syndrome, Intertrigo-Skin Rash, Rhyniophyma, Boils, Irritant vs. Allergic Dermatitis, Ring Worm-Body, Bruising Back of Arms, Jock Itch, Ring Worm-Scalp, Bullous Pemphigoid, Kaposi's Sarcoma, Rosacea, *Candida*, Keloids, Scabies, Carbuncles and Furuncles, Keratoacanthoma, Scar, Abnormal, Celluliti, Keratosis Pilaris, Schamberg's Disease, Cherry Angioma, Lentigines (Sun Spots), Scleroderma, Localized, Chiggers, Lichen Planus, Sebaceous Hyperplasia, Chilblains Inflammation, Lichen Planus Like Keratosis, Seborrheic Dermatitis, *Chondrodermatitis helicis*, Lichen Simplex Chronicus, Seborrheic Keratosis, Clark's Nevus, Lichen Sclerosus, Senile Angioma, Cold Sores, *Lichen striatus*, Shingles, Condylomata, Lupus of the Skin, Skin Aging, Cysts, Lyme Disease, Skin Tags, Dandruff, Lymphomatoid Papulosis, Solar Keratosis, Dandruff (Severe), Mask of Pregnancy, Squamous Cell Carcinoma, Darier's Disease, Mastocytosis Allergy, Stasis Dermatitis, Dermatofibroma, Melanoma, Stress Rash, Diaper Dermatitis, Melasma, Sun Burn, Discoid Lupus Erythematosus, Miliaria, Sun Damage, Dry Skin, Moles, Sun Spots, Dyshidrotic Dermatitis, Molluscum Contagiosum, Sweating, Excessive, Eczema, Atopic, Morgellons, Telogen Effluvium, Eczema, Dyshidrotic, Mycosis Fungoides, *Tinca capitis*, Eczema, Hands, Myxoid Cysts, *Tinea corporis*, Eczema Herpeticum, Nail Splitting, Brittle, Tinca Cruris, Eczema Localized, Nail Fungus, Tinca Pedis, Eczema, Nummular, Necrobiosis Lipoidica Diabeticorum, *Tinca versicolor*, EPP, Nickel Allergy, Urticaria, Erythema Multiforme, Nummular Dermatitis, Urticaria Pigmentosa, Erythema Nodosum, Onychomycosis, Vitiligo, Excoriation, Onychoschizia, Warts, Folliculitis, Pediculosis (Licc), Xanthomas, Folliculitis Keloidalis Nuchac, Perioral Dermatitis, Xerosis (Dry Skin), Fordyce's Condition, Pfiesteria, Yeast Infection, Skin, Frostbite, Photodermatitis, etc.

In some examples, the user has or is at risk of developing a neurological disorder. Some non-limiting examples of neurological disorders may include: Absence of the Septum Pellucidum, Acid Lipase Disease, Acid Maltase Deficiency, Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, AIDS, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Autism, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Discase, Blepharospasm, Bloch-Sulzberger Syndrome, Brachial Plexus Injuries, Bradbury-Eggleston Syndrome, Brain and Spinal Tumors, Brain Aneurysm, Brain Injury, Brown-Scquard Syndrome, Bulbospinal Muscular Atrophy, Cadasil, Canavan Disease, Carpal Tunnel Syndrome, Causalgia, Cavernomas, Cavernous Angioma, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Palsy, Cerebro-Oculo-Facio-Skeletal Syndrome, Charcot-Marie-Tooth Disease, Chiari Malformation, Chorca, Chronic Inflammatory Demyelinating Polyneuropathy (CIDP), Chronic Pain, Coffin Lowry Syndrome, Colpocephaly, Coma and Persistent Vegetative State, Congenital Facial Diplegia, Congenital Myasthenia, Congenital Myopathy, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Dancing Eyes-Dancing Feet Syndrome, Dandy-Walker Syndrome, Dawson Disease, Dementia, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Dysautonomia, Dysgraphia, Dyslexia, Dysphagia, Dyssynergia Cerebellaris Myoclonica. Dystonias, Early Infantile Epileptic Encephalopathy, Empty Sella Syndrome, Encephalitis, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyzes, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gangliosidoses, Gaucher's Disease, Gerstmann's Syndrome, Gerstmann-Straussler-Scheinker Disease, Giant Cell Arteritis, Giant Cell Inclusion Disease, Globoid Cell Leukodystrophy, Glossopharyngeal Neuralgia, Glycogen Storage Disease, Guillain-Barre Syndrome, Hallervorden-Spatz Disease, Head Injury, Hemicrania Continua, Hemifacial Spasm, Hemiplegia Alterans, Hereditary Neuropathies, Hereditary Spastic Paraplegia, Hercdopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydromyelia, Hypernychthemeral Syndrome, Hypersomnia, Hypertonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaac's Syndrome, Joubert syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kluver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Medullary Syndrome, Learning Disabilities, Leigh's Disease, Lennox-Gastaut Syndrome, Lesch Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus, Lyme Disease, Machado-Joseph Disease, Macrencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini-Strokes, Mitochondrial Myopathies, Motor Neuron Diseases, Moyamoya Disease, Mucolipidoses, Mucopolysaccharidoses, Multiple sclerosis (MS), Multiple System Atrophy, Muscular Dystrophy, Myasthenia Gravis, Myoclonus, Myopathy, Myotonia, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica or Devic's disease, Neuromyotonia, Neuronal Ceroid Lipofuscinosis, Neuronal Migration Disorders, Neuropathy, Neurosarcoidosis, Neurotoxicity, Nevus Cavernosus, Niemann-Pick Disease, Non 24 Sleep Wake Disorder, Normal Pressure Hydrocephalus, Occipital Neuralgia, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pantothenate Kinase-Associated Neurodegeneration, Parancoplastic Syndromes, Paresthesia, Parkinson's Disease, Paroxysmal Chorcoathetosis, Paroxysmal Hemicrania, Parry-Romberg, Pelizacus-Merzbacher Disease, Perineural Cysts, Periodic Paralyzes, Peripheral Neuropathy, Periventricular Leukomalacia, Pervasive Developmental Disorders, Pinched Nerve, Piriformis Syndrome, Plexopathy, Polymyositis, Pompe Disease, Porencephaly, Postherpetic Neuralgia, Postinfectious Encephalomyelitis, Post-Polio Syndrome, Postural Hypotension, Postural Orthostatic Tachyardia Syndrome (POTS), Primary Lateral Sclerosis, Prion Diseases, Progressive Multifocal Leukoencephalopathy, Progressive Sclerosing Poliodystrophy, Progressive Supranuclear Palsy, Prosopagnosia, Pseudotumor Cerebri, Ramsay Hunt Syndrome I, Ramsay Hunt Syndrome II, Rasmussen's Encephalitis, Reflex Sympathetic Dystrophy Syndrome, Refsum Disease, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Saint Vitus Dance, Sandhoff Disease, Schizencephaly, Septo-Optic Dysplasia, Shaken Baby Syndrome, Shingles, Shy-Drager Syndrome, Sjogren's Syndrome, Sleep Apnea, Sleeping Sickness, Sotos Syndrome, Spasticity, Spinal Cord Infarction, Spinal Cord Injury, Spinal Cord Tumors, Spinocerebellar Atrophy, Spinocerebellar Degeneration, Stiff-Person Syndrome, Striatonigral Degeneration, Stroke, Sturge-Weber Syndrome, SUNCT Headache, Syncope, Syphilitic Spinal Sclerosis, Syringomyelia, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tinnitus, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, Wolman's Disease, X-Linked Spinal and Bulbar Muscular Atrophy, and Zellweger Syndrome. The term neurological disorder may refer to any disease or condition relating to the nervous system. In some examples, neurological disorders may refer to neuromuscular diseases, muscular diseases, motor function disorders, injury, somatic diseases, or germline related diseases. In some examples, the term neurological disorder may refer to any disease or condition one reasonably skilled in the art would consider a neurological disorder.

In some examples, the user may be diagnosed with a disease or condition (e.g., a neurological disorder). In some examples, the user may be at risk of developing a disease or condition. In some examples, the user may have a disease or condition and not exhibit any sign or symptom of the disease or condition. In some examples, the user may exhibit a sign or symptom of a disease or condition without being diagnosed with the disease or condition.

In some examples, a user is at risk of a disease or condition based on the user's family history, age, sex, lifestyle, habits, comorbidity, genetic mutations, acquired molecular aberrations etc.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

In general, any of the methods and apparatuses described herein may be used for physiotherapy. For example, LT may be used as a rehabilitation tool for a range of conditions in adults and children, including (but not limited to) fatigue, injury, stroke, spinal cord injury, ABI and cerebral palsy. LT may be used alone or with other conventional physiotherapy adjuncts. For example LT may be used to reverse muscle atrophy and improved muscle strength; for support of function (i.e. stepping of the foot during gait), for improved local circulation and reduction in skin breakdown; for increasing and/or maintenance joint range of motion, for reduction of spasticity or muscle spasms; for an increase in cardiovascular function (e.g., via simultaneous activity of large muscle groups); for habilitation (e.g., learning new activity via movement normally unobtainable); for maintenance of bone density; and/or for restorative therapy (e.g., CNS cell birth & CNS myelination).

In general, any of the methods and apparatuses described herein may be used for cosmetic improvements in one or more biological tissues. In some examples, aging (e.g., senescence) may result in dysfunctional collagen, circulation, and/or composition of one or more biological tissues (e.g., wrinkling of skin). For example, LT may be used as a cosmetic tool to adjust or improve aesthetics of one or more biological tissues. For example, reducing oxidative stress by applying LT with an LT apparatus can improve intracellular and extracellular composition and function resulting in improved aesthetic of the user.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory. Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for reducing recovery time for a medical procedure, the method comprising:

positioning, prior to performing the medical procedure, an electrical muscle stimulation (EMS) garment on a patient, the EMS garment having one or more electrodes located in operable communication with one or more target muscle groups associated with the medical procedure;

establishing a stimulation protocol based on the medical procedure; and supplying stimulation to the one or more target muscle groups via EMS power from the one or more electrodes for a training period prior to performing the medical procedure, wherein the medical procedure is a surgical procedure.

2. The method of claim 1, wherein the EMS garment comprises a torso portion, lower portion, head portion, or a combination thereof.

3. The method of claim 1, wherein the one or more electrodes are disposed on an inner surface of the EMS garment, wherein the positioning comprises wearing, by the patient, the EMS garment.

4. The method of claim 1, wherein stimulation is supplied to the one or more target muscle groups for a treatment period prior to the surgical procedure for a plurality of sessions within one month of the surgical procedure.

5. The method of claim 1, wherein stimulation is supplied to the one or more target muscle groups for a treatment period prior to the surgical procedure for a plurality of sessions, wherein a last session prior to the surgical procedure is within one week of the surgical procedure.

6. The method of claim 1, further comprising updating the stimulation protocol based on a biometric data from one or more sensors, wherein the EMS power, duration, pattern, location, or a combination thereof are updated based on the biometric data.

7. The method of claim 1, wherein the stimulation protocol is configured to increase muscle tone.

8. The method of claim 1, wherein the stimulation protocol is configured to increase blood flow to the one or more target muscle groups.

9. The method of claim 1, wherein the stimulation protocol is configured to decrease a recovery time from the medical procedure.

10. The method of claim 1, wherein the stimulation protocol comprises an increasing maximum suppliable EMS power based on the medical procedure or the duration between the medical procedure and first application of EMS.

11. The method of claim 1, wherein the EMS power is based on the medical procedure, a user provided input, a power level provided by clinician, or a combination thereof.

12. The method of claim 1, wherein the EMS power is adjustable based on biometric data acquired by one or more sensors in operable communication with the EMS garment.

13. The method of claim 1, wherein establishing the stimulation protocol comprising selecting a predetermined stimulation protocol based on the medical procedure.

14. The method of claim 1, wherein the stimulation protocol is adjustable by a controller.

15. The method of claim 1, further comprising determining pre-procedure muscle characteristics via one of more sensors operably coupled to the EMS garment, the pre-procedure muscle characteristics based at least in part on muscle tone before the medical procedure.

16. The method of claim 1, wherein stimulation is supplied to the one or more target muscle groups before surgery, after surgery or a combination thereof.

17. A method of preventing muscle atrophy, the method comprising:

establishing a stimulation protocol based on patient-specific data;

positioning an electrical muscle stimulation (EMS) garment on a patient, the EMS garment having one or more electrodes locatable in direct contact with the patient's skin; and supplying stimulation according to the stimulation protocol to one or more target muscle groups, via EMS power from the one or more electrodes, wherein the stimulation is supplied prior to a surgical procedure.

18. The method of claim 17, wherein the stimulation protocol is configured to decrease a recovery period after the surgical procedure.

19. A method for reducing recovery time for a medical procedure, the method comprising:

positioning, prior to performing the medical procedure, an electrical muscle stimulation (EMS) garment on a patient, the EMS garment having one or more electrodes located in operable communication with one or more target muscle groups associated with the medical procedure;

establishing a stimulation protocol based on the medical procedure, wherein the medical procedure is a surgical procedure; and supplying stimulation to the one or more target muscle groups via EMS power from the one or more electrodes for a training period within one month prior to performing the medical procedure.

* * * * *